(12) United States Patent
Dimitrov et al.

(10) Patent No.: US 7,824,681 B2
(45) Date of Patent: Nov. 2, 2010

(54) HUMAN MONOCLONAL ANTIBODIES THAT SPECIFICALLY BIND IGF-II

(75) Inventors: Dimiter S. Dimitrov, Frederick, MD (US); Yang Feng, Frederick, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 285 days.

(21) Appl. No.: 12/063,749

(22) PCT Filed: Aug. 15, 2006

(86) PCT No.: PCT/US2006/031814

§ 371 (c)(1), (2), (4) Date: Feb. 13, 2008

(87) PCT Pub. No.: WO2007/022172

PCT Pub. Date: Feb. 22, 2007

(65) Prior Publication Data

US 2008/0193465 A1 Aug. 14, 2008

Related U.S. Application Data

(60) Provisional application No. 60/709,226, filed on Aug. 17, 2005, provisional application No. 60/798,817, filed on May 8, 2006.

(51) Int. Cl.
*A61K 39/395* (2006.01)

(52) U.S. Cl. ............... 424/145.1; 424/133.1; 424/135.1; 424/158.1; 435/69.1; 435/320.1; 435/325; 435/328; 435/336; 435/7.1; 435/7.2; 530/350; 530/387.3; 530/388.24; 530/391.3; 536/23.5

(58) Field of Classification Search ................. 530/350, 530/387.3, 388.24, 391.3; 424/145.1, 133.1, 424/135.1, 152.1, 158.1; 536/23.5; 435/7.1, 435/7.2, 69.1, 320.1, 325, 328, 336
See application file for complete search history.

(56) References Cited

PUBLICATIONS

Feng et al. (Mol. Cancer Ther. 2006; 5 (1): 114-120).*
Kimura et al. (Clin. Cancer Res. 2010; 16: 121-129).*
Bergmann et al., "Insulin-like growth factor II activates mitogenic signaling in pancreatic cancer calls via IRS-1: In vivo evidence for an islet-cancer cell axis," *International Journal of Oncology*, 9:487-492 (1996).
Feng et al., "Noval human monoclonal antibodies to insulin-like growth factor (IGF)-II that potently inhibit the IGS receptor type I signal transduction function," Molecular Cancer Therapeutics, 5(1):114-120, (Jan. 2006).
Geneseq, Accession No. GSN:ADR23364, "Human CD72-targeted IgG1 light chain," retrieved from EBI, (Nov. 4, 2004).
Goya, "Growth Inhibition of Human Prostate Cancer Cells in Human Adult Bone Implanted into Nonobese Diabetic/Severe Combined Immunodeficient Mice by Ligand-Specific Antibody to Human Insulin-Like Growth Factors," *Cancer Research*, 64:6252-6258 (Sep. 1, 2004).
Miyamoto et al., "Blockade of Paracrine Supply of Insulin-Like Growth Factors Using Neutralizing Antibodies Suppresses the Liver Metastasis of Human Colorectal Cancers," Clinical Cancer Research, 11(9):3494-3502 (May 1, 2005).
Singh et al., "Proliferation and Differentiation of a Human Colon Cancer Cell Line (CaCo2) Is Associated with Significant Changes in the Expression and Secretion of Insulin-Like Growth Factor (IGF) IGF-II and IGF Binding Protein-4: Role of IGF-II," *Endocrinology*, 137(5): 1764-1774 (1996).
Tanaka et al., "Identification of a Family of Insulin-Like Growth Factor II Secreted by Cultured Rat Epithelial-Like Cell Line 18,54-SF: Application of a Monoclonal Antibody," *Endocrinology*, 124(2):870-877 (1989).
Yu and Rohan, "Role of the Insulin-Like Growth Factor Family in Cancer Development and Progression," Journal of the National Cancer Institute, 92(18):1472-1488, (Sep. 20, 2000).

* cited by examiner

*Primary Examiner*—Stephen L Rawlings
(74) *Attorney, Agent, or Firm*—Klarquist Sparkman, LLP

(57) ABSTRACT

Disclosed herein are isolated monoclonal human antibodies that specifically binds insulin-like growth factor II (IGF-II) with an equilibrium dissociation constant ($K_d$) of 1 nM or less, wherein the antibody bind IGF-I with an equilibrium dissociation constant ($K_d$) of 1 mM or greater. The antibodies inhibit phosphorylation of the insulin-like growth factor receptor. Nucleic acids encoding these antibodies, expression vectors including these nucleic acids, and isolated host cells that express the nucleic acids are also disclosed. The antibodies can be used to detect human IGF-II in a sample. Methods of diagnosing a tumor are disclosed herein that utilize these antibodies. Methods of treating a subject with a tumor are also disclosed.

31 Claims, 11 Drawing Sheets

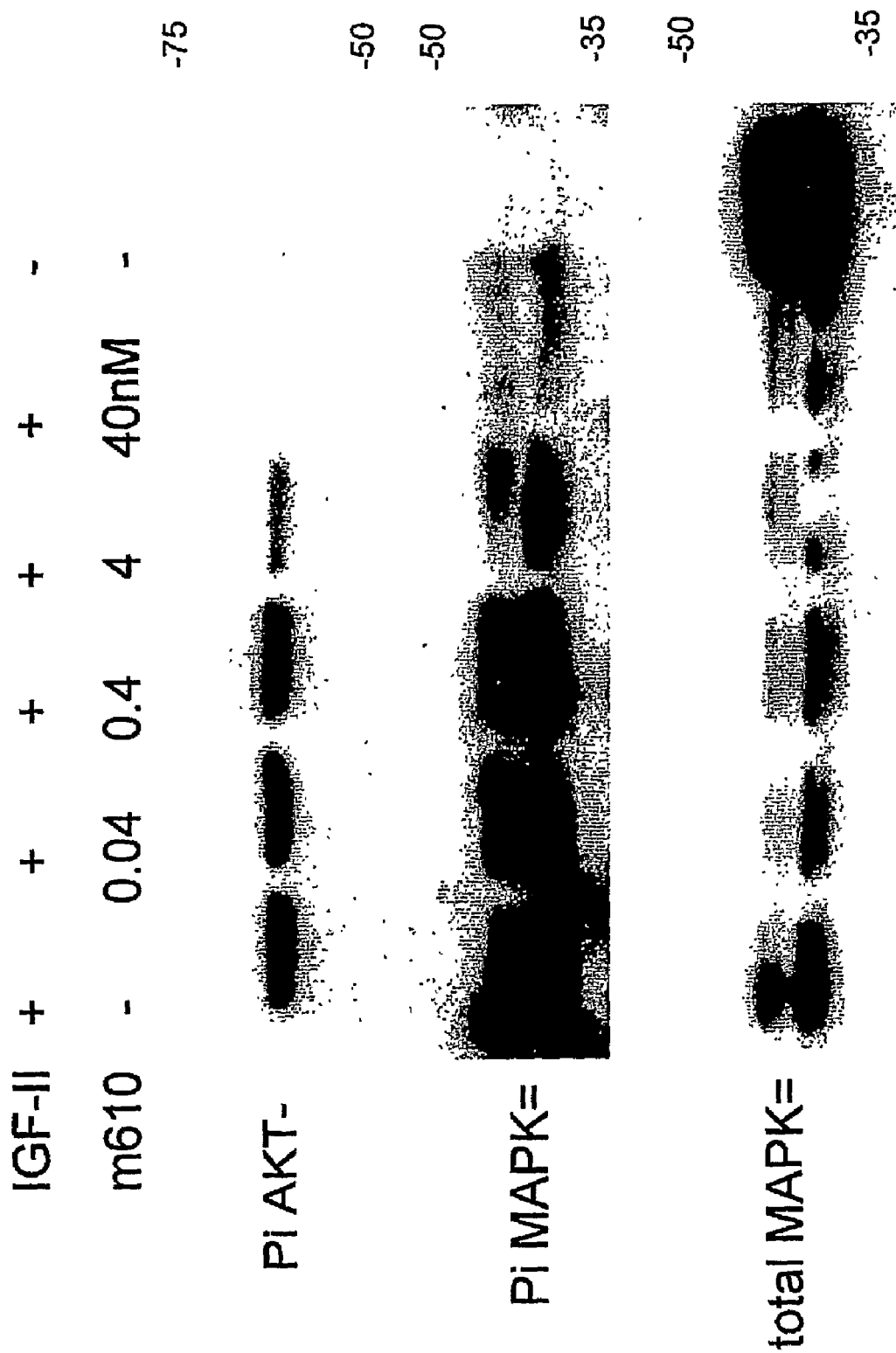

SEQUENCE LISTING

<160> NUMBER OF SEQ ID NOS: 18

<210> SEQ ID NO 1
<211> LENGTH: 22
<212> TYPE: PRT
<213> ORGANISM: Homo sapiens

<400> SEQUENCE: 1

Gly Ile Val Glu Gln Cys Cys Thr Ser Ile Cys Ser Leu Tyr Gln Leu
1               5                   10                  15

Glu Asn Asn Tyr Cys Asn
            20

<210> SEQ ID NO 2
<211> LENGTH: 30
<212> TYPE: PRT
<213> ORGANISM: Homo sapiens

<400> SEQUENCE: 2

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 3
<211> LENGTH: 165
<212> TYPE: PRT
<213> ORGANISM: Homo sapiens

<400> SEQUENCE: 3

Met Thr Ala Pro Ala Ile Lys Ile His Ile Met Ser Ser Ser His Leu
1               5                   10                  15

Phe Tyr Leu Ala Leu Cys Leu Leu Thr Phe Thr Ser Ser Thr Thr Ala
            20                  25                  30

Gly Pro Glu Thr Leu Cys Gly Ala Glu Leu Val Asp Ala Leu Gln Phe
        35                  40                  45

Val Cys Gly Pro Arg Gly Phe Tyr Phe Asn Lys Pro Thr Gly Tyr Gly
    50                  55                  60

Ser Ser Ile Arg Arg Ala Pro Gln Thr Gly Ile Val Asp Glu Cys Cys
65                  70                  75                  80

Phe Arg Ser Cys Asp Leu Arg Arg Leu Glu Met Tyr Cys Ala Pro Leu
                85                  90                  95

Lys Pro Thr Lys Ala Ala Arg Ser Ile Arg Ala Gln Arg His Thr Asp
            100                 105                 110

Met Pro Lys Thr Gln Lys Ser Pro Ser Leu Ser Thr Asn Lys Lys Thr
        115                 120                 125

Lys Leu Gln Arg Arg Arg Lys Gly Glu Pro Lys Thr His Pro Glu Gly
    130                 135                 140

Glu Gln Glu Glu Val Thr Glu Ala Thr Arg Lys Ile Arg Gly Pro Arg

```
                145                 150                 155                 160

Glu Lys Arg Leu Gly
                165

<210> SEQ ID NO 4
<211> LENGTH: 70
<212> TYPE: PRT
<213> ORGANISM: Homo sapiens

<400> SEQUENCE: 4

Phe Thr Ser Ser Thr Thr Ala Gly Pro Glu Thr Leu Cys Gly Ala Glu
1               5                   10                  15

Leu Val Asp Ala Leu Gln Phe Val Cys Gly Pro Arg Gly Phe Tyr Phe
            20                  25                  30

Asn Lys Pro Thr Gly Tyr Gly Ser Ser Ile Arg Arg Ala Pro Gln Thr
        35                  40                  45

Gly Ile Val Asp Glu Cys Cys Phe Arg Ser Cys Asp Leu Arg Arg Leu
    50                  55                  60

Glu Met Tyr Cys Ala Pro
65                  70

<210> SEQ ID NO 5
<211> LENGTH: 180
<212> TYPE: PRT
<213> ORGANISM: Homo sapiens

<400> SEQUENCE: 5

Met Gly Ile Pro Met Gly Lys Ser Met Leu Val Leu Leu Thr Phe Leu
1               5                   10                  15

Ala Phe Ala Ser Cys Cys Ile Ala Ala Tyr Arg Pro Ser Glu Thr Leu
            20                  25                  30

Cys Gly Gly Glu Leu Val Asp Thr Leu Gln Phe Val Cys Gly Asp Arg
        35                  40                  45

Gly Phe Tyr Phe Ser Arg Pro Ala Ser Arg Val Ser Arg Arg Ser Arg
    50                  55                  60

Gly Ile Val Glu Glu Cys Cys Phe Arg Ser Cys Asp Leu Ala Leu Leu
65                  70                  75                  80

Glu Thr Tyr Cys Ala Thr Pro Ala Lys Ser Glu Arg Asp Val Ser Thr
            85                  90                  95

Pro Pro Thr Val Leu Pro Asp Asn Phe Pro Arg Tyr Pro Val Gly Lys
        100                 105                 110

Phe Phe Gln Tyr Asp Thr Trp Lys Gln Ser Thr Gln Arg Leu Arg Arg
    115                 120                 125

Gly Leu Pro Ala Leu Leu Arg Ala Arg Arg Gly His Val Leu Ala Lys
130                 135                 140

Glu Leu Glu Ala Phe Arg Glu Ala Lys Arg His Arg Pro Leu Ile Ala
145                 150                 155                 160

Leu Pro Thr Gln Asp Pro Ala His Gly Gly Ala Pro Pro Glu Met Ala
            165                 170                 175

Ser Asn Arg Lys
            180

<210> SEQ ID NO 6
<211> LENGTH: 67
<212> TYPE: PRT
<213> ORGANISM: Homo sapiens

<400> SEQUENCE: 6
```

```
Ala Tyr Arg Pro Ser Glu Thr Leu Cys Gly Gly Glu Leu Val Asp Thr
1               5                   10                  15

Leu Gln Phe Val Cys Gly Asp Arg Gly Phe Tyr Phe Ser Arg Pro Ala
            20                  25                  30

Ser Arg Val Ser Arg Arg Ser Arg Gly Ile Val Glu Glu Cys Cys Phe
        35                  40                  45

Arg Ser Cys Asp Leu Ala Leu Leu Glu Thr Tyr Cys Ala Thr Pro Ala
    50                  55                  60

Lys Ser Glu
65

<210> SEQ ID NO 7
<211> LENGTH: 227
<212> TYPE: PRT
<213> ORGANISM: Homo sapiens
<220> FEATURE:
<221> NAME/KEY: MISC_FEATURE
<222> LOCATION: (37)..(47)
<223> OTHER INFORMATION: CDR-L1
<220> FEATURE:
<221> NAME/KEY: MISC_FEATURE
<222> LOCATION: (60)..(68)
<223> OTHER INFORMATION: CDR-L2
<220> FEATURE:
<221> NAME/KEY: MISC_FEATURE
<222> LOCATION: (99)..(109)
<223> OTHER INFORMATION: CDR-L3

<400> SEQUENCE: 7

Ala Gly Phe Ala Thr Val Ala Gln Ala Ser Asp Ile Gln Met Thr Gln
1               5                   10                  15

Ser Pro Ser Ser Val Ser Ala Ser Val Gly Asp Arg Val Thr Ile Thr
            20                  25                  30

Cys Arg Ala Ser Gln Gly Ile Ser Ser Trp Leu Val Trp Tyr Gln Gln
        35                  40                  45

Lys Pro Gly Lys Ala Pro Lys Leu Leu Ile Tyr Ala Ala Ser Arg Leu
    50                  55                  60

Gln Ser Gly Val Pro Ser Arg Phe Ser Gly Ser Gly Ser Gly Thr Leu
65                  70                  75                  80

Phe Thr Leu Ile Ile Asn Asn Leu Gln Pro Glu Asp Phe Ala Thr Tyr
                85                  90                  95

Tyr Cys Gln Gln Ser Asn Ser Val Pro Leu Thr Phe Gly Gly Gly Thr
            100                 105                 110

Lys Val Glu Ile Lys Arg Thr Val Ala Ala Pro Ser Val Phe Ile Phe
        115                 120                 125

Pro Pro Ser Asp Glu Gln Leu Lys Ser Gly Thr Ala Ser Val Val Cys
    130                 135                 140

Leu Leu Asn Asn Phe Tyr Pro Arg Glu Ala Lys Val Gln Trp Lys Val
145                 150                 155                 160

Asp Asn Ala Leu Gln Ser Gly Asn Ser Gln Glu Ser Val Thr Glu Gln
                165                 170                 175

Asp Ser Lys Asp Ser Thr Tyr Ser Leu Ser Ser Thr Leu Thr Leu Ser
            180                 185                 190

Lys Ala Asp Tyr Glu Lys His Lys Val Tyr Ala Cys Glu Val Thr His
        195                 200                 205

Gln Gly Leu Ser Ser Pro Val Thr Lys Ser Phe Asn Arg Gly Gly Val
    210                 215                 220

Asn Ser Arg
```

```
<210> SEQ ID NO 8
<211> LENGTH: 224
<212> TYPE: PRT
<213> ORGANISM: Homo sapiens
<220> FEATURE:
<221> NAME/KEY: MISC_FEATURE
<222> LOCATION: (37)..(47)
<223> OTHER INFORMATION: CDR-L1
<220> FEATURE:
<221> NAME/KEY: MISC_FEATURE
<222> LOCATION: (60)..(68)
<223> OTHER INFORMATION: CDR-L2
<220> FEATURE:
<221> NAME/KEY: MISC_FEATURE
<222> LOCATION: (99)..(109)
<223> OTHER INFORMATION: CDR-L3

<400> SEQUENCE: 8

Ala Gly Phe Ala Thr Val Ala Gln Ala Cys Arg Ile Gln Met Thr Gln
 1               5                  10                  15

Ser Pro Ser Pro Leu Ser Ala Ser Val Gly Asp Arg Val Thr Ile Thr
            20                  25                  30

Cys Arg Ala Ser Gln Ser Ile Ser Ser Tyr Leu Asn Trp Tyr Gln Gln
        35                  40                  45

Lys Pro Gly Lys Ala Pro Lys Leu Leu Ile Tyr Ala Ala Ser Ser Leu
    50                  55                  60

Gln Ser Gly Val Pro Ser Arg Phe Ser Gly Ser Gly Ser Gly Thr Asp
65                  70                  75                  80

Phe Thr Leu Thr Ile Ser Ser Leu Gln Pro Glu Asp Phe Ala Thr Tyr
                85                  90                  95

Tyr Cys Gln Gln Ser Tyr Ser Thr Pro Leu Thr Phe Gly Gly Gly Thr
            100                 105                 110

Lys Val Glu Ile Lys Arg Thr Val Ala Ala Pro Ser Val Phe Ile Phe
        115                 120                 125

Pro Pro Ser Asp Glu Gln Leu Lys Ser Gly Thr Ala Ser Val Val Cys
    130                 135                 140

Leu Leu Asn Asn Phe Tyr Pro Arg Glu Ala Lys Val Gln Trp Lys Val
145                 150                 155                 160

Asp Asn Ala Leu Gln Ser Gly Asn Ser Gln Glu Ser Val Thr Glu Gln
                165                 170                 175

Asp Ser Lys Asp Ser Thr Tyr Ser Leu Ser Ser Thr Leu Thr Leu Ser
            180                 185                 190

Lys Ala Asp Tyr Glu Lys His Lys Val Tyr Ala Cys Glu Val Thr His
        195                 200                 205

Gln Gly Leu Ser Ser Pro Val Thr Lys Ser Phe Asn Arg Gly Glu Cys
    210                 215                 220

<210> SEQ ID NO 9
<211> LENGTH: 224
<212> TYPE: PRT
<213> ORGANISM: Homo sapiens
<220> FEATURE:
<221> NAME/KEY: MISC_FEATURE
<222> LOCATION: (37)..(42)
<223> OTHER INFORMATION: CDR-L1
<220> FEATURE:
<221> NAME/KEY: MISC_FEATURE
<222> LOCATION: (60)..(69)
<223> OTHER INFORMATION: CDR-L2
<220> FEATURE:
<221> NAME/KEY: MISC_FEATURE
```

<222> LOCATION: (99)..(109)
<223> OTHER INFORMATION: CDR-L3

<400> SEQUENCE: 9

```
Ala Trp Leu Val Ser Ser Val Ala Gln Ala Ser Ser Tyr Glu Ile Thr
1               5                   10                  15

Gln Pro Pro Ser Val Ser Val Thr Pro Gly Gln Thr Ala Arg Ile Thr
            20                  25                  30

Cys Ser Gly Asp Ala Leu Pro Lys His Phe Ala Tyr Trp Tyr Gln Gln
        35                  40                  45

Lys Pro Gly Gln Ala Pro Val Leu Ile Ile Tyr Lys Asp Thr Glu Arg
    50                  55                  60

Pro Ser Gly Ile Pro Glu Arg Phe Ser Gly Ser Asn Ser Gly Asn Thr
65                  70                  75                  80

Ala Thr Leu Thr Ile Ser Arg Val Glu Ala Gly Asp Glu Ala Asp Tyr
                85                  90                  95

Tyr Cys Gln Val Trp Asp Ser Ser Gly Trp Val Phe Gly Gly Gly
            100                 105                 110

Thr Lys Leu Thr Val Gln Gly Gln Pro Lys Ala Ala Pro Ser Val Thr
            115                 120                 125

Leu Phe Pro Pro Ser Ser Glu Glu Leu Gln Ala Asn Lys Ala Thr Leu
        130                 135                 140

Val Cys Leu Ile Ser Asp Phe Tyr Pro Gly Ala Val Thr Val Ala Trp
145                 150                 155                 160

Lys Ala Asp Ser Ser Pro Val Lys Ala Gly Val Glu Thr Thr Thr Pro
                165                 170                 175

Ser Lys Gln Ser Asn Asn Lys Tyr Ala Ala Ser Ser Tyr Leu Ser Leu
            180                 185                 190

Thr Pro Glu Gln Trp Lys Ser His Lys Ser Tyr Ser Cys Gln Val Thr
        195                 200                 205

His Glu Gly Ser Thr Val Glu Lys Thr Val Ala Pro Thr Glu Cys Ser
    210                 215                 220
```

<210> SEQ ID NO 10
<211> LENGTH: 254
<212> TYPE: PRT
<213> ORGANISM: Homo sapiens
<220> FEATURE:
<221> NAME/KEY: MISC_FEATURE
<222> LOCATION: (34)..(41)
<223> OTHER INFORMATION: CDR-H1
<220> FEATURE:
<221> NAME/KEY: MISC_FEATURE
<222> LOCATION: (59)..(65)
<223> OTHER INFORMATION: CDR-H2
<220> FEATURE:
<221> NAME/KEY: MISC_FEATURE
<222> LOCATION: (105)..(119)
<223> OTHER INFORMATION: CDR-H3

<400> SEQUENCE: 10

```
Thr Arg Cys Gln Pro Ala Met Ala Gln Val Gln Leu Val Glu Ser Gly
1               5                   10                  15

Ala Glu Val Lys Lys Pro Gly Ala Ser Val Lys Val Ser Cys Lys Ala
            20                  25                  30

Ser Gly Tyr Thr Phe Thr Ser Tyr Tyr Met His Trp Val Arg Gln Ala
        35                  40                  45

Pro Gly Gln Gly Leu Glu Trp Met Gly Ile Ile Asn Pro Ser Gly Gly
    50                  55                  60
```

```
Ser Thr Ser Tyr Ala Gln Lys Phe Gln Gly Arg Val Thr Met Thr Arg
 65                  70                  75                  80

Asp Thr Ser Thr Ser Thr Val Tyr Met Glu Leu Ser Ser Leu Arg Ser
                 85                  90                  95

Glu Asp Thr Ala Val Tyr Tyr Cys Ala Arg Asp Arg Ser Ile Ala Ala
            100                 105                 110

Met Gly Trp Phe Asp His Trp Gly Gln Gly Thr Leu Val Thr Val Ser
            115                 120                 125

Ser Ala Ser Thr Lys Gly Pro Ser Val Phe Pro Leu Ala Pro Ser Ser
        130                 135                 140

Lys Ser Thr Ser Gly Gly Thr Ala Ala Leu Gly Cys Leu Val Lys Asp
145                 150                 155                 160

Tyr Phe Pro Glu Pro Val Thr Val Ser Trp Asn Ser Gly Ala Leu Thr
                165                 170                 175

Ser Gly Val His Thr Phe Pro Ala Val Leu Gln Ser Ser Gly Leu Tyr
            180                 185                 190

Ser Leu Ser Ser Val Val Thr Val Pro Ser Ser Ser Leu Gly Thr Gln
        195                 200                 205

Thr Tyr Ile Cys Asn Val Asn His Lys Pro Ser Asn Thr Lys Val Asp
        210                 215                 220

Lys Lys Val Glu Pro Lys Ser Cys Asp Lys Thr Ser Gly Gln Ala Gly
225                 230                 235                 240

His His His His His His Gly Asp Tyr Lys Asp Asp Asp
                245                 250

<210> SEQ ID NO 11
<211> LENGTH: 255
<212> TYPE: PRT
<213> ORGANISM: Homo sapiens
<220> FEATURE:
<221> NAME/KEY: MISC_FEATURE
<222> LOCATION: (34)..(41)
<223> OTHER INFORMATION: CDR-H1
<220> FEATURE:
<221> NAME/KEY: MISC_FEATURE
<222> LOCATION: (59)..(65)
<223> OTHER INFORMATION: CDR-H2
<220> FEATURE:
<221> NAME/KEY: MISC_FEATURE
<222> LOCATION: (105)..(118)
<223> OTHER INFORMATION: CDR-H3

<400> SEQUENCE: 11

Thr Arg Cys Gln Pro Ala Met Ala Gln Val Gln Leu Val Gln Ser Gly
  1               5                  10                  15

Ala Glu Val Lys Lys Pro Gly Ala Ser Val Lys Val Ser Cys Lys Ala
             20                  25                  30

Ser Gly Tyr Thr Phe Thr Ser Tyr Tyr Met His Trp Val Arg Gln Ala
         35                  40                  45

Pro Gly Gln Gly Leu Glu Trp Met Gly Ile Ile Asn Pro Ser Gly Gly
     50                  55                  60

Ser Thr Ser Tyr Ala Gln Lys Phe Gln Gly Arg Val Thr Met Thr Arg
 65                  70                  75                  80

Asp Thr Ser Thr Ser Thr Val Tyr Met Glu Leu Ser Arg Leu Arg Ser
                 85                  90                  95

Asp Asp Thr Ala Val Tyr Tyr Cys Ala Arg Asp Val Gln Trp Leu Ala
            100                 105                 110

Tyr Gly Met Asp Val Trp Gly Gln Gly Thr Thr Val Thr Val Ser Ser
            115                 120                 125
```

```
Ala Ser Thr Lys Gly Pro Ser Val Phe Pro Leu Ala Pro Ser Ser Lys
        130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
210                 215                 220

Lys Val Glu Pro Lys Ser Cys Asp Lys Thr Ser Gly Gln Ala Gly His
225                 230                 235                 240

His His His His Gly Asp Tyr Lys Asp Asp Asp Asp Lys Gly
            245                 250                 255

<210> SEQ ID NO 12
<211> LENGTH: 244
<212> TYPE: PRT
<213> ORGANISM: Homo sapiens
<220> FEATURE:
<221> NAME/KEY: MISC_FEATURE
<222> LOCATION: (95)..(117)
<223> OTHER INFORMATION: CDR-H3

<400> SEQUENCE: 12

Ser Gln Val Gln Val Leu Val Lys Pro Ser Gln Thr Leu Ser Leu Thr
1               5                   10                  15

Cys Ala Ile Ser Gly Asp Ser Val Ser Ser Asn Ser Ala Ala Trp Asn
            20                  25                  30

Trp Ile Arg Gln Ser Pro Ser Arg Gly Leu Glu Trp Leu Gly Arg Thr
        35                  40                  45

Tyr Tyr Arg Ser Lys Trp Tyr Asn Asp Tyr Ala Val Ser Val Lys Ser
    50                  55                  60

Arg Ile Thr Ile Asn Pro Asp Thr Ser Lys Asn Gln Phe Ser Leu Gln
65                  70                  75                  80

Leu Asn Ser Val Thr Pro Glu Asp Thr Ala Val Tyr Tyr Cys Ala Arg
                85                  90                  95

Glu Lys Gly Ile Gly Arg Gly Ile Thr Gly Thr Thr Ile Pro Tyr Asn
            100                 105                 110

Trp Phe Asp Pro Trp Gly Gln Gly Thr Leu Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
210                 215                 220
```

Val Glu Pro Lys Ser Cys Asp Lys Thr Ser Gly Gln Ala Gly His His
225                 230                 235                 240

His His His His

<210> SEQ ID NO 13
<211> LENGTH: 874
<212> TYPE: DNA
<213> ORGANISM: Homo sapiens

<400> SEQUENCE: 13

| | | | | | |
|---|---|---|---|---|---|
| ggctggtttc | gctaccgtgg | cccaggcgtc | cgacatccag | atgacccagt | ctccatcttc | 60 |
| cgtgtctgca | tctgtaggag | acagagttac | catcacttgt | cgggcgagtc | agggtattag | 120 |
| tagttggttg | gtctggtatc | aacaaaaacc | cggaaaagcc | cctaaactcc | tgatctatgc | 180 |
| tgcatcccgt | ttacaaagtg | gggtcccatc | aaggttcagc | ggcagtggat | ctgggacact | 240 |
| tttcactctc | atcatcaaca | acctgcagcc | tgaagatttt | gcaacttact | attgtcaaca | 300 |
| gtctaatagt | gtccctctca | ctttcggcgg | agggaccaag | gtggagatca | agcgaactgt | 360 |
| ggctgcacca | tctgtcttca | tcttcccgcc | atctgatgag | cagttgaaat | ctggaactgc | 420 |
| ctctgttgtg | tgcctgctga | ataacttcta | tcccagagag | gccaaagtac | agtggaaggt | 480 |
| ggataacgcc | ctccaatcgg | gtaactccca | ggagagtgtc | acagagcagg | acagcaagga | 540 |
| cagcacctac | agcctcagca | gcaccctgac | gctgagcaaa | gcagactacg | agaaacacaa | 600 |
| agtctacgcc | tgcgaagtca | cccatcaggg | cctgagctcg | cccgtcacaa | agagcttcaa | 660 |
| caggggaggt | gttaattcta | gataattaat | taggaggaat | ttaaaatgaa | atacctattg | 720 |
| cctacggcag | ccgctggatt | gttattactc | gctgcccaac | cagccatggc | ccaggtgcag | 780 |
| ctggtggagt | ctggggctga | ggtgaagaaa | gcctgggcct | cagtgaggtt | tcctgcaggc | 840 |
| atctggatac | ccttcaccag | ctactatatg | cact | | | 874 |

<210> SEQ ID NO 14
<211> LENGTH: 709
<212> TYPE: DNA
<213> ORGANISM: Homo sapiens

<400> SEQUENCE: 14

| | | | | | |
|---|---|---|---|---|---|
| tgcagctggt | ggagtctggg | gctgaggtga | agaagcctgg | ggcctcagtg | aaggtttcct | 60 |
| gcaaggcatc | tggatacacc | ttcaccagct | actatatgca | ctgggtgcga | caggcccctg | 120 |
| gacaagggct | tgagtggatg | ggaataatca | accctagtgg | tggtagcaca | agctacgcac | 180 |
| agaagttcca | gggcagagtc | accatgacca | gggacacgtc | cacgagcaca | gtctacatgg | 240 |
| agctgagcag | cctgagatct | gaggacacgg | ccgtgtatta | ctgtgcgaga | gataggagta | 300 |
| tagcagcaat | ggggtggttc | gaccactggg | gccagggaac | cctggtcacc | gtctcctcag | 360 |
| cctccaccaa | gggcccatcg | gtcttccccc | tggcaccctc | ctccaagagc | acctctgggg | 420 |
| gcacagcggc | cctgggctgc | ctggtcaagg | actacttccc | cgaaccggtg | acggtgtcgt | 480 |
| ggaactcagg | cgccctgacc | agcggcgtgc | acaccttccc | ggctgtccta | cagtcctcag | 540 |
| gactctactc | cctcagcagc | gtggtgaccg | tgccctccag | cagcttgggc | acccagacct | 600 |
| acatctgcaa | cgtgaatcac | aagcccagca | acaccaaggt | ggacaagaaa | gttgagccca | 660 |
| aatcttgtga | caaaactagt | ggccaggccg | gccaccacca | ccaccacca | | 709 |

<210> SEQ ID NO 15
<211> LENGTH: 776
<212> TYPE: DNA

<210> SEQ ID NO 15
<400> SEQUENCE: 15

```
gctggtttcg ctaccgtggc ccaggcgtgc cgaatccaga tgacccagtc tccatccccc      60
ctgtctgcat ctgtaggaga cagagtcacc atcacttgcc gggcaagtca gagcattagc     120
agctatttaa attggtatca gcagaaacca gggaaagccc ctaagctcct gatctatgct     180
gcatccagtt tgcaaagtgg ggtcccatca aggttcagtg cagtggatc tgggacagat     240
ttcactctca ccatcagcag tctgcaacct gaagattttg caacttacta ctgtcaacag     300
agttacagta ccccgctcac tttcggcgga gggaccaagg tggagatcaa acgaactgtg     360
gctgcaccat ctgtcttcat cttcccgcca tctgatgagc agttgaaatc tggaactgcc     420
tctgttgtgt gcctgctgaa taacttctat cccagagagg ccaaagtaca gtggaaggtg     480
gataacgccc tccaatcggg taactcccag gagagtgtca cagagcagga cagcaaggac     540
agcacctaca gcctcagcag caccctgacg ctgagcaaag cagactacga gaaacacaaa     600
gtctacgcct gcgaagtcac ccatcagggc ctgagctcgc ccgtcacaaa gagcttcaac     660
aggggagagt gttaattcta gataattaat taggaggaat ttaaaatgaa atacctattg     720
cctacggcag ccgctggatt gttattactc gctgcccaac cagccatggc cgaagt         776
```

<210> SEQ ID NO 16
<211> LENGTH: 761
<212> TYPE: DNA
<213> ORGANISM: Homo sapiens

<400> SEQUENCE: 16

```
actcgctgcc aaccagccat ggctcaagtg cagctggtgc agtctggggc tgaggtgaag      60
aagcctgggg cctcagtgaa ggtttcctgc aaggcatctg gatacacctt caccagctac     120
tatatgcact gggtgcgaca ggcccctgga caagggcttg agtggatggg aataatcaac     180
cctagtggtg gtagcacaag ctacgcacag aagttccagg gcagagtcac catgaccagg     240
gacacgtcca cgagcacagt ctacatggag ctgagcaggc tgagatctga cgacacggcc     300
gtgtattact gtgcgagaga tgtgcagtgg ctggcatacg gtatggacgt ctggggccaa     360
gggaccacgg tcaccgtctc ctcagcctcc accaagggcc catcggtctt ccccctggca     420
ccctcctcca agagcacctc tgggggcaca gcggccctgg gctgcctggt caaggactac     480
ttccccgaac cggtgacggt gtcgtggaac tcaggcgccc tgaccagcgg cgtgcacacc     540
ttcccggctg tcctacagtc ctcaggactc tactccctca gcagcgtggt gaccgtgccc     600
tccagcagct tgggcaccca gacctacatc tgcaacgtga atcacaagcc cagcaacacc     660
aaggtggaca agaaagttga gcccaaatct tgtgacaaaa ctagtggcca ggccggccac     720
caccaccacc accacggcga ctacaaggac gatgacgata a                          761
```

<210> SEQ ID NO 17
<211> LENGTH: 715
<212> TYPE: DNA
<213> ORGANISM: Homo sapiens

<400> SEQUENCE: 17

```
taactcagcc accctcggtg tcagtgaccc caggacagac ggccaggatc acctgctctg      60
gagatgcatt gccaaagcac tttgcttatt ggtaccaaca gaagccaggc caggcccctg     120
tattgataat atataaagac actgagaggc cctcagggat ccctgagcga ttctctggct     180
ccaactctgg gaacacggcc accctgacca ttagcagggt cgaagccggg gatgaggccg     240
```

-continued

```
actattactg tcaggtgtgg gatagtagta gtggttgggt gttcggcgga gggaccaagc    300
tgaccgtcca aggtcagccc aaggctgccc cctcggtcac tctgttccca ccctcctctg    360
aggagcttca agccaacaag gccacactgg tgtgtctcat aagtgacttc tacccgggag    420
ccgtgacagt ggcctggaag gcagatagca gccccgtcaa ggcgggagtg gagaccacca    480
caccctccaa acaaagcaac aacaagtacg cggccagcag ctacctgagc ctgacgcctg    540
agcagtggaa gtcccacaaa agctacagct gccaggtcac gcatgaaggg agcaccgtgg    600
agaagacagt ggcccctaca gaatgttcat aattctagat aattaattag gaggaattta    660
aaatgaaata cctattgcct acggcagccg ctggattgtt attactcgct gccca         715
```

<210> SEQ ID NO 18
<211> LENGTH: 724
<212> TYPE: DNA
<213> ORGANISM: Homo sapiens

<400> SEQUENCE: 18

```
aggtactggt gaagccctcg cagaccctct cactcacctg tgccatctcc ggggacagtg     60
tctctagcaa cagtgctgct tggaactgga tcaggcagtc cccatcgaga ggccttgagt    120
ggctgggaag gacatactac aggtccaagt ggtataatga ttatgcagta tctgtgaaaa    180
gtcgaataac catcaaccca gacacatcca agaaccagtt ctccctgcag ctgaactctg    240
tgactcccga ggacacggct gtgtattact gtgcaagaga aaggggggata ggtcggggta    300 taactggaac tacaattccg tacaactggt tcgaccctg gggccaggga accctggtca    360
ccgtctcttc agcctccacc aagggcccat cggtcttccc cctggcaccc tcctccaaga    420
gcacctctgg gggcacagcg gccctgggct gcctggtcaa ggactacttc cccgaaccgg    480
tgacggtgtc gtggaactca ggcgccctga ccagcggcgt gcacaccttc ccggctgtcc    540
tacagtcctc aggactctac tccctcagca gcgtggtgac cgtgccctcc agcagcttgg    600
gcacccagac ctacatctgc aacgtgaatc acaagcccag caacaccaag gtggacaaga    660
aagttgagcc caaatcttgt gacaaaacta gtggccaggc cggccaccac caccaccacc    720
acgg                                                                 724
```

HUMAN MONOCLONAL ANTIBODIES THAT SPECIFICALLY BIND IGF-II

CROSS REFERENCE TO RELATED APPLICATIONS

This is the U.S. National Stage of International Application No. PCT/US2006/031814, filed Aug. 15, 2006, which was published in English under PCT Article 21(2), which in turn claims the benefit of U.S. Provisional Application No. 60/709,226, filed Aug. 17, 2005, and U.S. Provisional Application No. 60/798,817, filed May 8, 2006, which are both incorporated herein by reference.

FIELD OF THE DISCLOSURE

This application relates to the field of antibodies, specifically to human antibodies that specifically bind insulin-like growth factor II (IGF-II) and their use.

BACKGROUND

The insulin-like growth factor (IGF) system includes the insulin-like growth factors I and II (IGF-I and IGF-II), insulin, insulin receptor (IR), insulin-like growth factor receptors I and II (IGF-IR and IGF-IIR) and IGF-II/M6PR), insulin-like growth factor binding proteins (IGFBP-1 to -6), and IGFBP-related proteins (IGFBP-rPs). A schematic of this system is set forth in FIG. 1. The IGF system plays a key role in regulating both normal and pathogenic cellular growth and function.

Unlike insulin, the IGFs are produced by almost every cell in the body, although IGF-II is predominantly produced in the liver (Oh, Cancer Epidemiol Biomarkers Prev 13:748-752, 2004). In rodents, IGF-I is primarily expressed at adulthood, while IGF-II is mainly expressed prenatally. In humans, both IGFs are produced at all stages of life. High circulating levels of IGFs have been correlated with increased risk of several cancers (Peyrat et al., Eur J Cancer 29A:492-497, 1993; Chan et al., Science 279:563-566, 1998; Hankinson et al., Lancet 351:1393-1396, 1998; Wolk et al., J Natl Cancer Inst 90:911-9151998; Ma et al., J Natl Cancer Inst 91:620-625, 1999).

There are six IGFBPs, each of which binds to IGF-I and IGF-II with varying affinities. For example, IGFBP-5 and -6 bind to IGF-II with a 10-fold higher affinity than IGF-I. IGFBPs increase the half-life of circulating IGFs, and control their availability for receptor binding. IGFBP-3, the predominant IGFBP in serum, has been shown to suppress the mitogenic effect of IGF-I, and high levels of IGFBP-3 are inversely related to cancer risk (Oh et al., supra, 2004).

Recently, a number of epidemiologic studies have shown that high circulating levels of IGF-1 are associated with an increased risk for cancer, including breast, prostate, lung and colorectal cancer. IGF-1 stimulates cell proliferation and inhibits apoptosis; a combination of these effects have been shown to have a profound impact on tumor growth (reviewed in Yu and Rhan, J. Natl. Canc. Inst. 18: 1472-1849, 2000). Antibodies developed against IGF-IR have been shown to inhibit cancer cell proliferation and induce receptor degradation in tumor cells. However, there is still a need for human antibodies that bind IGF-II that can be used to detect IGF-II and can be used in treatment methods.

SUMMARY OF THE DISCLOSURE

Disclosed herein are isolated monoclonal human antibodies that specifically bind human insulin-like growth factor II (IGF-II) with an equilibrium dissociation constant ($K_d$) of 1 mM or less wherein the antibody bind IGF-I with an equilibrium dissociation constant ($K_d$) of 1 mM or higher. The antibodies inhibit phosphorylation of the insulin-like growth factor receptor. Compositions including these antibodies are also provided.

In several embodiments, nucleic acids encoding these antibodies, expression vectors including these nucleic acids, and isolated host cells that express the nucleic acids are also disclosed.

In one embodiment, methods are disclosed for detecting human IGF-II in a sample. The method includes contacting the sample with isolated monoclonal human antibodies that specifically binds insulin-like growth factor II (IGF-II) with an equilibrium association constant ($K_d$) of 1 nM or less, wherein the antibody bind IGF-I with an equilibrium association constant ($K_d$) of 1 mM or greater to form an immune complex, and detecting the immune complex.

In other embodiments, methods are disclosed for detecting a tumor in a subject, or for determining the prognosis of the tumor in the subject. The methods include the use of an isolated monoclonal human antibody that specifically binds insulin-like growth factor II (IGF-II) with an equilibrium association constant ($K_d$) of 1 nM or less, thereby detecting the presence of the tumor in the subject.

In a further embodiment, methods are disclosed for treating a subject with a tumor. The methods include administering to the subject a therapeutically effective amount of an isolated monoclonal human antibody that specifically binds insulin-like growth factor II (IGF-II) with an equilibrium association constant ($K_d$) of 1 nM or less.

The foregoing and other features and advantages of the invention will become more apparent from the following detailed description of a several embodiments which proceeds with reference to the accompanying figures.

BRIEF DESCRIPTION OF THE FIGURES

FIG. 3A is a graph showing ELISA binding of Fab M606 on immobilized long IGF-II. Fab m610 and m616 have similar binding kinetics. The Inset shows an SDS gel with purified Fabs. The binding of the Fabs was measured by using ELISA and Biacore surface plasmon resonance technology. In an ELISA assay the EC50 for these antibodies was approximately 4 nM. FIG. 3B is a bar graph. Fabs were tested for specificity by ELISA with different proteins immobilized on plates. The three Fabs bound to pro-IGF-II and to the mature form of IGF-II, but not to insulin and IGF-I. The binding to pro-IGF-II was slightly better than to IGF-II. FIG. 3C is a set of line graphs showing the binding kinetics of Fab m606 and m610 as measured by Biacore for different concentrations of the antibodies represented with different lines. Interactions between various Fabs and IGF-II were analyzed by surface plasmon resonance technology using a BIACORE 1000 instrument (Biacore, Pharmacia, Piscataway, N.J.). IGF-II was covalently immobilized onto a sensor chip (CM5) using carbodiimide coupling chemistry. A control reference surface was prepared for nonspecific binding and refractive index changes. For analysis of the kinetics of interactions, varying concentrations of Fabs were injected at flow rate of 30 µl/min using running buffer containing 150 mM NaCl, 3 mM EDTA, and 0.005% P-20 (pH 7.4). The association and dissociation phase data were fitted simultaneously to a 1:1 Langumir global model by using the nonlinear data analysis program BIAevaluation 3.2. All the experiments were performed at 25° C. In these studies, $K_{on}$=3.5 and $2.9 \times 10^5 M^{-1}S^{-1}$; $K_{off}$=2.5 and $2.6 \times 10^{-4} S^{-1}$, and $K_D$=0.7 and 0.9 nM. Further experiments by using Biacore showed that the two Fabs compete between each other for binding to pro-IGF-II, suggesting that they may have overlapping epitopes.

FIG. 5A is a digital image. MCF-7 cells in serum free medium were pre-incubated with indicated concentrations of Fab m610 for 30 min. Ten ng of IGF-II was added, and 20 min later cells were collected. Equal amount of cell lysates were used for immunoprecipitation with anti-IGF-IR beta antibody (Santa cruz). Phosphorylated IGF-IR was detected with mAb 4G10 specific to phosphor-tyrosine. FIG. 5B is a graph. A similar test with IgG m610 was performed with the same procedure in FIG. 5A. The intensity of phospho-IGF-IR was quantified by phosphor-imager and plotted. FIG. 5C is a digital image. Phosphorylation of IGF-IR and insulin receptor (IR) was monitored in MCF-7 cells treated with IGF-II alone (lane 2) or with indicated concentrations of IgG m610. In lanes 3 and 4 cells were preincubated with the antibody for 30 min before addition of IGF-II. In lanes 5 and 6, cells were treated with the antibody and IGF-II at the same time. Bottom panels show the total amount of receptors in the immunopreciptates.

FIG. 7 is a digital image showing IgG M610 prevented activation of signals down stream of IGF-IR induced by IGF-II. MCF-7 cells were incubated with different doses of IgG m610, and incubated with 10 nM IGF-II. Cell lysates were made 20 minutes after addition of IGF-II. Western blots were performed with antibodies recognizing phosphor-Akt, phosphor-MAPK and total MAPK.

SEQUENCE LISTING

Figure 1:
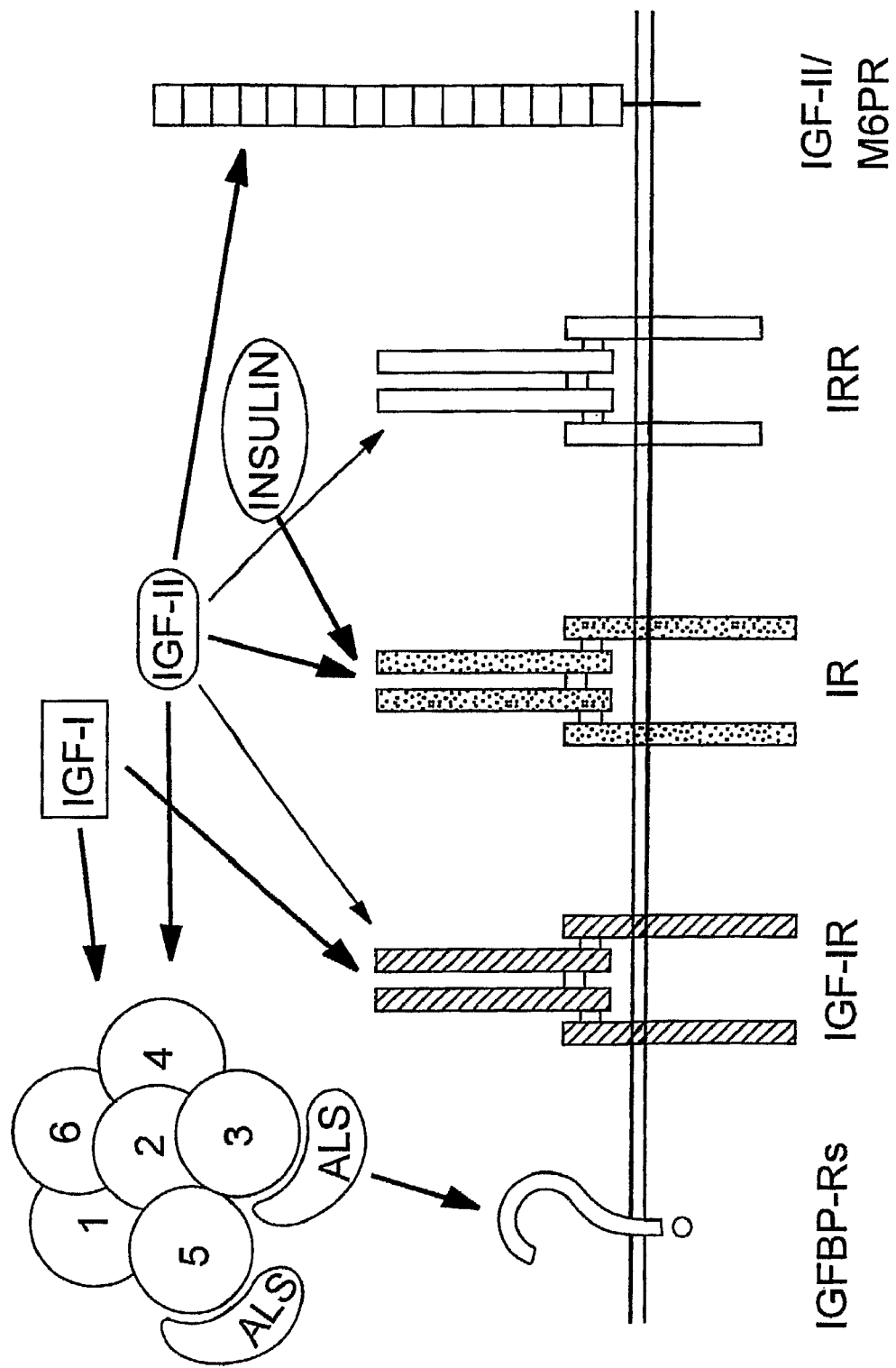
FIG. 1 is a schematic representation of insulin-like growth factor system. Represented are IGFBPs 1-6, IGF-I, IGF-II, IGF-IR, and IGF-II/M6PR. Also represented are insulin, the insulin receptor (IR), and the insulin receptor-related receptor (IRR).

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand.

SEQ ID NO: 1 is an exemplary amino acid sequence of a human insulin chain A.
SEQ ID NO: 2 is an exemplary amino acid sequence of a human insulin chain B.
SEQ ID NO: 3 is an exemplary amino acid sequence of an IGF-I precursor.
SEQ ID NO: 4 is an exemplary amino acid sequence of a mature IGF-I.
SEQ ID NO: 5 is an exemplary amino acid sequence of an IGF-II precursor.
SEQ ID NO: 6 is an exemplary amino acid sequence of a mature IGF-II.
SEQ ID NO: 7 is the amino acid sequence of human monoclonal antibody clone M606 light chain.
SEQ ID NO: 8 is the amino acid sequence of human monoclonal antibody clone M610 light chain.
SEQ ID NO: 9 is the amino acid sequence of human monoclonal antibody clone M616 light chain.
SEQ ID NO: 10 is the amino acid sequence of human monoclonal antibody clone M606 heavy chain.
SEQ ID NO: 11 is the amino acid sequence of human monoclonal antibody clone M610 heavy chain.
SEQ ID NO: 12 is the amino acid sequence of human monoclonal antibody clone M616 heavy chain.
SEQ ID NO: 13 is an exemplary nucleotide sequence of Fab m606 light chain.
SEQ ID NO: 14 is an exemplary nucleotide sequence of Fab m606 heavy chain.
SEQ ID NO: 15 is an exemplary nucleotide sequence of Fab m610 light chain.
SEQ ID NO: 16 is an exemplary nucleotide sequence of Fab m610 heavy chain.
SEQ ID NO: 17 is an exemplary nucleotide sequence of Fab m616 light chain.
SEQ ID NO: 18 is an exemplary nucleotide sequence of Fab m616 heavy chain.

DETAILED DESCRIPTION OF SEVERAL EMBODIMENTS

I. Abbreviations
  BSA: bovine serum albumin
  CDR: complementarity determining region
  dsFv: disulfide stabilized fragment of a variable region
  DMEM: Dulbecco's modified eagle medium
  ELISA: enzyme-linked immunosorbent assay
  EM: effector molecule
  ERK: extra-cellular signal response kinase
  FACS: fluorescence activated cell sorting
  FBS: fetal bovine serum
  FITC: fluoroscein istothiocyanate HEPES: 4-(2-hydroxyethyl)-1-piperazineethanesulfonic acid
IGF-I: insulin-like growth factor I
IGF-IR: insulin-like growth factor I receptor
IGF-II: insulin-like growth factor II
IGFBP: insulin-like growth factor binding proteins
IGFBP-rP: IGFBP-related proteins
IPTG: isopropyl-beta-D-thiogalactopyranoside
HCDR: heavy chain complementarity determining region
HAMA: human anti-murine antibody
HAT: hypoxanthine aminopterin thymidine
IL-6: interleukin-6
Ig: immunoglobulin
IR: insulin receptor
IRR: insulin receptor-related receptor
kDa: kilodaltons
LCDR: light chain complementarity determining region
MAb: monoclonal antibody
MAPK: mitogen-activated protein kinase
MMP: matrix-metalloproteinase
PBS: phosphate buffered saline
scFv: single chain fragment of a variable region
SDR: specificity determining residues
SDS-PAGE: sodium dodecyl (lauryl) sulfate-polyacrylamide gel electrophoreses
RIA: radioimmunoassay
$V_H$: variable region of a heavy chain
$V_L$: variable region of a light chain II. Terms Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

Administration: The introduction of a composition into a subject by a chosen route. For example, if the chosen route is intravenous, the composition is administered by introducing the composition into a vein of the subject.

Amplification: Of a nucleic acid molecule (such as, a DNA or RNA molecule) refers to use of a technique that increases the number of copies of a nucleic acid molecule in a specimen. An example of amplification is the polymerase chain reaction, in which a biological sample collected from a subject is contacted with a pair of oligonucleotide primers, under conditions that allow for the hybridization of the primers to a nucleic acid template in the sample. The primers are extended under suitable conditions, dissociated from the template, and then re-annealed, extended, and dissociated to amplify the number of copies of the nucleic acid. The product of amplification may be characterized by electrophoresis, restriction endonuclease cleavage patterns, oligonucleotide hybridization or ligation, and/or nucleic acid sequencing using standard techniques. Other examples of amplification include strand displacement amplification, as disclosed in U.S. Pat. No. 5,744,311; transcription-free isothermal amplification, as disclosed in U.S. Pat. No. 6,033,881; repair chain reaction amplification, as disclosed in WO 90/01069; ligase chain reaction amplification, as disclosed in EP-A-320 308; gap filling ligase chain reaction amplification, as disclosed in U.S. Pat. No. 5,427,930; and NASBA™ RNA transcription-free amplification, as disclosed in U.S. Pat. No. 6,025,134.

Animal: Living multi-cellular vertebrate organisms, a category that includes, for example, mammals and birds. The term mammal includes both human and non-human mammals. Similarly, the term "subject" includes both human and veterinary subjects.

Antibody: A polypeptide ligand comprising at least a light chain or heavy chain immunoglobulin variable region which specifically recognizes and binds an epitope of an antigen, such as insulin-like growth factor II (IGF-ID) or a fragment thereof. Antibodies are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody.

This includes intact immunoglobulins and the variants and portions of them well known in the art, such as Fab' fragments, F(ab)'$_2$ fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (for example, humanized murine antibodies), heteroconjugate antibodies (such as, bispecific antibodies). See also, *Pierce Catalog and Handbook*, 1994-1995 (Pierce Chemical Co., Rockford, Ill.); Kuby, J., *Immunology*, 3rd Ed., W.H. Freeman & Co., New York, 1997.

Typically, a naturally occurring immunoglobulin has heavy (H) chains and light (L) chains interconnected by disulfide bonds. There are two types of light chain, lambda (λ) and kappa (k). There are five main heavy chain classes (or isotypes) which determine the functional activity of an antibody molecule: IgM, IgD, IgG, IgA and IgE.

Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs." The extent of the framework region and CDRs have been defined (see, Kabat et al., *Sequences of Proteins of Immunological Interest*, U.S. Department of Health and Human Services, 1991, which is hereby incorporated by reference). The Kabat database is now maintained online. The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. An antibody that binds IGF-II will have a specific $V_H$ region and the $V_L$ region sequence, and thus specific CDR sequences. Antibodies with different specificities (i.e. different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

References to "$V_H$" or "VH" refer to the variable region of an immunoglobulin heavy chain, including that of an Fv, scFv, dsFv or Fab. References to "$V_L$" or "VL" refer to the variable region of an immunoglobulin light chain, including that of an Fv, scFv, dsFv or Fab.

A "monoclonal antibody" is an antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

A "chimeric antibody" has framework residues from one species, such as human, and CDRs (which generally confer antigen binding) from another species, such as a murine antibody that specifically binds IGF-II.

A "human" antibody (also called a "fully human" antibody) is an antibody that includes human framework regions and all of the CDRs from a human immunoglobulin. In one example, the framework and the CDRs are from the same originating human heavy and/or light chain amino acid sequence. However, frameworks from one human antibody can be engineered to include CDRs from a different human antibody. A "humanized" immunoglobulin is an immunoglobulin including a human framework region and one or more CDRs from a non-human (for example a mouse, rat, or synthetic) immunoglobulin. The non-human immunoglobulin providing the CDRs is termed a "donor," and the human immunoglobulin providing the framework is termed an "acceptor." In one embodiment, all the CDRs are from the donor immunoglobulin in a humanized immunoglobulin. Constant regions need not be present, but if they are, they must be substantially identical to human immunoglobulin constant regions, i.e., at least about 85-90%, such as about 95% or more identical. Hence, all parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Humanized immunoglobulins can be constructed by means of genetic engineering (see for example, U.S. Pat. No. 5,585, 089).

Binding affinity: Affinity of an antibody for an antigen, such as IGF-II. In one embodiment, affinity is calculated by a modification of the Scatchard method described by Frankel et al., *Mol. Immunol.*, 16:101-106, 1979. In another embodiment, binding affinity is measured by an antigen/antibody dissociation rate. In yet another embodiment, a high binding affinity is measured by a competition radioimmunoassay. In several examples, a high binding affinity is at least about $1 \times 10^{-8}$ M. In other embodiments, a high binding affinity is at least about $1.5 \times 10^{-8}$, at least about $2.0 \times 10^{-8}$, at least about $2.5 \times 10^{-8}$, at least about $3.0 \times 10^{-8}$, at least about $3.5 \times 10^{-8}$, at least about $4.0 \times 10^{-8}$, at least about $4.5 \times 10^{-8}$, or at least about $5.0 \times 10^{-8}$ M.

Chemotherapeutic agents: Any chemical agent with therapeutic usefulness in the treatment of diseases characterized by abnormal cell growth. Such diseases include tumors, neoplasms, and cancer as well as diseases characterized by hyperplastic growth such as psoriasis. In one embodiment, a chemotherapeutic agent is an agent of use in treating a lymphoma, leukemia, or another tumor. In one embodiment, a chemotherapeutic agent is a radioactive compound. One of skill in the art can readily identify a chemotherapeutic agent of use (see for example, Slapak and Kufe, Principles of *Cancer Therapy*, Chapter 86 in Harrison's Principles of Internal Medicine, 14th edition; Perry et al., Chemotherapy, Ch. 17 in Abeloff, Clinical Oncology $2^{nd}$ ed., (2000 Churchill Livingstone, Inc; Baltzer, L., Berkery, R. (eds): *Oncology Pocket Guide to Chemotherapy*, 2nd ed. St. Louis, Mosby-Year Book, 1995; Fischer, D. S., Knobf, M. F., Durivage, H. J. (eds): *The Cancer Chemotherapy Handbook*, 4th ed. St. Louis, Mosby-Year Book, 1993). Combination chemotherapy is the administration of more than one agent to treat cancer. One example is the administration of an antibody that binds IGF-II or a fragment thereof used in combination with a radioactive or chemical compound.

Chimeric antibody: An antibody that includes sequences derived from two different antibodies, which typically are of different species. Most typically, chimeric antibodies include human and murine antibody domains, generally human constant regions and murine variable regions, murine CDRs and/or murine SDRs.

Conservative variants: "Conservative" amino acid substitutions are those substitutions that do not substantially affect or decrease the affinity of an antibody to IGF-II. For example, a human antibody that specifically binds IGF-II can include at most about 1, at most about 2, at most about 5, and most about 10, or at most about conservative substitutions and specifically bind the original IGF-II polypeptide. The term conservative variation also includes the use of a substituted amino acid in place of an unsubstituted parent amino acid, provided that antibody specifically binds IGF-II. Non-conservative substitutions are those that reduce an activity or binding to IGF-II.

Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Complementarity Determining Region (CDR): Amino acid sequences which together define the binding affinity and specificity of the natural Fv region of a native Ig binding site. The light and heavy chains of an Ig each have three CDRs, designated L-CDR1, L-CDR2, L-CDR3 and H-CDR1, H-CDR2, H-CDR3, respectively. By definition, the CDRs of the light chain are bounded by the residues at positions 24 and 34 (L-CDR1), 50 and 56 (L-CDR2), 89 and 97 (L-CDR3); the CDRs of the heavy chain are bounded by the residues at positions 31 and 35b (H-CDR1), 50 and 65 (H-CDR2), 95 and 102 (H-CDR3), using the numbering convention delineated by Kabat et al., (1991) *Sequences of Proteins of Immunologi-*

*cal Interest*, 5<sup>th</sup> Edition, U.S. Department of Health and Human Services, Public Health Service, National Institutes of Health, Bethesda, Md. (NIH Publication No. 91-3242).

Contacting: Placement in direct physical association; includes both in solid and liquid form.

Cytotoxicity: The toxicity of a molecule, such as an immunotoxin, to the cells intended to be targeted, as opposed to the cells of the rest of an organism. In one embodiment, in contrast, the term "toxicity" refers to toxicity of an immunotoxin to cells other than those that are the cells intended to be targeted by the targeting moiety of the immunotoxin, and the term "animal toxicity" refers to toxicity of the immunotoxin to an animal by toxicity of the immunotoxin to cells other than those intended to be targeted by the immunotoxin.

Degenerate variant: A polynucleotide encoding an IGF-II polypeptide or an antibody that binds IGF-II that includes a sequence that is degenerate as a result of the genetic code. There are 20 natural amino acids, most of which are specified by more than one codon. Therefore, all degenerate nucleotide sequences are included as long as the amino acid sequence of the IGF-II polypeptide or antibody that binds IGF-II encoded by the nucleotide sequence is unchanged.

Effector molecule: The portion of a chimeric molecule that is intended to have a desired effect on a cell to which the chimeric molecule is targeted. Effector molecule is also known as an effector moiety (EM), therapeutic agent, or diagnostic agent, or similar terms.

Therapeutic agents include such compounds as nucleic acids, proteins, peptides, amino acids or derivatives, glycoproteins, radioisotopes, lipids, carbohydrates, or recombinant viruses. Nucleic acid therapeutic and diagnostic moieties include antisense nucleic acids, derivatized oligonucleotides for covalent cross-linking with single or duplex DNA, and triplex forming oligonucleotides. Alternatively, the molecule linked to a targeting moiety, such as an anti-IGF-II antibody, may be an encapsulation system, such as a liposome or micelle that contains a therapeutic composition such as a drug, a nucleic acid (such as an antisense nucleic acid), or another therapeutic moiety that can be shielded from direct exposure to the circulatory system. Means of preparing liposomes attached to antibodies are well known to those of skill in the art. See, for example, U.S. Pat. No. 4,957,735; and Connor et al., *Pharm. Ther.* 28:341-365, 1985. Diagnostic agents or moieties include radioisotopes and other detectable labels. Detectable labels useful for such purposes are also well known in the art, and include radioactive isotopes such as $^{32}P$, $^{125}I$, and $^{131}I$, fluorophores, chemiluminescent agents, and enzymes.

Epitope: An antigenic determinant. These are particular chemical groups or peptide sequences on a molecule that are antigenic, i.e. that elicit a specific immune response. An antibody specifically binds a particular antigenic epitope on a polypeptide.

Expressed: Translation of a nucleic acid into a protein. Proteins may be expressed and remain intracellular, become a component of the cell surface membrane, or be secreted into the extracellular matrix or medium.

Expression Control Sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (i.e., ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see for example, Bitter et al., *Methods in Enzymology* 153:516-544, 1987). For example, when cloning in bacterial systems, inducible promoters such as pL of bacteriophage lambda, plac, ptrp, ptac (ptrp-lac hybrid promoter) and the like may be used. In one embodiment, when cloning in mammalian cell systems, promoters derived from the genome of mammalian cells (such as metallothionein promoter) or from mammalian viruses (such as the retrovirus long terminal repeat; the adenovirus late promoter; the vaccinia virus 7.5K promoter) can be used. Promoters produced by recombinant DNA or synthetic techniques may also be used to provide for transcription of the nucleic acid sequences.

Framework Region: Amino acid sequences interposed between CDRs. Includes variable light and variable heavy framework regions. The framework regions serve to hold the CDRs in an appropriate orientation for antigen binding.

HAMA (Human anti-murine antibody) response: An immune response in a human subject to the variable and constant regions of a murine antibody that has been administered to the patient. Repeated antibody administration may lead to an increased rate of clearance of the antibody from the patient's serum and may also elicit allergic reactions in the patient.

Host cells: Cells in which a vector can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

Immune response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a CD4+ response or a CD8+ response. In another embodiment, the response is a B cell response, and results in the production of specific antibodies.

Immunoconjugate: A covalent linkage of an effector molecule to an antibody. The effector molecule can be a detectable label or an immunotoxin. Specific, non-limiting examples of toxins include, but are not limited to, abrin, ricin, *Pseudomonas* exotoxin (PE, such as PE35, PE37, PE38, and PE40), diphtheria toxin (DT), botulinum toxin, or modified toxins thereof, or other toxic agents that directly or indirectly inhibit cell growth or kill cells. For example, PE and DT are highly toxic compounds that typically bring about death through liver toxicity. PE and DT, however, can be modified into a form for use as an immunotoxin by removing the native targeting component of the toxin (such as the domain Ia of PE and the B chain of DT) and replacing it with a different targeting moiety, such as an antibody. A "chimeric molecule" is a targeting moiety, such as a ligand or an antibody, conjugated (coupled) to an effector molecule. The term "conjugated" or "linked" refers to making two polypeptides into one contiguous polypeptide molecule. In one embodiment, an antibody is joined to an effector molecule (EM). In another embodiment, an antibody joined to an effector molecule is further joined to a lipid or other molecule to a protein or peptide to increase its half-life in the body. The linkage can be either by chemical or recombinant means. In one embodiment, the linkage is chemical, wherein a reaction between the antibody moiety and the effector molecule has produced a covalent bond formed between the two molecules to form one molecule. A peptide linker (short peptide sequence) can optionally be included between the antibody and the effector molecule. Because immunoconjugates were originally prepared from two molecules with separate functionalities, such as an antibody and an effector molecule, they are also sometimes referred to as "chimeric molecules." The term "chimeric molecule," as used herein, therefore refers to a targeting moiety, such as a ligand or an antibody, conjugated (coupled) to an effector molecule.

Immunogenic peptide: A peptide which comprises an allele-specific motif or other sequence, such as an N-terminal repeat, such that the peptide will bind an MHC molecule and induce a cytotoxic T lymphocyte ("CTL") response, or a B cell response (e.g. antibody production) against the antigen from which the immunogenic peptide is derived.

In one embodiment, immunogenic peptides are identified using sequence motifs or other methods, such as neural net or polynomial determinations, known in the art. Typically, algorithms are used to determine the "binding threshold" of peptides to select those with scores that give them a high probability of binding at a certain affinity and will be immunogenic. The algorithms are based either on the effects on MHC binding of a particular amino acid at a particular position, the effects on antibody binding of a particular amino acid at a particular position, or the effects on binding of a particular substitution in a motif-containing peptide. Within the context of an immunogenic peptide, a "conserved residue" is one which appears in a significantly higher frequency than would be expected by random distribution at a particular position in a peptide. In one embodiment, a conserved residue is one where the MHC structure may provide a contact point with the immunogenic peptide. In one specific non-limiting example, an immunogenic polypeptide includes a region of IGF-II, or a fragment thereof, wherein the polypeptide that is expressed on the cell surface of a host cell that expresses the full-length IGF-II polypeptide.

Immunogenic composition: A composition comprising an IGF-II polypeptide that induces a measurable CTL response against cells expressing IGF-II polypeptide, or induces a measurable B cell response (such as production of antibodies) against an IGF-II polypeptide. It further refers to isolated nucleic acids encoding a IGF-II polypeptide that can be used to express the IGF-II polypeptide (and thus be used to elicit an immune response against this polypeptide). For in vitro use, an immunogenic composition may consist of the isolated protein or peptide epitope. For in vivo use, the immunogenic composition will typically comprise the protein or immunogenic peptide in pharmaceutically acceptable carriers, and/or other agents. Any particular peptide, such as a IGF-II polypeptide, or nucleic acid encoding the polypeptide, can be readily tested for its ability to induce a CTL or B cell response by art-recognized assays. Immunogenic compositions can include adjuvants, which are well known to one of skill in the art.

Immunologically reactive conditions: Includes reference to conditions which allow an antibody raised against a particular epitope to bind to that epitope to a detectably greater degree than, and/or to the substantial exclusion of, binding to substantially all other epitopes. Immunologically reactive conditions are dependent upon the format of the antibody binding reaction and typically are those utilized in immunoassay protocols or those conditions encountered in vivo. See Harlow & Lane, supra, for a description of immunoassay formats and conditions. The immunologically reactive conditions employed in the methods are "physiological conditions" which include reference to conditions (such as temperature, osmolarity, pH) that are typical inside a living mammal or a mammalian cell. While it is recognized that some organs are subject to extreme conditions, the intra-organismal and intracellular environment normally lies around pH 7 (i.e., from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

Immunotherapy: A method of evoking an immune response against cancer cells based on their production of target antigens. Immunotherapy based on cell-mediated immune responses involves generating a cell-mediated response to cells that produce particular antigenic determinants, while immunotherapy based on humoral immune responses involves generating specific antibodies to cells that produce particular antigenic determinants.

Inhibiting or treating a disease: Inhibiting the full development of a disease or condition, for example, in a subject who is at risk for a disease such as a tumor (for example, a cancer such as a leukemia or a carcinoma). "Treatment" refers to a therapeutic intervention that ameliorates a sign or symptom of a disease or pathological condition after it has begun to develop. As used herein, the term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of metastases, an improvement in the overall health or well-being of the subject, or by other parameters well known in the art that are specific to the particular disease. A "prophylactic" treatment is a treatment administered to a subject who does not exhibit signs of a disease or exhibits only early signs for the purpose of decreasing the risk of developing pathology.

Isolated: An "isolated" biological component (such as a nucleic acid, protein or organelle) has been substantially separated or purified away from other biological components in the cell of the organism in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Label: A detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes. In one example, a "labeled antibody" refers to incorporation of another molecule in the antibody. For example, the label is a detectable marker, such as the incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionuclides (such as $^{35}$S or 131I), fluorescent labels (such as fluoroscein istothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance.

Ligand: Any molecule which specifically binds a IGF-II protein and includes, inter alia, antibodies that specifically bind a IGF-II protein. In alternative embodiments, the ligand is a protein or a small molecule (one with a molecular weight less than 6 kiloDaltons).

Linker peptide: A peptide within an antibody binding fragment (such as an Fv fragment) which serves to indirectly bond the variable heavy chain to the variable light chain. "Linker" can also refer to a peptide serving to link a targeting moiety, such as a scFv, to an effector molecule, such as a cytotoxin or a detectable label.

The terms "conjugating," "joining," "bonding" or "linking" refer to making two polypeptides into one contiguous polypeptide molecule, or to covalently attaching a radionuclide or other molecule to a polypeptide, such as an scFv. In the specific context, the terms include reference to joining a ligand, such as an antibody moiety, to an effector molecule ("EM"). The linkage can be either by chemical or recombinant means. "Chemical means" refers to a reaction between the antibody moiety and the effector molecule such that there is a covalent bond formed between the two molecules to form one molecule.

Lymphocytes: A type of white blood cell that is involved in the immune defenses of the body. There are two main types of lymphocytes: B cells and T cells.

Mammal: This term includes both human and non-human mammals. Similarly, the term "subject" includes both human and veterinary subjects.

Major Histocompatibility Complex or MHC: Generic designation meant to encompass the histocompatibility antigen systems described in different species, including the human leukocyte antigens ("HLA"). The term "motif" refers to the pattern of residues in a peptide of defined length, usually about 8 to about 11 amino acids, which is recognized by a particular MHC allele. The peptide motifs are typically different for each MHC allele and differ in the pattern of the highly conserved residues and negative binding residues.

Neoplasia and Tumor: The process of abnormal and uncontrolled growth of cells. Neoplasia is one example of a proliferative disorder. The product of neoplasia is a neoplasm (a tumor), which is an abnormal growth of tissue that results from excessive cell division. The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant." Examples of hematological tumors include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Examples of solid tumors, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma).

In several examples a tumor is a sarcoma, leukemia, prostate cancer, lung cancer, breast cancer, lung cancer, colon cancer, stomach cancer, uterine cancer, cervical cancer, esophageal cancer, liver cancer, pancreatic cancer, kidney cancer, thyroid cancer, brain cancer, or an ovarian cancer Nucleic acid: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs), and the like. Such polynucleotides can be synthesized, for example, using an automated DNA synthesizer. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

"cDNA" refers to a DNA that is complementary or identical to an mRNA, in either single stranded or double stranded form.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system.

Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Recombinant nucleic acid" refers to a nucleic acid having nucleotide sequences that are not naturally joined together. This includes nucleic acid vectors comprising an amplified or assembled nucleic acid which can be used to transform a suitable host cell. A host cell that comprises the recombinant nucleic acid is referred to as a "recombinant host cell." The gene is then expressed in the recombinant host cell to produce, such as a "recombinant polypeptide." A recombinant nucleic acid may serve a non-coding function (such as a promoter, origin of replication, ribosome-binding site, etc.) as well.

A first sequence is an "antisense" with respect to a second sequence if a polynucleotide whose sequence is the first sequence specifically hybridizes with a polynucleotide whose sequence is the second sequence.

Terms used to describe sequence relationships between two or more nucleotide sequences or amino acid sequences include "reference sequence," "selected from," "comparison window," "identical," "percentage of sequence identity," "substantially identical," "complementary," and "substantially complementary."

For sequence comparison of nucleic acid sequences, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are used. Methods of alignment of sequences for comparison are well known in the art. Optimal alignment of sequences for comparison can be conducted, for example, by the local homology algorithm of Smith & Waterman, *Adv. Appl. Math.* 2:482, 1981, by the homology alignment algorithm of Needleman & Wunsch, *J. Mol. Biol.* 48:443, 1970, by the search for similarity method of Pearson & Lipman, *Proc. Nat'l. Acad. Sci. USA* 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see for example, *Current Protocols in Molecular Biology* (Ausubel et al., eds 1995 supplement)).

One example of a useful algorithm is PILEUP. PILEUP uses a simplification of the progressive alignment method of Feng & Doolittle, *J. Mol. Evol.* 35:351-360, 1987. The method used is similar to the method described by Higgins & Sharp, CABIOS 5:151-153, 1989. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, such as version 7.0 (Devereaux et al., *Nuc. Acids Res.* 12:387-395, 1984.

Another example of algorithms that are suitable for determining percent sequence identity and sequence similarity are the BLAST and the BLAST 2.0 algorithm, which are described in Altschul et al., *J. Mol. Biol.* 215:403-410, 1990 and Altschul et al., *Nucleic Acids Res.* 25:3389-3402, 1977. Software for performing BLAST analyses is publicly available through the National Center for Biotechnology Information (http://www.ncbi.nlm.nih.gov/). The BLASTN program (for nucleotide sequences) uses as defaults a word length (W) of 11, alignments (B) of 50, expectation (E) of 10, M=5, N=−4, and a comparison of both strands. The BLASTP program (for amino acid sequences) uses as defaults a word length (W) of 3, and expectation (E) of 10, and the BLOSUM62 scoring matrix (see Henikoff & Henikoff, *Proc. Natl. Acad. Sci. USA* 89:10915, 1989).

Oligonucleotide: A linear polynucleotide sequence of up to about 100 nucleotide bases in length.

Operably linked: A first nucleic acid sequence is operably linked with a second nucleic acid sequence when the first nucleic acid sequence is placed in a functional relationship with the second nucleic acid sequence. For instance, a promoter, such as the CMV promoter, is operably linked to a coding sequence if the promoter affects the transcription or expression of the coding sequence. Generally, operably linked DNA sequences are contiguous and, where necessary to join two protein-coding regions, in the same reading frame.

ORF (open reading frame): A series of nucleotide triplets (codons) coding for amino acids without any termination codons. These sequences are usually translatable into a peptide.

Peptide: A chain of amino acids of between 3 and 30 amino acids in length. In one embodiment, a peptide is from about 16 to about 25 amino acids in length. In yet another embodiment, a peptide is from about 11 to about 20 amino acids in length. In yet another embodiment, a peptide is about 12 amino acids in length.

An "IGF-II peptide" is a series of contiguous amino acid residues from a IGF-II protein. In one example, with respect to immunogenic compositions comprising a IGF-II peptide, the term further refers to variations of these peptides in which there are conservative substitutions of amino acids, so long as the variations do not alter by more than about 20% (such as no more than about 1%, about 5%, or about 10%) the ability of the peptide to produce a B cell response, or, when bound to a Major Histocompatibility Complex Class I molecule, to activate cytotoxic T lymphocytes against cells expressing wild-type IGF-II protein. Induction of CTLs using synthetic peptides and CTL cytotoxicity assays are taught in, for example, U.S. Pat. No. 5,662,907.

Peptide modifications: IGF-II polypeptides include synthetic embodiments of peptides described herein. In addition, analogs (non-peptide organic molecules), derivatives (chemically functionalized peptide molecules obtained starting with the disclosed peptide sequences) and variants (homologs) of these proteins can be utilized in the methods described herein. Each polypeptide is comprised of a sequence of amino acids, which may be either L- and/or D-amino acids, naturally occurring and otherwise.

Peptides may be modified by a variety of chemical techniques to produce derivatives having essentially the same activity as the unmodified peptides, and optionally having other desirable properties. For example, carboxylic acid groups of the protein, whether carboxyl-terminal or side chain, may be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring. Amino groups of the peptide, whether amino-terminal or side chain, may be in the form of a pharmaceutically-acceptable acid addition salt, such as HCl, HBr, acetic, benzoic, toluene sulfonic, maleic, tartaric and other organic salts, or may be modified to $C_1$-$C_{16}$ alkyl or dialkyl amino or further converted to an amide.

Hydroxyl groups of the peptide side chains may be converted to $C_1$-$C_{16}$ alkoxy or to a $C_1$-$C_{16}$ ester using well-recognized techniques. Phenyl and phenolic rings of the peptide side chains may be substituted with one or more halogen atoms, such as fluorine, chlorine, bromine or iodine, or with $C_1$-$C_{16}$ alkyl, $C_1$-$C_{16}$ alkoxy, carboxylic acids and esters thereof, or amides of such carboxylic acids. Methylene groups of the peptide side chains can be extended to homologous $C_2$-$C_4$ alkylenes. Thiols can be protected with any one of a number of well-recognized protecting groups, such as acetamide groups. Those skilled in the art will also recognize methods for introducing cyclic structures into the IGF-II peptides to select and provide conformational constraints to the structure that result in enhanced stability.

Peptidomimetic and organomimetic embodiments are envisioned, whereby the three-dimensional arrangement of the chemical constituents of such peptido- and organomimetics mimic the three-dimensional arrangement of the peptide backbone and component amino acid side chains, resulting in such peptido- and organomimetics of a IGF-II polypeptide having measurable or enhanced ability to generate an immune response. For computer modeling applications, a pharmacophore is an idealized, three-dimensional definition of the structural requirements for biological activity. Peptido- and organomimetics can be designed to fit each pharmacophore with current computer modeling software (using computer assisted drug design or CADD). See Walters, "Computer-Assisted Modeling of Drugs", in Klegerman & Groves, eds., 1993, *Pharmaceutical Biotechnology*, Interpharm Press, Buffalo Grove, Ill., pp. 165-174 and Principles of Pharmacology Munson (ed.) 1995, Ch. 102, for descriptions of techniques used in CADD. Also included are mimetics prepared using such techniques.

Pharmaceutical agent: A chemical compound or composition capable of inducing a desired therapeutic or prophylactic effect when properly administered to a subject or a cell.

Pharmaceutically acceptable carriers: The pharmaceutically acceptable carriers of use are conventional. Remington's Pharmaceutical Sciences, by E. W. Martin, Mack Publishing Co., Easton, Pa., 15th Edition, 1975, describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polynucleotide: The term polynucleotide or nucleic acid sequence refers to a polymeric form of nucleotide at least 10 bases in length. A recombinant polynucleotide includes a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (such as a cDNA) independent of other sequences. The nucleotides can be ribonucleotides, deoxyribonucleotides, or modified forms of either nucleotide. The term includes single- and double-stranded forms of DNA. A IGF-II polynucleotide is a nucleic acid encoding a IGF-II polypeptide.

Polypeptide: Any chain of amino acids, regardless of length or post-translational modification (such as glycosylation or phosphorylation). In one embodiment, the polypeptide is IGF-II polypeptide. A "residue" refers to an amino acid or amino acid mimetic incorporated in a polypeptide by an amide bond or amide bond mimetic. A polypeptide has an amino terminal (N-terminal) end and a carboxy terminal (C-terminal) end.

Probes and primers: A probe comprises an isolated nucleic acid attached to a detectable label or reporter molecule. Primers are short nucleic acids, and can be DNA oligonucleotides 15 nucleotides or more in length. Primers may be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, for example, by the polymerase chain reaction (PCR) or other nucleic-acid amplification methods known in the art. One of skill in the art will appreciate that the specificity of a particular probe or primer increases with its length. Thus, for example, a primer comprising 20 consecutive nucleotides will anneal to a target with a higher specificity than a corresponding primer of only 15 nucleotides. Thus, in order to obtain greater specificity, probes and primers may be selected that comprise 20, 25, 30, 35, 40, 50 or more consecutive nucleotides.

Promoter: A promoter is an array of nucleic acid control sequences that directs transcription of a nucleic acid. A promoter includes necessary nucleic acid sequences near the start site of transcription, for example, in the case of a polymerase II type promoter, a TATA element. A promoter also optionally includes distal enhancer or repressor elements which can be located as much as several thousand base pairs from the start site of transcription. Both constitutive and inducible promoters are included (see for example, Bitter et al., *Methods in Enzymology* 153:516-544, 1987).

Specific, non-limiting examples of promoters include promoters derived from the genome of mammalian cells (such as the metallothionein promoter) or from mammalian viruses (such as the retrovirus long terminal repeat; the adenovirus late promoter; the vaccinia virus 7.5K promoter) may be used. Promoters produced by recombinant DNA or synthetic techniques may also be used. A polynucleotide can be inserted into an expression vector that contains a promoter sequence which facilitates the efficient transcription of the inserted genetic sequence of the host. The expression vector typically contains an origin of replication, a promoter, as well as specific nucleic acid sequences that allow phenotypic selection of the transformed cells.

Purified: The term purified does not require absolute purity; rather, it is intended as a relative term. Thus, for example, a purified peptide preparation is one in which the peptide or protein is more enriched than the peptide or protein is in its natural environment within a cell. In one embodiment, a preparation is purified such that the protein or peptide represents at least 50% of the total peptide or protein content of the preparation.

The IGF-II polypeptides disclosed herein, or antibodies that specifically bind IGF-II, can be purified by any of the means known in the art. See for example *Guide to Protein Purification*, ed. Deutscher, *Meth. Enzymol.* 185, Academic Press, San Diego, 1990; and Scopes, *Protein Purification: Principles and Practice*, Springer Verlag, New York, 1982. Substantial purification denotes purification from other proteins or cellular components. A substantially purified protein is at least 60%, 70%, 80%, 90%, 95% or 98% pure. Thus, in one specific, non-limiting example, a substantially purified protein is 90% free of other proteins or cellular components.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, for example, by genetic engineering techniques.

Recombinant toxins: Chimeric proteins in which a cell targeting moiety is fused to a toxin (Pastan et al., *Science*, 254:1173-1177, 1991). If the cell targeting moiety is the Fv portion of an antibody, the molecule is termed a recombinant immunotoxin (Chaudhary et al., Nature, 339:394-397, 1989). The toxin moiety is genetically altered so that it cannot bind to the toxin receptor present on most normal cells. Recombinant immunotoxins selectively kill cells which are recognized by the antigen binding domain. These recombinant toxins and immunotoxins can be used to treat cancer, for example, cancers in which IGF-II is expressed.

Selectively hybridize: Hybridization under moderately or highly stringent conditions that exclude non-related nucleotide sequences.

In nucleic acid hybridization reactions, the conditions used to achieve a particular level of stringency will vary, depending on the nature of the nucleic acids being hybridized. For example, the length, degree of complementarity, nucleotide sequence composition (such as GC versus AT content), and nucleic acid type (such as RNA versus DNA) of the hybridizing regions of the nucleic acids can be considered in selecting hybridization conditions. An additional consideration is whether one of the nucleic acids is immobilized, for example, on a filter.

A specific, non-limiting example of progressively higher stringency conditions is as follows: 2×SSC/0.1% SDS at about room temperature (hybridization conditions); 0.2× SSC/0.1% SDS at about room temperature (low stringency conditions); 0.2×SSC/0.1% SDS at about 42° C. (moderate stringency conditions); and 0.1×SSC at about 68° C. (high stringency conditions). One of skill in the art can readily determine variations on these conditions (see *Molecular Cloning: A Laboratory Manual,* 2nd ed., Vol. 1-3, ed. Sambrook et al., Cold Spring Harbor Laboratory Press, Cold Spring Harbor, N.Y., 1989). Washing can be carried out using only one of these conditions, for example, high stringency conditions, or each of the conditions can be used, for example, for 10-15 minutes each, in the order listed above, repeating any or all of the steps listed. However, as mentioned above, optimal conditions will vary, depending on the particular hybridization reaction involved, and can be determined empirically.

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a IGF-II polypeptide will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of a $V_L$ or a $V_H$ of an antibody that specifically binds a IGF-II polypeptide are typically characterized by possession of at least about 75%, for example at least about 80%, 90%, 95%, 96%, 97%, 98% or 99% sequence identity counted over the full length alignment with the amino acid sequence of the antibody using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Specific binding agent: An agent that binds substantially only to a defined target. Thus an IGF-II specific binding agent is an agent that binds substantially to a IGF-II polypeptide. In one embodiment, the specific binding agent is a human monoclonal antibody that specifically binds the IGF-II polypeptide.

The term "specifically binds" refers, with respect to an antigen such as IGF-II, to the preferential association of an antibody or other ligand, in whole or part, with a cell or tissue bearing that antigen and not to cells or tissues lacking that antigen. It is, of course, recognized that a certain degree of non-specific interaction may occur between a molecule and a non-target cell or tissue. Nevertheless, specific binding may be distinguished as mediated through specific recognition of the antigen. Although selectively reactive antibodies bind antigen, they may do so with low affinity. On the other hand, specific binding results in a much stronger association between the antibody (or other ligand) and cells bearing the antigen than between the bound antibody (or other ligand) and cells lacking the antigen. Specific binding typically results in greater than 2-fold, such as greater than 5-fold, greater than 10-fold, or greater than 100-fold increase in amount of bound antibody or other ligand (per unit time) to a cell or tissue bearing the IGF-II polypeptide as compared to a cell or tissue lacking the polypeptide. Specific binding to a protein under such conditions requires an antibody that is selected for its specificity for a particular protein. A variety of immunoassay formats are appropriate for selecting antibodies or other ligands specifically immunoreactive with a particular protein. For example, solid-phase ELISA immunoassays are routinely used to select monoclonal antibodies specifically immunoreactive with a protein. See Harlow & Lane, *Antibodies, A Laboratory Manual*, Cold Spring Harbor Publications, New York (1988), for a description of immunoassay formats and conditions that can be used to determine specific immunoreactivity.

Subject: Living multi-cellular vertebrate organisms, a category that includes both human and veterinary subjects, including human and non-human mammals.

T Cell: A white blood cell critical to the immune response. T cells include, but are not limited to, CD4+ T cells and CD8+ T cells. A CD4+ T lymphocyte is an immune cell that carries a marker on its surface known as "cluster of differentiation 4" (CD4). These cells, also known as helper T cells, help orchestrate the immune response, including antibody responses as well as killer T cell responses. CD8+ T cells carry the "cluster of differentiation 8" (CD8) marker. In one embodiment, CD8 T cells are cytotoxic T lymphocytes. In another embodiment, a CD8 cell is a suppressor T cell.

Therapeutically effective amount: A quantity of a specific substance sufficient to achieve a desired effect in a subject being treated. For instance, this can be the amount necessary to inhibit or suppress growth of a tumor. In one embodiment, a therapeutically effective amount is the amount necessary to eliminate a tumor. When administered to a subject, a dosage will generally be used that will achieve target tissue concentrations (for example, in tumors) that has been shown to achieve a desired in vitro effect.

Toxin: A molecule that is cytotoxic for a cell. Toxins include abrin, ricin, *Pseudomonas* exotoxin (PE), diphtheria toxin (DT), botulinum toxin, saporin, restrictocin or gelonin, or modified toxins thereof. For example, PE and DT are highly toxic compounds that typically bring about death through liver toxicity. PE and DT, however, can be modified into a form for use as an immunotoxin by removing the native targeting component of the toxin (such as domain Ia of PE or the B chain of DT) and replacing it with a different targeting moiety, such as an antibody.

Transduced: A transduced cell is a cell into which has been introduced a nucleic acid molecule by molecular biology techniques. As used herein, the term transduction encompasses all techniques by which a nucleic acid molecule might be introduced into such a cell, including transfection with viral vectors, transformation with plasmid vectors, and introduction of naked DNA by electroporation, lipofection, and particle gun acceleration.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Antibodies that Specifically Bind IGF-II

The two ligands of the insulin like growth factor (IGF) system, IGF-I and IGF-II, are single-chain polypeptides sharing 62% homology with proinsulin. Exemplary amino acid sequences of human insulin chain A, insulin chain B, IGF-I precursor, mature IGF-I, IGF-II precursor (also known as "long IGF-II"), and mature IGF-II are set forth in SEQ ID NOs: 1, 2, 3, 4, 5, and 6, respectively. The degree of homology between human and mouse IGF-I is 97%, while the degree of homology between human and mouse IGF-II is 91%. Amino acid sequences of mammalian IGF-I and IGF-II, such as the mouse and human proteins, are available on the internet through GENBANK®, see for example GENBANK® Accession No. CAA00082 (human IGF-II, Jan. 28, 1993), AAB21519 (human IGF-II, May 17, 2002), NP_034644 (mouse IGF-I, updated Aug. 6, 2006) NP_034642 (mouse IGF-I, updated Aug. 6, 2006), which are incorporated herein by reference. The amino acid sequence of the insulin receptor is available through GENBANK®, see Accession Nos. P6213 (Jan. 1, 1998) and NP000199 (Apr. 19, 2006).

Figure 2:
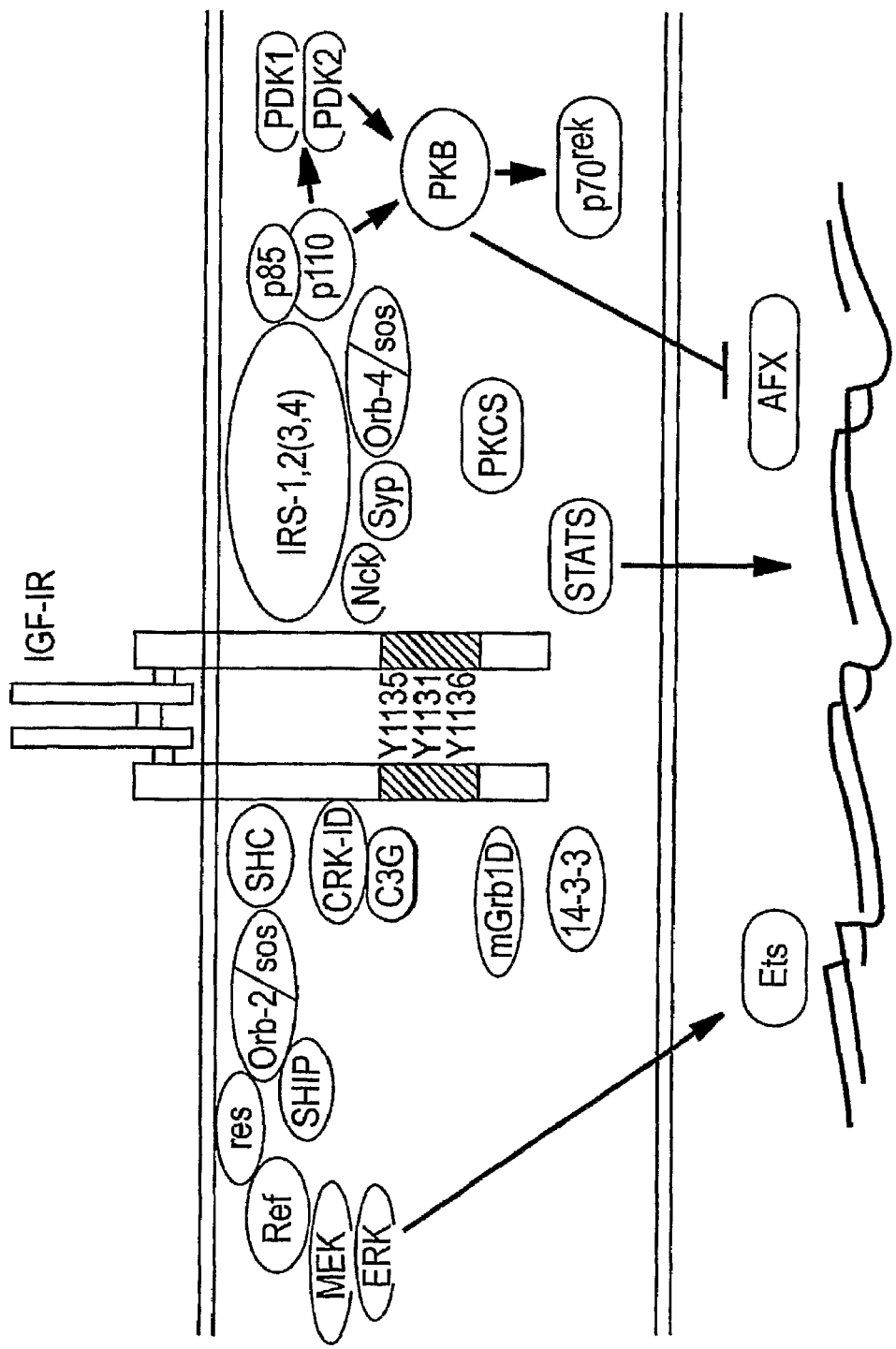
FIG. 2 is a schematic diagram of the downstream signals of IGF-IR.

Binding of IGFs to IGF-IR activates its intracellular tyrosine kinase domain, which results in autophosphorylation of the receptor. This in turn results in activation of various pathways that serve to increase cell proliferation, cell motility, and protection from apoptosis. A schematic of several of the downstream signals associated with IGF-IR is set forth in FIG. 2. IGF-IR has been linked to increased growth, survival, and oncogenic transformation of cancer cells (Kaleko et al., Mol Cell Biol 10:464-473, 1990; Baserga et al., *Biochim Biophys Acta* 1332:F105-F126, 1997; Blakesley et al., *J Endocrinol* 152:339-344, 1997; Khandwala et al., *Endocr Rev* 21:215-244, 2000), and overexpression of IGF-IR has been observed in a variety of tumor types (Bergmann et al., *Cancer Res* 55:2007-2011, 1995; Werner et al., *Adv Cancer Res* 68:183-223, 1996; Happerfield et al., *J Pathol* 183:412-417, 1997; Xie et al., *Cancer Res* 59:3588-3591, 1999; Khandwala et al., *Endocr Rev* 21:215-244, 2000; Hellawell et al., *Cancer Res* 62:2942-2950, 2002; Weber et al., *Cancer* 95:2086-2095, 2002). The ligands of IGF-IR, IGF-I and IGF-II, are known to functions as mitogens in a variety of cancer cell lines (Cullen et al., *Cancer Res* 50:48-53, 1990; Ankrapp et al., *Cancer Res* 53:3399-3404, 1993; Kappel et al., *Cancer Res* 54:2803-2807 1994; Guo et al., *J Am Coll Surg* 181:145-154, 1995; Steller et al., *Cancer Res* 56:1761-1765, 1996; Hermanto et al., *Cell Growth Differ* 11:655-664, 2000). Many tumors overexpress the IGF-II ligand (Werner et al., *Adv Cancer Res* 68:183-223, 1996), exhibiting IGF-II expression levels several fold higher than those of IGF-I. Antibodies to IGF proteins have been shown to decrease cell proliferation, increase apoptosis, and reduce tumor cell growth and metastasis (Fitzsimmons et al., *Endocrinology* 136:3100-3106, 1995; Goya, *Cancer Res* 64:6252-6258 2004; Miyamoto, *Clin Cancer Res* 11:3494-3502, 2005).

Disclosed herein are human monoclonal antibodies that specifically bind human IGF-II. A major limitation in the clinical use of mouse monoclonal antibodies is the development of a human anti-murine antibody (HAMA) response in the patients receiving the treatments. The HAMA response can involve allergic reactions and an increased rate of clearance of the administered antibody from the serum. Various types of modified monoclonal antibodies have been developed to minimize the HAMA response while trying to maintain the antigen binding affinity of the parent monoclonal antibody. One type of modified monoclonal antibody is a human-mouse chimera in which a murine antigen-binding variable region is coupled to a human constant domain (Morrison and Schlom, *Important Advances in Oncology*, Rosenberg, S. A. (Ed.), 1989). A second type of modified monoclonal antibody is the complementarity determining region (CDR)-grafted, or humanized, monoclonal antibody (Winter and Harris, *Immunol. Today* 14:243-246, 1993). However, the antibodies disclosed herein are fully human; both the framework region and the CDRs are from human antibodies. Thus, there a HAMA is not induced when these antibodies are administered to a human subject.

In one embodiment, the antibodies bind IGF-II with an equilibrium constant ($K_d$) of 1 nM or less. In another example, the antibodies bind insulin-like growth factor II (IGF-II) with an equilibrium association constant ($K_d$) of 1 nM or less, wherein the antibody bind IGF-I with an equilibrium association constant ($K_d$) of 1 mM or greater, and wherein the antibody inhibits phosphorylation of the insulin-like growth factor receptor. In additional embodiments, the antibody inhibits the phosphorylation of the insulin receptor. In several embodiments, the human monoclonal antibodies bind human IGF-II with a binding affinity of $0.1 \times 10^{-8}$ M, at least about $0.3 \times 10^{-8}$ M, at least about $0.5 \times 10^{-8}$ M, at least about $0.75 \times 10^{-8}$ M, at least about $1.0 \times 10^{-8}$ M, at least about $1.3 \times 10^{-8}$ M at least about $1.5 \times 10^{-8}$ M, or at least about $2.0 \times 10^{-8}$ M.

In additional examples, the human monoclonal antibody binds the epitope of IGF-II bound by m606 and/or m610 and/or m616, which are disclosed herein. Thus, in one example, the human monoclonal antibody binds the epitope of IGF-II bound m606 and/or m610 and/or m616 with an equilibrium disassociation constant ($K_d$) of 1 nM or less, wherein the antibody bind IGF-I with an equilibrium association constant ($K_d$) of 1 mM or greater. In additional examples, the antibody inhibits phosphorylation of the insulin-like growth factor receptor.

In a further embodiment, administration of an effective amount of the antibody to a subject decreases the autophosphorylation on tyrosine residues of the human IGF-1R as compared to a control. The phosphorylation of the human IFG-1R can be measured by any method known to one of skill in the art.

In several examples, the human monoclonal antibody includes at least one of the light chains and/or at least one of the heavy chains shown below:

```
Clone M606:
Light chain (kappa):
                                          (SEQ ID NO: 7)
  1  AGFATVAQAS DIQMTQSPSS VSASVGDRVT ITCRASQGIS
     SWLVWYQQKP

51  GKAPKLLIYA ASRLQSGVPS RFSGSGSGTL FTLIINNLQP
     EDFATYYCQQ

101  SNSVPLTFGG GTKVEIKRTV AAPSVFIFPP SDEQLKSGTA
     SVVCLLNNFY

151  PREAKVQWKV DNALQSGNSQ ESVTEQDSKD STYSLSSTLT
     LSKADYEKHK

201  VYACEVTHQG LSSPVTKSFN RGGVNSR

Heavy chain:
                                         (SEQ ID NO: 10)
  1  TRCQPAMAQV QLVESGAEVK KPGASVKVSC KASGYTFTSY
     YMHWVRQAPG

51  QGLEWMGIIN PSGGSTSYAQ KFQGRVTMTR DTSTSTVYME
     LSSLRSEDTA

101  VYYCARDRSI AAMGWFDHWG QGTLVTVSSA STKGPSVFPL
     APSSKSTSGG

151  TAALGCLVKD YFPEPVTVSW NSGALTSGVH TFPAVLQSSG
     LYSLSSVVTV

201  PSSSLGTQTY ICNVNHKPSN TKVDKKVEPK SCDKTSGQAG
     HHHHHHGDYK

251  DDDD

Clone#M610
Light chain (kappa):
                                          (SEQ ID NO: 8)
  1  AGFATVAQAC RIQMTQSPSP LSASVGDRVT ITCRASQSIS
     SYLNWYQQKP

51  GKAPKLLIYA ASSLQSGVPS RFSGSGSGTD FTLTISSLQP
     EDFATYYCQQ

101  SYSTPLTFGG GTKVEIKRTV AAPSVFIFPP SDEQLKSGTA
     SVVCLLNNFY

151  PREAKVQWKV DNALQSGNSQ ESVTEQDSKD STYSLSSTLT
     LSKADYEKHK

201  VYACEVTHQG LSSPVTKSFN RGEC

Heavy chain:
                                         (SEQ ID NO: 11)
  1  TRCQPAMAQV QLVQSGAEVK KPGASVKVSC KASGYTFTSY
     YMHWVRQAPG

51  QGLEWMGIIN PSGGSTSYAQ KFQGRVTMTR DTSTSTVYME
     LSRLRSDDTA
```

```
                                             -continued
101  VYYCARDVQW  LAYGMDVWGQ  GTTVTVSSAS  TKGPSVFPLA
     PSSKSTSGGT

151  AALGCLVKDY  FPEPVTVSWN  SGALTSGVHT  FPAVLQSSGL
     YSLSSVVTVP

201  SSSLGTQTYI  CNVNHKPSNT  KVDKKVEPKS  CDKTSGQAGH
     HHHHHGDYKD

251  DDDKG

Clone#M616:
Light chain (lambda):
                                            (SEQ ID NO: 9)
  1  VSVTPGQTAR  ITCSGDALPK  HFAYWYQQKP  GQAPVLIIYK
     DTERPSGIPE

51  RFSGSNSGNT  ATLTISRVEA  GDEADYYCQV  WDSSSGWVFG
     GGTKLTVQGQ

101  PKAAPSVTLF  PPSSEELQAN  KATLVCLISD  FYPGAVTVAW
     KADSSPVKAG

151  VETTTPSKQS  NNKYAASSYL  SLTPEQWKSH  KSYSCQVTHE
     GSTVEKTVAP

201  TECS

Heavy chain:
                                           (SEQ ID NO: 12)
  1  SQVQVLVKPS  QTLSLTCAIS  GDSVSSNSAA  WNWIRQSPSR
     GLEWLGRTYY

51  RSKWYNDYAV  SVKSRITINP  DTSKNQFSLQ  LNSVTPEDTA
     VYYCAREKGI

101  GRGITGTTIP  YNWFDPWGQG  TLVTVSSAST  KGPSVFPLAP
     SSKSTSGGTA

151  ALGCLVKDYF  PEPVTVSWNS  GALTSGVHTF  PAVLQSSGLY
     SLSSVVTVPS

201  SSLGTQTYIC  NVNHKPSNTK  VDKKVEPKSC  DKTSGQAGHH
     HHHH
```

In one embodiment, variable region of the heavy chain of the human monoclonal antibody includes amino acids 34-41 of SEQ ID NO: 10 (HCDR1). The heavy chain of the isolated human monoclonal antibody can include one or more of amino acids 59-65 of SEQ ID NO: 10 (HCDR2) and/or 105-119 of SEQ ID NO: 10 (HCDR2). The light chain of the variable region of the human monoclonal antibody can include amino acids 37-47 of SEQ ID NO: 7 (LCDR1). The variable region of the light chain of the human monoclonal antibody can include amino acids 60-68 of SEQ ID NO: 7 (LCDR2) and/or amino acids 99-109 of SEQ ID NO: 7 (LCDR3). Thus, in one example, the isolated human monoclonal antibody includes amino acids 37-47, 60-68 and 99-109 of SEQ ID NO: 7 and amino acids 34-41, 59-65, and 105-109 of SEQ ID NO: 10. In another example, the monoclonal antibody includes SEQ ID NO: 7 and SEQ ID NO: 10.

In another embodiment, the variable region of the heavy chain the monoclonal human antibody includes amino acids 34-41 of SEQ ID NO: 11 (HCDR1). The heavy chain of the human monoclonal antibody can also include amino acids 59-65 of SEQ ID NO: 11 (HCDR2) and/or amino acids 105-118 (HCDR3) of SEQ ID NO: 11. The variable region of the light chain of the human monoclonal antibody can include amino acids 37-47 (LCDR1) of SEQ ID NO: 8. The light chain of the monoclonal antibody can also include amino acids 60-68 of SEQ ID NO: 8 (LCD) and/or amino acids 99-109 of SEQ ID NO: 8 (LCDR3). Thus, in one example, the variable region of the heavy chain the antibody includes amino acids 37-47, 60-68 and 99-108 of SEQ ID NO: 8 and amino acids 34-41, 59-65, and 105-109 of SEQ ID NO: 11. The monoclonal antibody can also include SEQ ID NO: 8 and SEQ ID NO: 11.

In a further embodiment, variable region of the heavy chain can include amino acids 21-30 of SEQ ID NO: 12. In additional examples, the heavy chain comprises amino acids 48-55 of SEQ ID NO: 12 and/or amino acids 101-117 of SEQ ID NO: 12. In other examples the light chain of the human monoclonal antibody includes one, two or all three of the sequences set forth as amino acids 37-42 of SEQ ID NO: 9 and/or amino acids 60-69 of SEQ ID NO: 9 and/or amino acids 99-109 of SEQ ID NO: 9. Thus, one exemplary human monoclonal antibody that specifically binds IGF-II includes amino acids 37-42, 60-69 and 99-109 of SEQ ID NO: 9 and amino acids 21-30 of SEQ ID NO: 12 and/or amino acids 48-55 of SEQ ID NO: 12 and/or amino acid 101-117 of SEQ ID NO: 12. Thus, the human monoclonal antibody can include SEQ ID NO: 9 and SEQ ID NO: 0.12.

The monoclonal antibody can be of any isotype. The monoclonal antibody can be, for example, an IgM or an IgG antibody, such as IgG$_1$ or an IgG$_2$. The class of an antibody that specifically binds IGF-II can be switched with another. In one aspect, a nucleic acid molecule encoding V$_L$ or V$_H$ is isolated using methods well-known in the art, such that it does not include any nucleic acid sequences encoding the constant region of the light or heavy chain, respectively. The nucleic acid molecule encoding V$_L$ or V$_H$ is then operatively linked to a nucleic acid sequence encoding a CL or CH from a different class of immunoglobulin molecule. This can be achieved using a vector or nucleic acid molecule that comprises a CL or CH chain, as known in the art. For example, an antibody that specifically binds IGF-II that was originally IgM may be class switched to an IgG. Class switching can be used to convert one IgG subclass to another, such as from IgG$_1$ to IgG$_2$.

Fully human monoclonal antibodies include a human framework region. This human framework region can be the framework regions disclosed in one or more of SEQ ID NOS: 7-12 (these sequences include CDR sequences as well as framework sequences). However, the framework regions can be from another source.

Antibody fragments are encompassed by the present disclosure, such as Fab, F(ab')$_2$, and Fv which include a heavy chain and light chain variable region and are capable of binding the epitopic determinant on IGF-II. These antibody fragments retain the ability to selectively bind with the antigen. These fragments include:

(1) Fab, the fragment which contains a monovalent antigen-binding fragment of an antibody molecule, can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, a genetically engineered fragment containing the variable region of the light chain and the variable region of the heavy chain expressed as two chains; and (5) Single chain antibody (such as scFv), defined as a genetically engineered molecule containing the variable region of the light chain, the variable region of the heavy chain, linked by a suitable polypeptide linker as a genetically fused single chain molecule.

(6) A dimer of a single chain antibody (scFV$_2$), defined as a dimer of an scFV. This has also been termed a "minianti-body."

Methods of making these fragments are known in the art (see for example, Harlow and Lane, *Antibodies: A Laboratory Manual*, Cold Spring Harbor Laboratory, New York, 1988). In several examples, the variable region included in the antibody is the variable region of m606, m610 or m616. In one group of embodiments, the antibodies have V$_H$ CDRs of m606, m610 or m616, or a combination of these CDRs, as discussed above.

In a further group of embodiments, the antibodies are Fv antibodies, which are typically about 25 kDa and contain a complete antigen-binding site with three CDRs per each heavy chain and each light chain. To produce these antibodies, the V$_H$ and the V$_L$ can be expressed from two individual nucleic acid constructs in a host cell. If the V$_H$ and the V$_L$ are expressed non-contiguously, the chains of the Fv antibody are typically held together by noncovalent interactions. However, these chains tend to dissociate upon dilution, so methods have been developed to crosslink the chains through glutaraldehyde, intermolecular disulfides, or a peptide linker. Thus, in one example, the Fv can be a disulfide stabilized Fv (dsFv), wherein the heavy chain variable region and the light chain variable region are chemically linked by disulfide bonds.

In an additional example, the Fv fragments comprise V$_H$ and V$_L$ chains connected by a peptide linker. These single-chain antigen binding proteins (scFv) are prepared by constructing a structural gene comprising DNA sequences encoding the V$_H$ and V$_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing scFvs are known in the art (see Whitlow et al., *Methods: a Companion to Methods in Enzymology*, Vol. 2, page 97, 1991; Bird et al., *Science* 242: 423, 1988; U.S. Pat. No. 4,946,778; Pack et al., *Bio/Technology* 11:1271, 1993; and Sandhu, supra). Dimers of a single chain antibody (scFV$_2$), are also contemplated.

Antibody fragments can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly (see U.S. Pat. No. 4,036,945 and U.S. Pat. No. 4,331,647, and references contained therein; Nisonhoff et al., *Arch. Biochem. Biophys.* 89:230, 1960; Porter, *Biochem. J.* 73:119, 1959; Edelman et al., *Methods in Enzymology*, Vol. 1, page 422, Academic Press, 1967; and Coligan et al. at sections 2.8.1-2.8.10 and 2.10.1-2.10.4).

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

One of skill will realize that conservative variants of the antibodies can be produced. Such conservative variants employed in antibody fragments, such as dsFv fragments or in scFv fragments, will retain critical amino acid residues necessary for correct folding and stabilizing between the V$_H$ and the V$_L$ regions, and will retain the charge characteristics of the residues in order to preserve the low pI and low toxicity of the molecules. Amino acid substitutions (such as at most one, at most two, at most three, at most four, or at most five amino acid substitutions) can be made in the V$_H$ and the V$_L$ regions to increase yield. Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Thus, one of skill in the art can readily review the sequences shown in Table 1, identify a conservative substitution, and produce the conservative variant using well-known molecular techniques.

Effector molecules, such as therapeutic, diagnostic, or detection moieties can be linked to an antibody of interest, such as a human antibody that specifically binds IGF-II, using any number of means known to those of skill in the art. Both covalent and noncovalent attachment means may be used. The procedure for attaching an effector molecule to an antibody varies according to the chemical structure of the effector. Polypeptides typically contain a variety of functional groups; such as carboxylic acid (COOH), free amine (—NH$_2$) or sulfhydryl (—SH) groups, which are available for reaction with a suitable functional group on an antibody to result in the binding of the effector molecule. Alternatively, the antibody is derivatized to expose or attach additional reactive functional groups. The derivatization may involve attachment of any of a number of linker molecules such as those available from Pierce Chemical Company, Rockford, Ill. The linker can be any molecule used to join the antibody to the effector molecule. The linker is capable of forming covalent bonds to both the antibody and to the effector molecule. Suitable linkers are well known to those of skill in the art and include, but are not limited to, straight or branched-chain carbon linkers, heterocyclic carbon linkers, or peptide linkers. Where the antibody and the effector molecule are polypeptides, the linkers may be joined to the constituent amino acids through their side groups (such as through a disulfide linkage to cysteine) or to the alpha carbon amino and carboxyl groups of the terminal amino acids.

In some circumstances, it is desirable to free the effector molecule from the antibody when the immunoconjugate has reached its target site. Therefore, in these circumstances, immunoconjugates will comprise linkages that are cleavable in the vicinity of the target site. Cleavage of the linker to release the effector molecule from the antibody may be prompted by enzymatic activity or conditions to which the immunoconjugate is subjected either inside the target cell or in the vicinity of the target site.

In view of the large number of methods that have been reported for attaching a variety of radiodiagnostic compounds, radiotherapeutic compounds, label (such as enzymes or fluorescent molecules) drugs, toxins, and other agents to antibodies one skilled in the art will be able to determine a suitable method for attaching a given agent to an antibody or other polypeptide.

The antibodies or antibody fragments disclosed herein can be derivatized or linked to another molecule (such as another peptide or protein). In general, the antibodies or portion thereof is derivatized such that the binding to IGF-II is not affected adversely by the derivatization or labeling. For example, the antibody can be functionally linked (by chemical coupling, genetic fusion, noncovalent association or otherwise) to one or more other molecular entities, such as another antibody (for example, a bispecific antibody or a diabody), a detection agent, a pharmaceutical agent, and/or a protein or peptide that can mediate associate of the antibody or antibody portion with another molecule (such as a streptavidin core region or a polyhistidine tag).

One type of derivatized antibody is produced by crosslinking two or more antibodies (of the same type or of different types, such as to create bispecific antibodies). Suitable crosslinkers include those that are heterobifunctional, having two distinctly reactive groups separated by an appropriate spacer (such as m-maleimidobenzoyl-N-hydroxysuccinimide ester) or homobifunctional (such as disuccinimidyl suberate). Such linkers are available from Pierce Chemical Company, Rockford, Ill.

A human antibody that specifically binds IGF-II can be labeled with a detectable moiety. Useful detection agents include fluorescent compounds, including fluorescein, fluorescein isothiocyanate, rhodamine, 5-dimethylamine-1-napthalenesulfonyl chloride, phycoerythrin, lanthanide phosphors and the like. Bioluminescent markers are also of use, such as luciferase, Green fluorescent protein (GFP), Yellow fluorescent protein (YFP). An antibody can also be labeled with enzymes that are useful for detection, such as horseradish peroxidase, β-galactosidase, luciferase, alkaline phosphatase, glucose oxidase and the like. When an antibody is labeled with a detectable enzyme, it can be detected by adding additional reagents that the enzyme uses to produce a reaction product that can be discerned. For example, when the agent horseradish peroxidase is present, the addition of hydrogen peroxide and diaminobenzidine leads to a colored reaction product, which is visually detectable. An antibody may also be labeled with biotin, and detected through indirect measurement of avidin or streptavidin binding. It should be noted that the avidin itself can be labeled with an enzyme or a fluorescent label.

An antibody may be labeled with a magnetic agent, such as gadolinium. Antibodies can also be labeled with lanthanides (such as europium and dysprosium), and manganese. Paramagnetic particles such as superparamagnetic iron oxide are also of use as labels. An antibody may also be labeled with a predetermined polypeptide epitopes recognized by a secondary reporter (such as leucine zipper pair sequences, binding sites for secondary antibodies, metal binding domains, epitope tags). In some embodiments, labels are attached by spacer arms of various lengths to reduce potential steric hindrance.

An antibody can also be labeled with a radiolabeled amino acid. The radiolabel may be used for both diagnostic and therapeutic purposes. For instance, the radiolabel may be used to detect IGF-II by x-ray, emission spectra, or other diagnostic techniques. Examples of labels for polypeptides include, but are not limited to, the following radioisotopes or radionuclides: $^{3}$H, $^{14}$C, $^{15}$N, $^{35}$S, $^{90}$Y, $^{99}$Tc, $^{111}$In, $^{125}$I, $^{131}$I.

An antibody can also be derivatized with a chemical group such as polyethylene glycol (PEG), a methyl or ethyl group, or a carbohydrate group. These groups may be useful to improve the biological characteristics of the antibody, such as to increase serum half-life or to increase tissue binding.

In one embodiment, the antibody that specifically binds IGF-II inhibits phosphorylation of the insulin-like growth factor type I receptor (IGF-IR). IGF-II binds the IGF-I receptor, and causes tyrosine phosphorylation. Tyrosine phosphorylation of IGF-IR is one of the early responses to potent mitogenic stimuli, such as the binding of IGF-I or IFG-II. The IGF-I receptor binds IGF-I and IGF-II with high affinity to activate cellular proliferation in both normal growth and development and malignant transformation and has tyrosine kinase activity. IGF-IR is highly overexpressed in most malignant tissues where it functions as an anti-apoptotic agent by enhancing cell survival. Tyrosine phosphorylation status of proteins can be determined using anti-phosphotyrosine antibodies. In addition, because of the binding specificity of the SH2 domain to phosphorylated tyrosine residues, a specific pattern of tyrosine phosphorylation can be elucidated to determine phosphorylation status.

Immunoassays for determining IGF-IR tyrosine phosphorylation or for measuring total IGF-IR levels are an ELISA or Western blot. If only the cell surface level of IGF-IR is to be measured, the cells are not lysed, and the cell surface levels of IGF-IR are measured using one of the assays described herein. In one example, the immunoassay for determining cell surface levels of IGF-IR includes the steps of labeling the cell surface proteins with a detectable label, such as $^{32}$P, immunoprecipitating the IGF-IR with an anti-IGF-IR antibody and then detecting the phosphorylated IGF-IR.

Nucleic acids encoding the amino acid sequences of the antibodies that bind IGF-II are also provided herein. Exemplary nucleic acid sequences are as follows:

```
Fab m606:
Light chain:
GGCTGGTTTCGCTACCGTGGCCCAGGCGTCCGACATCCAGATGACCCAGTCTCCATCTTC  (SEQ ID NO: 13)

CGTGTCTGCATCTGTAGGAGACAGAGTTACCATCACTTGTCGGGCGAGTCAGGGTATTAG

TAGTTGGTTGGTCTGGTATCAACAAAAACCCGGAAAAGCCCCTAAACTCCTGATCTATGC

TGCATCCCGTTTACAAAGTGGGGTCCCATCAAGGTTCAGCGGCAGTGGATCTGGGACACT

TTTCACTCTCATCATCAACAACCTGCAGCCTGAAGATTTTGCAACTTACTATTGTCAACA

GTCTAATAGTGTCCCTCTCACTTTCGGCGGAGGGACCAAGGTGGAGATCAAGCGAACTGT

GGCTGCACCATCTGTCTTCATCTTCCCGCCATCTGATGAGCAGTTGAAATCTGGAACTGC

CTCTGTTGTGTGCCTGCTGAATAACTTCTATCCCAGAGAGGCCAAAGTACAGTGGAAGGT

GGATAACGCCCTCCAATCGGGTAACTCCCAGGAGAGTGTCACAGAGCAGGACAGCAAGGA
```

```
CAGCACCTACAGCCTCAGCAGCACCCTGACGCTGAGCAAAGCAGACTACGAGAAACACAA

AGTCTACGCCTGCGAAGTCACCCATCAGGGCCTGAGCTCGCCCGTCACAAAGAGCTTCAA

CAGGGGAGGTGTTAATTCTAGATAATTAATTAGGAGGAATTTAAAATGAAATACCTATTG

CCTACGGCAGCCGCTGGATTGTTATTACTCGCTGCCCAACCAGCCATGGCCCAGGTGCAG

CTGGTGGAGTCTGGGGCTGAGGTGAAGAAAGCCTGGGCCTCAGTGAGGTTTCCTGCAGGC

ATCTGGATACCCTTCACCAGCTACTATATGCACT

Heavy chain:
TGCAGCTGGTGGAGTCTGGGGCTGAGGTGAA                                (SEQ ID NO: 14)

GAAGCCTGGGGCCTCAGTGAAGGTTTCCTGCAAGGCATCTGGATACACCTTCACCAGCTA

CTATATGCACTGGGTGCGACAGGCCCCTGGACAAGGGCTTGAGTGGATGGGAATAATCAA

CCCTAGTGGTGGTAGCACAAGCTACGCACAGAAGTTCCAGGGCAGAGTCACCATGACCAG

GGACACGTCCACGAGCACAGTCTACATGGAGCTGAGCAGCCTGAGATCTGAGGACACGGC

CGTGTATTACTGTGCGAGAGATAGGAGTATAGCAGCAATGGGGTGGTTCGACCACTGGGG

CCAGGGAACCCTGGTCACCGTCTCCTCAGCCTCCACCAAGGGCCCATCGGTCTTCCCCCT

GGCACCCTCCTCCAAGAGCACCTCTGGGGGCACAGCGGCCCTGGGCTGCCTGGTCAAGGA

CTACTTCCCCGAACCGGTGACGGTGTCGTGGAACTCAGGCGCCCTGACCAGCGGCGTGCA

CACCTTCCCGGCTGTCCTACAGTCCTCAGGACTCTACTCCCTCAGCAGCGTGGTGACCGT

GCCCTCCAGCAGCTTGGGCACCCAGACCTACATCTGCAACGTGAATCACAAGCCCAGCAA

CACCAAGGTGGACAAGAAAGTTGAGCCCAAATCTTGTGACAAAACTAGTGGCCAGGCCGG

CCACCACCACCACCACCA

Fab m610:
Light chain:
GCTGGTTTCGCTACCGTGGCCCAGGCGTGCCGAATCCAGATGACCCAGTCTCCATCCCCC  (SEQ ID NO: 15)

CTGTCTGCATCTGTAGGAGACAGAGTCACCATCACTTGCCGGGCAAGTCAGAGCATTAGC

AGCTATTTAAATTGGTATCAGCAGAAACCAGGGAAAGCCCCTAAGCTCCTGATCTATGCT

GCATCCAGTTTGCAAAGTGGGGTCCCATCAAGGTTCAGTGGCAGTGGATCTGGGACAGAT

TTCACTCTCACCATCAGCAGTCTGCAACCTGAAGATTTTGCAACTTACTACTGTCAACAG

AGTTACAGTACCCCGCTCACTTTCGGCGGAGGGACCAAGGTGGAGATCAAACGAACTGTG

GCTGCACCATCTGTCTTCATCTTCCCGCCATCTGATGAGCAGTTGAAATCTGGAACTGCC

TCTGTTGTGTGCCTGCTGAATAACTTCTATCCCAGAGAGGCCAAAGTACAGTGGAAGGTG

GATAACGCCCTCCAATCGGGTAACTCCCAGGAGAGTGTCACAGAGCAGGACAGCAAGGAC

AGCACCTACAGCCTCAGCAGCACCCTGACGCTGAGCAAAGCAGACTACGAGAAACACAAA

GTCTACGCCTGCGAAGTCACCCATCAGGGCCTGAGCTCGCCCGTCACAAAGAGCTTCAAC

AGGGGAGAGTGTTAATTCTAGATAATTAATTAGGAGGAATTTAAAATGAAATACCTATTG

CCTACGGCAGCCGCTGGATTGTTATTACTCGCTGCCCAACCAGCCATGGCCGA

AGT

Heavy chain:
ACTCGCTGCCAACCAGCCATGGCTCAAGTGCAGCTGGTGCAGTCTGGGGCTGAGGTGAA  (SEQ ID NO: 16)

GAAGCCTGGGGCCTCAGTGAAGGTTTCCTGCAAGGCATCTGGATACACCTTCACCAGCTA

CTATATGCACTGGGTGCGACAGGCCCCTGGACAAGGGCTTGAGTGGATGGGAATAATCAA

CCCTAGTGGTGGTAGCACAAGCTACGCACAGAAGTTCCAGGGCAGAGTCACCATGACCAG

GGACACGTCCACGAGCACAGTCTACATGGAGCTGAGCAGGCTGAGATCTGACGACACGGC
```

-continued

```
CGTGTATTACTGTGCGAGAGATGTGCAGTGGCTGGCATACGGTATGGACGTCTGGGGCCA

AGGGACCACGGTCACCGTCTCCTCAGCCTCCACCAAGGGCCCATCGGTCTTCCCCCTGGC

ACCCTCCTCCAAGAGCACCTCTGGGGGCACAGCGGCCCTGGGCTGCCTGGTCAAGGACTA

CTTCCCCGAACCGGTGACGGTGTCGTGGAACTCAGGCGCCCTGACCAGCGGCGTGCACAC

CTTCCCGGCTGTCCTACAGTCCTCAGGACTCTACTCCCTCAGCAGCGTGGTGACCGTGCC

CTCCAGCAGCTTGGGCACCCAGACCTACATCTGCAACGTGAATCACAAGCCCAGCAACAC

CAAGGTGGACAAGAAAGTTGAGCCCAAATCTTGTGACAAAACTAGTGGCCAGGCCGGCCA

CCACCACCACCACCACGGCGACTACAAGGACGATGACGATAA

Fab m616:
Light Chain:
TAACTCAGCCACCCTC                                                (SEQ ID NO: 17)

GGTGTCAGTGACCCCAGGACAGACGGCCAGGATCACCTGCTCTGGAGATGCATTGCCAAA

GCACTTTGCTTATTGGTACCAACAGAAGCCAGGCCAGGCCCCTGTATTGATAATATATAA

AGACACTGAGAGGCCCTCAGGGATCCCTGAGCGATTCTCTGGCTCCAACTCTGGGAACAC

GGCCACCCTGACCATTAGCAGGGTCGAAGCCGGGGATGAGGCCGACTATTACTGTCAGGT

GTGGGATAGTAGTAGTGGTTGGGTGTTCGGCGGAGGGACCAAGCTGACCGTCCAAGGTCA

GCCCAAGGCTGCCCCCTCGGTCACTCTGTTCCCACCCTCCTCTGAGGAGCTTCAAGCCAA

CAAGGCCACACTGGTGTGTCTCATAAGTGACTTCTACCCGGGAGCCGTGACAGTGGCCTG

GAAGGCAGATAGCAGCCCCGTCAAGGCGGGAGTGGAGACCACCACACCCTCCAAACAAAG

CAACAACAAGTACGCGGCCAGCAGCTACCTGAGCCTGACGCCTGAGCAGTGGAAGTCCCA

CAAAAGCTACAGCTGCCAGGTCACGCATGAAGGGAGCACCGTGGAGAAGACAGTGGCCCC

TACAGAATGTTCATAATTCTAGATAATTAATTAGGAGGAATTTAAAATGAAATACCTATT

GCCTACGGCAGCCGCTGGATTGTTATTACTCGCTGCCCA

Heavy Chain:
ACAGTCAGGTCC                                                    (SEQ ID NO: 18)

AGGTACTGGTGAAGCCCTCGCAGACCCTCTCACTCACCTGTGCCATCTCCGGGGACAGTG

TCTCTAGCAACAGTGCTGCTTGGAACTGGATCAGGCAGTCCCCATCGAGAGGCCTTGAGT

GGCTGGGAAGGACATACTACAGGTCCAAGTGGTATAATGATTATGCAGTATCTGTGAAAA

GTCGAATAACCATCAACCCAGACACATCCAAGAACCAGTTCTCCCTGCAGCTGAACTCTG

TGACTCCCGAGGACACGGCTGTGTATTACTGTGCAAGAGAGAAGGGGATAGGTCGGGGTA

TAACTGGAACTACAATTCCGTACAACTGGTTCGACCCCTGGGGCCAGGGAACCCTGGTCA

CCGTCTCTTCAGCCTCCACCAAGGGCCCATCGGTCTTCCCCCTGGCACCCTCCTCCAAGA

GCACCTCTGGGGGCACAGCGGCCCTGGGCTGCCTGGTCAAGGACTACTTCCCCGAACCGG

TGACGGTGTCGTGGAACTCAGGCGCCCTGACCAGCGGCGTGCACACCTTCCCGGCTGTCC

TACAGTCCTCAGGACTCTACTCCCTCAGCAGCGTGGTGACCGTGCCCTCCAGCAGCTTGG

GCACCCAGACCTACATCTGCAACGTGAATCACAAGCCCAGCAACACCAAGGTGGACAAGA

AAGTTGAGCCCAAATCTTGTGACAAAACTAGTGGCCAGGCCGGCCACCACCACCACCACC

ACGG
```

Nucleotides molecules encoding the antibodies can readily be produced by one of skill in the art, using the amino acid sequences provided herein, and the genetic code. In addition, one of skill can readily construct a variety of clones containing functionally equivalent nucleic acids, such as nucleic acids which differ in sequence but which encode the same effector molecule ("EM") or antibody sequence. Thus, nucleic acids encoding antibodies, conjugates and fusion proteins are provided herein.

Nucleic acid sequences encoding the human antibodies that specifically bind IGF-II can be prepared by any suitable method including, for example, cloning of appropriate sequences or by direct chemical synthesis by methods such as the phosphotriester method of Narang et al., *Meth. Enzymol.* 68:90-99, 1979; the phosphodiester method of Brown et al., *Meth. Enzymol.* 68:109-151, 1979; the diethylphosphoramidite method of Beaucage et al., *Tetra. Lett.* 22:1859-1862, 1981; the solid phase phosphoramidite triester method described by Beaucage & Caruthers, *Tetra. Letts.* 22(20): 1859-1862, 1981, for example, using an automated synthesizer as described in, for example, Needham-VanDevanter et al., *Nucl. Acids Res.* 12:6159-6168, 1984; and, the solid support method of U.S. Pat. No. 4,458,066. Chemical synthesis produces a single stranded oligonucleotide. This can be converted into double stranded DNA by hybridization with a complementary sequence, or by polymerization with a DNA polymerase using the single strand as a template. One of skill would recognize that while chemical synthesis of DNA is generally limited to sequences of about 100 bases, longer sequences may be obtained by the ligation of shorter sequences.

Exemplary nucleic acids encoding sequences encoding a human antibody that specifically binds IGF-II can be prepared by cloning techniques. Examples of appropriate cloning and sequencing techniques, and instructions sufficient to direct persons of skill through many cloning exercises are found in Sambrook et al., supra, Berger and Kimmel (eds.), supra, and Ausubel, supra. Product information from manufacturers of biological reagents and experimental equipment also provide useful information. Such manufacturers include the SIGMA Chemical Company (Saint Louis, Mo.), R&D Systems (Minneapolis, Minn.), Pharmacia Amersham (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), Invitrogen (San Diego, Calif.), and Applied Biosystems (Foster City, Calif.), as well as many other commercial sources known to one of skill.

Nucleic acids can also be prepared by amplification methods. Amplification methods include polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill.

In one example, an antibody of use is prepared by inserting the cDNA which encodes a variable region from an antibody into a vector which comprises the cDNA encoding an effector molecule (EM), such as an enzyme or label. The insertion is made so that the variable region and the EM are read in frame so that one continuous polypeptide is produced. Thus, the encoded polypeptide contains a functional Fv region and a functional EM region. In one embodiment, cDNA encoding an enzyme is ligated to a scFv so that the enzyme is located at the carboxyl terminus of the scFv. In several examples, cDNA encoding a horseradish peroxidase or alkaline phosphatase, or a polypeptide marker of interest is ligated to a scFv so that the enzyme (or polypeptide marker) is located at the amino terminus of the scFv. In another example, the label is located at the amino terminus of the scFv. In a further example, cDNA encoding the protein or polypeptide marker is ligated to a heavy chain variable region of an antibody, so that the enzyme or polypeptide marker is located at the carboxyl terminus of the heavy chain variable region. The heavy chain-variable region can subsequently be ligated to a light chain variable region of the antibody using disulfide bonds. In a yet another example, cDNA encoding an enzyme or a polypeptide marker is ligated to a light chain variable region of an antibody, so that the enzyme or polypeptide marker is located at the carboxyl terminus of the light chain variable region. The light chain-variable region can subsequently be ligated to a heavy chain variable region of the antibody using disulfide bonds.

Once the nucleic acids encoding the antibody, labeled antibody, or fragment thereof are isolated and cloned, the protein can be expressed in a recombinantly engineered cell such as bacteria, plant, yeast, insect and mammalian cells using a suitable expression vector. One or more DNA sequences encoding the antibody or fragment thereof can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art. Hybridomas expressing the antibodies of interest are also encompassed by this disclosure.

Polynucleotide sequences encoding the antibody, labeled antibody, or functional fragment thereof, can be operatively linked to expression control sequences. An expression control sequence operatively linked to a coding sequence is ligated such that expression of the coding sequence is achieved under conditions compatible with the expression control sequences. The expression control sequences include, but are not limited to appropriate promoters, enhancers, transcription terminators, a start codon (i.e., ATG) in front of a protein-encoding gene, splicing signal for introns, maintenance of the correct reading frame of that gene to permit proper translation of mRNA, and stop codons.

The polynucleotide sequences encoding the antibody, labeled antibody, or functional fragment thereof can be inserted into an expression vector including, but not limited to a plasmid, virus or other vehicle that can be manipulated to allow insertion or incorporation of sequences and can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art.

Transformation of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired, or by electroporation.

When the host is a eukaryote, such methods of transfection of DNA as calcium phosphate coprecipitates, conventional mechanical procedures such as microinjection, electroporation, insertion of a plasmid encased in liposomes, or virus vectors may be used. Eukaryotic cells can also be cotransformed with polynucleotide sequences encoding the antibody, labeled antibody, or functional fragment thereof, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, *Eukaryotic Viral Vectors*, Cold Spring Harbor Laboratory, Gluzman ed., 1982). One of skill in the art can readily use an expression systems such as plasmids and vectors of use in producing proteins in cells including higher eukaryotic cells such as the COS, CHO, HeLa and myeloma cell lines.

Isolation and purification of recombinantly expressed polypeptide can be carried out by conventional means including preparative chromatography and immunological separations. Once expressed, the antibody, labeled antibody or functional fragment thereof can be purified according to standard procedures of the art, including ammonium sulfate precipitation, affinity columns, column chromatography, and the like (see, generally, R. Scopes, *Protein Purification*, Springer-Verlag, N.Y., 1982). Substantially pure compositions of at least about 90 to 95% homogeneity are disclosed herein, and 98 to 99% or more homogeneity can be used for pharmaceutical purposes. Once purified, partially or to homogeneity as desired, if to be used therapeutically, the polypeptides should be substantially free of endotoxin.

Methods for expression of single chain antibodies and/or refolding to an appropriate active form, including single chain antibodies, from bacteria such as *E. coli* have been described and are well-known and are applicable to the antibodies disclosed herein. See, Buchner et al., *Anal. Biochem.* 205:263-270, 1992; Pluckthun, *Biotechnology* 9:545, 1991; Huse et al., *Science* 246:1275, 1989 and Ward et al., *Nature* 341:544, 1989, all incorporated by reference herein.

Often, functional heterologous proteins from *E. coli* or other bacteria are isolated from inclusion bodies and require solubilization using strong denaturants, and subsequent refolding. During the solubilization step, as is well known in the art, a reducing agent must be present to separate disulfide bonds. An exemplary buffer with a reducing agent is: 0.1 M Tris pH 8, 6 M guanidine, 2 mM EDTA, 0.3 M DTE (dithioerythritol). Reoxidation of the disulfide bonds can occur in the presence of low molecular weight thiol reagents in reduced and oxidized form, as described in Saxena et al., *Biochemistry* 9: 5015-5021, 1970, incorporated by reference herein, and especially as described by Buchner et al., supra.

Renaturation is typically accomplished by dilution (for example, 100-fold) of the denatured and reduced protein into refolding buffer. An exemplary buffer is 0.1 M Tris, pH 8.0, 0.5 M L-arginine, 8 mM oxidized glutathione (GSSG), and 2 mM EDTA.

As a modification to the two chain antibody purification protocol, the heavy and light chain regions are separately solubilized and reduced and then combined in the refolding solution. An exemplary yield is obtained when these two proteins are mixed in a molar ratio such that a 5 fold molar excess of one protein over the other is not exceeded. Excess oxidized glutathione or other oxidizing low molecular weight compounds can be added to the refolding solution after the redox-shuffling is completed.

In addition to recombinant methods, the antibodies, labeled antibodies and functional fragments thereof that are disclosed herein can also be constructed in whole or in part using standard peptide synthesis. Solid phase synthesis of the polypeptides of less than about 50 amino acids in length can be accomplished by attaching the C-terminal amino acid of the sequence to an insoluble support followed by sequential addition of the remaining amino acids in the sequence. Techniques for solid phase synthesis are described by Barany & Merrifield, *The Peptides: Analysis, Synthesis, Biology. Vol.* 2. *Special Methods in Peptide Synthesis, Part A.* pp. 3-284; Merrifield et al., *J. Am. Chem. Soc.* 85:2149-2156, 1963, and Stewart et al., *Solid Phase Peptide Synthesis,* 2nd ed., Pierce Chem. Co., Rockford, Ill., 1984. Proteins of greater length may be synthesized by condensation of the amino and carboxyl termini of shorter fragments. Methods of forming peptide bonds by activation of a carboxyl terminal end (such as by the use of the coupling reagent N,N'-dicylohexylcarbodimide) are well known in the art.

Recombinant anti-IGF-IR human antibodies in addition to the anti-IGF-IR antibodies disclosed herein can be isolated by screening of a recombinant combinatorial antibody library, preferably a scFv phage display library, prepared using cDNAs of the variable regions of heavy and light chains prepared from mRNA derived from human lymphocytes. Methodologies for preparing and screening such libraries are known in the art. There are commercially available kits for generating phage display libraries (for example, the Pharmacia Recombinant Phage Antibody System, catalog no. 27-9400-01; and the Stratagene SurfZAP™ phage display kit, catalog no. 240612). There are also other methods and reagents that can be used in generating and screening antibody display libraries (see, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; Fuchs et al., Bio/Technology 9:1370-1372, 1991; Hay et al., Hum. Antibod. Hybridomas 3:81-85, 1992; Huse et al., Science 246:1275-1281, 1989; McCafferty et al., Nature 348:552-554, 1990; Griffiths et al. EMBO J. 12:725-734, 1993)

In one embodiment, to isolate additional human antibodies that specifically bind IGF-II, a human antibody that specifically binds IGF-II, as described herein, is first used to select human heavy and light chain sequences having similar binding activity toward IGF-II, such as using the epitope imprinting methods disclosed in PCT Publication No. WO 93/06213. The antibody libraries used in this method are scFv libraries prepared and screened, using methods such as those as described in PCT Publication No. WO 92/01047, McCafferty et al., Nature 348:552-554, 1990; and/or Griffiths et al., EMBO J 12:725-734, 1993 using human IGF-II as the antigen.

Once initial human variable light chain (VL) and variable heavy chain (VH) segments are selected, "mix and match" experiments, in which different pairs of the initially selected VL and VH segments are screened for IGF-II binding, are performed to select VL/VH pair combinations of interest. Additionally, to increase binding affinity of the antibody, the VL and VH segments can be randomly mutated, such as within H-CDR3 region or the L-CDR3 region, in a process analogous to the in vivo somatic mutation process responsible for affinity maturation of antibodies during a natural immune response. This in vitro affinity maturation can be accomplished by amplifying VH and VL regions using PCR primers complimentary to the H-CDR3 or L-CDR3, respectively. In this process, the primers have been "spiked" with a random mixture of the four nucleotide bases at certain positions such that the resultant PCR products encode VH and VL segments into which random mutations have been introduced into the VH and/or VL CDR3 regions. These randomly mutated VH and VL segments can be tested to determine the binding affinity for IGF-II.

Following screening and isolation of an antibody that binds IGF-II from a recombinant immunoglobulin display library, nucleic acid encoding the selected antibody can be recovered from the display package (for example, from the phage genome) and subcloned into other expression vectors by standard recombinant DNA techniques, as described above. If desired, the nucleic acid can be further manipulated to create other antibody fragments, also as described below. To express a recombinant human antibody isolated by screening of a combinatorial library, the DNA encoding the antibody is cloned into a recombinant expression vector and introduced into a mammalian host cells, as described above.

Compositions and Therapeutic Methods

Compositions are provided that include one or more of the antibodies that specifically bind IGF-II that are disclosed herein in a carrier. The compositions can be prepared in unit dosage forms for administration to a subject. The amount and timing of administration are at the discretion of the treating physician to achieve the desired purposes. The antibody can be formulated for systemic or local (such as intra-tumor) administration. In one example, the antibody that specifically binds IGF-II is formulated for parenteral administration, such as intravenous administration.

The compositions for administration can include a solution of the antibody that specifically binds IGF-II dissolved in a pharmaceutically acceptable carrier, such as an aqueous carrier. A variety of aqueous carriers can be used, for example, buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of antibody in these formulations can vary widely, and will be selected primarily based on fluid volumes, viscosities, body weight and the like in accordance with the particular mode of administration selected and the subject's needs.

A typical pharmaceutical composition for intravenous administration includes about 0.1 to 10 mg of antibody per subject per day. Dosages from 0.1 up to about 100 mg per subject per day may be used, particularly if the agent is administered to a secluded site and not into the circulatory or lymph system, such as into a body cavity or into a lumen of an organ. Actual methods for preparing administrable compositions will be known or apparent to those skilled in the art and are described in more detail in such publications as *Remington's Pharmaceutical Science,* 19th ed., Mack Publishing Company, Easton, Pa. (1995).

Antibodies may be provided in lyophilized form and rehydrated with sterile water before administration, although they are also provided in sterile solutions of known concentration. The antibody solution is then added to an infusion bag containing 0.9% sodium chloride, USP, and typically administered at a dosage of from 0.5 to 15 mg/kg of body weight. Considerable experience is available in the art in the administration of antibody drugs, which have been marketed in the U.S. since the approval of RITUXAN® in 1997. Antibodies can be administered by slow infusion, rather than in an intravenous push or bolus. In one example, a higher loading dose is administered, with subsequent, maintenance doses being administered at a lower level. For example, an initial loading dose of 4 mg/kg may be infused over a period of some 90 minutes, followed by weekly maintenance doses for 4-8 weeks of 2 mg/kg infused over a 30 minute period if the previous dose was well tolerated.

In another embodiment, the invention provides a method for inhibiting IGF-IR activity by administering an antibody that binds IGF-II to a subject in need thereof. Thus, the antibodies disclosed herein can be used therapeutically. In one example, the subject is human. The antibody may be administered to a non-human mammal expressing an IGF-II with which the antibody cross-reacts (such as a primate, or a cynomolgus or rhesus monkey). It should be noted that animal models, such as primate models, can be useful for evaluating the therapeutic efficacy of antibodies of this invention.

The antibody can be administered to a subject having a disease or disorders in which the presence of high levels of IGF-I receptor activity has been shown to be or is suspected of being either responsible for the pathophysiology of the disease or disorder or is a factor that contributes to a worsening of the disease or disorder. Accordingly, inhibition of IGF-I receptor (IGF-IR) activity is expected to alleviate the symptoms and/or progression of the disorder. Such disorders may be evidenced, for example, by an increase in the levels of IGF-IR on the cell surface or by increased tyrosine autophosphorylation of IGF-IR in the affected cells or tissues of a subject suffering from the disorder.

The antibody that specifically binds IGF-II can be administered to slow or inhibit the growth of cells, such as tumor cells. In these applications, a therapeutically effective amount of an antibody is administered to a subject in an amount sufficient to inhibit growth of a tumor, or to inhibit a sign or a symptom of the tumor. Suitable subjects may include those with a tumor that expresses the IGF-I receptor, such as those suffering from a sarcoma, leukemia, prostate cancer, lung cancer, breast cancer, colon cancer, stomach cancer, uterine cancer, cervical cancer, esophageal cancer, liver cancer, pancreatic cancer, kidney cancer, thyroid cancer, brain cancer, or an ovarian cancer. In one embodiment, a method is provided for the treatment of cancer such as brain, squamous cell, bladder, gastric, pancreatic, breast, head, neck, esophageal, prostate, colorectal, lung, renal, kidney, ovarian, gynecological or thyroid cancer.

A method is also provided herein for the treatment of subjects having multiple myeloma, liquid tumor, liver cancer, thymus disorder, T-cell mediated auto-immune disease, endocronological disorder, ischemia, neurodegenerative disorder, lung cancer, bone cancer, pancreatic cancer, skin cancer, cancer of the head and neck, cutaneous or intraocular melanoma, uterine cancer, ovarian cancer, rectal cancer, cancer of the anal region, stomach cancer, colon cancer, breast cancer, gynecologic tumors (such as uterine sarcomas, carcinoma of the fallopian tubes, carcinoma of the endometrium, carcinoma of the cervix, carcinoma of the vagina or carcinoma of the vulva), Hodgkin's disease, cancer of the esophagus, cancer of the small intestine, cancer of the endocrine system (such as cancer of the thyroid, parathyroid or adrenal glands), sarcomas of soft tissues, cancer of the urethra, cancer of the penis, prostate cancer, chronic or acute leukemia, solid tumors of childhood, lymphocytic lymphomas, cancer of the bladder, cancer of the kidney or ureter (such as renal cell carcinoma, carcinoma of the renal pelvis), or neoplasms of the central nervous system (such as primary CNS lymphoma, spinal axis tumors, brain stem gliomas or pituitary adenomas). In several examples, the human antibody that binds IGF-II is administered to a patient with prostate cancer, glioma or fibrosarcoma. In additional examples, a human antibody that binds IGF-II is administered to a subject with lung, breast, prostate or colon cancer. In other examples, the method causes the tumor not to increase in weight or volume or to decrease in weight or volume.

Amounts effective for this use will depend upon the severity of the disease and the general state of the patient's health. A therapeutically effective amount of the antibody is that which provides either subjective relief of a symptom(s) or an objectively identifiable improvement as noted by the clinician or other qualified observer. In one example, the amount of the antibody is sufficient to inhibit phosphorylation of the IGF-I receptor. These compositions can be administered in conjunction with another chemotherapeutic agent, either simultaneously or sequentially.

Many chemotherapeutic agents are presently known in the art. In one embodiment, the chemotherapeutic agents is selected from the group consisting of mitotic inhibitors, alkylating agents, anti-metabolites, intercalating antibiotics, growth factor inhibitors, cell cycle inhibitors, enzymes, topoisomerase inhibitors, anti-survival agents, biological response modifiers, anti-hormones, e.g. anti-androgens, and anti-angiogenesis agents.

Anti-angiogenesis agents, such as MMP-2 (matrix-metalloproteinase 2) inhibitors, MMP-9 (matrix-metalloproteinase 9) inhibitors, and COX-II (cyclooxygenase II) inhibitors, can be used in conjunction with a compound of the invention. Examples of useful COX-II inhibitors include CELEBREX™(alecoxib), valdecoxib, and rofecoxib. Examples of useful matrix metalloproteinase inhibitors are described in PCT Publication No. WO 96/33172 (published Oct. 24, 1996), PCT Publication No. WO 96/27583 (published Mar. 7, 1996), European Patent Application No. 97304971.1 (filed Jul. 8, 1997), European Patent Application No. 99308617.2 (filed Oct. 29, 1999), PCT Publication No. WO 98/07697 (published Feb. 26, 1998), PCT Publication No WO 98/03516 (published Jan. 29, 1998), PCT Publication No WO 98/34918 (published Aug. 13, 1998), PCT Publication No WO 98/34915 (published Aug. 13, 1998), PCT Publication No WO 98/33768 (published Aug. 6, 1998), PCT Publication No WO 98/30566 (published Jul. 16, 1998), European Patent Publication 606,046 (published Jul. 13, 1994), European Patent Publication 931,788 (published Jul. 28, 1999), PCT Publication No WO 90/05719 (published May 31, 1990), PCT Publication No WO 99/52910 (published Oct. 21, 1999), PCT Publication No WO 99/52889 (published Oct. 21, 1999), PCT Publication No WO 99/29667 (published Jun. 17, 1999), PCT International Application No. PCT/IB98/01113 (filed Jul. 21, 1998), European Patent Application No. 99302232.1 (filed Mar. 25, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997). In one example, the MMP inhibitors do not induce arthralgia upon administration. In another example, the MMP inhibitor selectively inhibits MMP-2 and/or MMP-9 relative to the other matrix-metalloproteinases (such as MMP-1, MMP-3, MMP-4, MMP-5, MMP-6, MMP-7, MMP-8, MMP-10, MMP-11, MMP-12, and MMP-13). Some specific examples of MMP inhibitors of use are AG-3340, RO 32-3555, RS 13-0830, 3-[[4-(4-fluoro-phenoxy)-benzenesulfonyl]-(1-hydroxycarbamoyl-cyclopentyl)-amino]-propionic acid; 3-exo-3-[4-(4-fluoro-phenoxy)-benzenesulfonylamino]-8-oxa-bicyclo[3.2.1]octane-3-carboxylic acid hydroxyamide; (2R,3R) 1-[4-(2-chloro-4-fluoro-benzyloxy)-benzenesulfonyl]-3-hydroxy-3-methyl-piperidine-2-carboxylic acid hydroxyamide; 4-[4-(4-fluoro-phenoxy)-benzenesulfonylamino]-tetrahydro-pyran-4-carboxylic acid hydroxyamide; 3-[[4-(4-fluoro-phenoxy)-benzenesulfonyl]-(1-hydroxycarbamoyl-cyclobutyl)-amino]-propionic acid; 4-[4-(4-chloro-phenoxy)-benzenesulfonylamino]-tetrahydro-pyran-4-carboxylic acid hydroxyamide; (R) 3-[4-(4-chloro-phenoxy)-benzenesulfonylamino]-tetrahydro-pyran-3-carboxylic acid hydroxyamide; (2R,3R) 1-[4-(4-fluoro-2-methyl-benzyloxy)-benzenesulfonyl]-3-hydroxy-3-methyl-piperidine-2-carboxylic acid hydroxyamide; 3-[[4-(4-fluoro-phenoxy)-benzenesulfonyl]-(1-hydroxycarbamoyl-1-methyl-ethyl)-amino]-propionic acid; 3-[[4-(4-fluoro-phenoxy)-benzenesulfonyl]-(4-hydroxycarbamoyl-tetrahydro-pyran-4-yl)-amino]-propionic acid; 3-exo-3-[4-(4-chloro-phenoxy)-benzenesulfonylamino]-8-oxaicyclo[3.2.1]octane-3-carboxylic acid hydroxyamide; 3-endo-3-[4-(4-fluoro-phenoxy)-benzenesulfonylamino]-8-oxa-icyclo[3.2.1]octane-3-carboxylic acid hydroxyamide; and (R) 3-[4-(4-fluoro-phenoxy)-benzenesulfonylamino]-tetrahydro-furan-3-carboxylic acid hydroxyamide; and pharmaceutically acceptable salts and solvates of said compounds.

The antibodies that specifically bind IGF-II can also be used with signal transduction inhibitors, such as agents that can inhibit EGF-R (epidermal growth factor receptor) responses, such as EGF-R antibodies, EGF antibodies, and molecules that are EGF-R inhibitors; VEGF (vascular endothelial growth factor) inhibitors, such as VEGF receptors and molecules that can inhibit VEGF; and erbB2 receptor inhibitors, such as organic molecules or antibodies that bind to the erbB2 receptor, for example, HERCEPTIN™ (Genentech, Inc.). EGF-R inhibitors are described in, for example in PCT Publication Nos. WO 95/19970 (published Jul. 27, 1995), WO 98/14451 (published Apr. 9, 1998), WO 98/02434 (published Jan. 22, 1998), and U.S. Pat. No. 5,747,498 (issued May 5, 1998). EGFR-inhibiting agents also include, but are not limited to, the monoclonal antibodies C225 and anti-EGFR 22Mab (ImClone Systems Incorporated), ABX-EGF (Abgenix/Cell Genesys), EMD-7200 (Merck KgaA), EMD-5590 (Merck KgaA), MDX-447/H-477 (Medarex Inc. and Merck KgaA), and the compounds ZD-1834, ZD-1838 and ZD-1839 (AstraZeneca), PKI-166 (Novartis), PKI-166/CGP-75166 (Novartis), PTK 787 (Novartis), CP 701 (Cephalon), leflunomide (Pharmacia/Sugen), Cl-1033 (Warner Lambert Parke Davis), Cl-1033/PD 183,805 (Warner Lambert Parke Davis), CL-387,785 (Wyeth-Ayerst), BBR-1611 (Boehringer Mannheim GmbH/Roche), Naamidine A (Bristol Myers Squibb), RC-3940-II (Pharmacia), BIBX-1382 (Boehringer Ingelheim), OLX-103 (Merck & Co.), VRCTC-310 (Ventech Research), EGF fusion toxin (Seragen Inc.), DAB-389 (Seragen/Lilgand), ZM-252808 (Imperial Cancer Research Fund), RG-50864 (INSERM), LFM-A12 (Parker Hughes Cancer Center), WHI-P97 (Parker Hughes Cancer Center), GW-282974 (Glaxo), KT-8391 (Kyowa Hakko) and EGF-R Vaccine (York Medical/Centro de Immunologia Molecular (CIM)).

VEGF inhibitors, for example SU-5416 and SU-6668 (Sugen Inc.), SH-268 (Schering), and NX-1838 (NeXstar) can also be used in conjunction with an antibody that specifically binds IGF-II. VEGF inhibitors are described in, for example in PCT Publication No. WO 99/24440 (published May 20, 1999), PCT International Application PCT/IB99/00797 (filed May 3, 1999), PCT Publication No. WO 95/21613 (published Aug. 17, 1995), PCT Publication No. WO 99/61422 (published Dec. 2, 1999), U.S. Pat. No. 5,834,504 (issued Nov. 10, 1998), PCT Publication No. WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), PCT Publication No. WO 99/10349 (published Mar. 4, 1999), PCT Publication No. WO 97/32856 (published Sep. 12, 1997), PCT Publication No. WO 97/22596 (published Jun. 26, 1997), PCT Publication No. WO 98/54093 (published Dec. 3, 1998), PCT Publication No. WO 98/02438 (published Jan. 22, 1998), WO 99/16755

(published Apr. 8, 1999), and PCT Publication No. WO 98/02437 (published Jan. 22, 1998). Other examples of some specific VEGF inhibitors are IM862 (Cytran Inc.); anti-VEGF monoclonal antibody of Genentech, Inc.; and angiozyme, a synthetic ribozyme from Ribozyme and Chiron. These and other VEGF inhibitors can be used in conjunction with an antibody that specifically binds IGF-II.

ErbB2 receptor inhibitors, such as GW-282974 (Glaxo Wellcome pic), and the monoclonal antibodies AR-209 (Aronex Pharmaceuticals Inc.) and 2B-1 (Chiron), can furthermore be combined with the compound of the invention, for example those indicated in PCT Publication No. WO 98/02434 (published Jan. 22, 1998), PCT Publication No. WO 99/35146 (published Jul. 15, 1999), PCT Publication No. WO 99/35132 (published Jul. 15, 1999), PCT Publication No. WO 98/02437 (published Jan. 22, 1998), PCT Publication No. WO 97/13760 (published Apr. 17, 1997), PCT Publication No. WO 95/19970 (published Jul. 27, 1995), U.S. Pat. No. 5,587,458 (issued Dec. 24, 1996), and U.S. Pat. No. 5,877,305 (issued Mar. 2, 1999). ErbB2 receptor inhibitors of use are also described in U.S. Provisional Application No. 60/117,341, filed Jan. 27, 1999, and in U.S. Provisional Application No. 60/117,346, filed Jan. 27, 1999.

Single or multiple administrations of the compositions are administered depending on the dosage and frequency as required and tolerated by the patient. In any event, the composition should provide a sufficient quantity of at least one of the antibodies disclosed herein to effectively treat the patient. The dosage can be administered once but may be applied periodically until either a therapeutic result is achieved or until side effects warrant discontinuation of therapy. In one example, a dose of the antibody is infused for thirty minutes every other day. In this example, about one to about ten doses can be administered, such as three or six doses can be administered every other day. In a further example, a continuous infusion is administered for about five to about ten days. The subject can be treated at regular intervals, such as monthly, until a desired therapeutic result is achieved. Generally, the dose is sufficient to treat or ameliorate symptoms or signs of disease without producing unacceptable toxicity to the patient. In one example, the dose is sufficient to decrease the phosphorylation of the IGF-I receptor.

Controlled release parenteral formulations can be made as implants, oily injections, or as particulate systems. For a broad overview of protein delivery systems see, Banga, A. J., *Therapeutic Peptides and Proteins: Formulation, Processing, and Delivery Systems*, Technomic Publishing Company, Inc., Lancaster, Pa., (1995) incorporated herein by reference. Particulate systems include microspheres, microparticles, microcapsules, nanocapsules, nanospheres, and nanoparticles. Microcapsules contain the therapeutic protein, such as a cytotoxin or a drug, as a central core. In microspheres the therapeutic is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles are administered intravenously. Microparticles are typically around 100 µm in diameter and are administered subcutaneously or intramuscularly. See, for example, Kreuter, J., *Colloidal Drug Delivery Systems*, J. Kreuter, ed., Marcel Dekker, Inc., New York, N.Y., pp. 219-342 (1994); and Tice & Tabibi, *Treatise on Controlled Drug Delivery*, A. Kydonieus, ed., Marcel Dekker, Inc. New York, N.Y., pp. 315-339, (1992) both of which are incorporated herein by reference.

Polymers can be used for ion-controlled release of the antibody compositions disclosed herein. Various degradable and nondegradable polymeric matrices for use in controlled drug delivery are known in the art (Langer, *Accounts Chem. Res.* 26:537-542, 1993). For example, the block copolymer, polaxamer 407, exists as a viscous yet mobile liquid at low temperatures but forms a semisolid gel at body temperature. It has been shown to be an effective vehicle for formulation and sustained delivery of recombinant interleukin-2 and urease (Johnston et al., *Pharm. Res.* 9:425-434, 1992; and Pec et al., *J. Parent. Sci. Tech.* 44(2):58-65, 1990). Alternatively, hydroxyapatite has been used as a microcarrier for controlled release of proteins (Ijntema et al., Int. *J. Pharm.* 112:215-224, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa. (1993)). Numerous additional systems for controlled delivery of therapeutic proteins are known (see U.S. Pat. Nos. 5,055,303; 5,188,837; 4,235,871; 4,501,728; 4,837,028; 4,957,735; 5,019,369; 5,055,303; 5,514,670; 5,413,797; 5,268,164; 5,004,697; 4,902,505; 5,506,206; 5,271,961; 5,254,342 and U.S. Pat. No. 5,534,496).

Diagnostic Methods and Kits

A method is provided herein for the detection of the expression of IGF-II in vitro or in vivo. In one example, expression of IGF-II is detected in a biological sample. The sample can be any sample, including, but not limited to, tissue from biopsies, autopsies and pathology specimens. Biological samples also include sections of tissues, for example, frozen sections taken for histological purposes. Biological samples further include body fluids, such as blood, serum, plasma, sputum, spinal fluid or urine. A biological sample is typically obtained from a mammal, such as a rat, mouse, cow, dog, guinea pig, rabbit, or primate. In one embodiment, the primate is macaque, chimpanzee, or a human.

In several embodiments, a method is provided for detecting a malignancy such as a sarcoma, leukemia, prostate cancer, lung cancer, breast cancer, colon cancer, stomach cancer, uterine cancer, cervical cancer, esophageal cancer, liver cancer, pancreatic cancer, kidney cancer, thyroid cancer, brain cancer, or an ovarian cancer.

In additional embodiments, a method is provided for detecting multiple myeloma, liquid tumor, liver cancer, thymus disorder, T-cell mediated auto-immune disease, endocronological disorder, ischemia, neurodegenerative disorder, lung cancer, bone cancer, pancreatic cancer, skin cancer, cancer of the head and neck, cutaneous or intraocular melanoma, uterine cancer, ovarian cancer, rectal cancer, cancer of the anal region, stomach cancer, colon cancer, breast cancer, gynecologic tumors (such as uterine sarcomas, carcinoma of the fallopian tubes, carcinoma of the endometrium, carcinoma of the cervix, carcinoma of the vagina or carcinoma of the vulva), Hodgkin's disease, cancer of the esophagus, cancer of the small intestine, cancer of the endocrine system (such as cancer of the thyroid, parathyroid or adrenal glands), sarcomas of soft tissues, cancer of the urethra, cancer of the penis, prostate cancer, chronic or acute leukemia, solid tumors of childhood, lymphocytic lymphomas, cancer of the bladder, cancer of the kidney or ureter (such as renal cell carcinoma, carcinoma of the renal pelvis), or neoplasms of the central nervous system (such as primary CNS lymphoma, spinal axis tumors, brain stem gliomas or pituitary adenomas). A method is also provided for determining the prognosis of a subject with any of the malignancies listed above.

The invention provides a method for detecting IGF-II in a biological sample, wherein the method includes contacting a biological sample with a human antibody that binds IGF-II under conditions conductive to the formation of an immune complex, and detecting the immune complex, to detect the IGF-II in the biological sample. In one example, the detection of IGF-II in the sample indicates that the subject has a malignancy. In another example, the detection of IGF-II in the sample indicates that the subject is prone to metastasis.

In one embodiment, the human antibody that specifically binds IGF-II is directly labeled with a detectable label. In another embodiment, the human antibody that specifically binds IGF-II (the first antibody) is unlabeled and a second antibody or other molecule that can bind the human antibody that specifically binds IGF-II is labeled. As is well known to one of skill in the art, a second antibody is chosen that is able to specifically bind the specific species and class of the first antibody. For example, if the first antibody is a human IgG, then the secondary antibody may be an anti-human-lgG. Other molecules that can bind to antibodies include, without limitation, Protein A and Protein G, both of which are available commercially.

Suitable labels for the antibody or secondary antibody are described above, and include various enzymes, prosthetic groups, fluorescent materials, luminescent materials, magnetic agents and radioactive materials. Non-limiting examples of suitable enzymes include horseradish peroxidase, alkaline phosphatase, beta-galactosidase, or acetylcholinesterase. Non-limiting examples of suitable prosthetic group complexes include streptavidin/biotin and avidin/biotin. Non-limiting examples of suitable fluorescent materials include umbelliferone, fluorescein, fluorescein isothiocyanate, rhodamine, dichlorotriazinylamine fluorescein, dansyl chloride or phycoerythrin. A non-limiting exemplary luminescent material is luminol; a non-limiting exemplary a magnetic agent is gadolinium, and non-limiting exemplary radioactive labels include 125I, $^{131}$I, $^{35}$S or $^{3}$H.

In an alternative embodiment, IGF-II can be assayed in a biological sample by a competition immunoassay utilizing IGF-II standards labeled with a detectable substance and an unlabeled human antibody that specifically binds IGF-II. In this assay, the biological sample, the labeled IGF-II standards and the human antibody that specifically bind IGF-II are combined and the amount of labeled IGF-II standard bound to the unlabeled antibody is determined. The amount of IGF-II in the biological sample is inversely proportional to the amount of labeled IGF-II standard bound to the antibody that specifically binds IGF-II.

The immunoassays and method disclosed herein can be used for a number of purposes. In one embodiment, the human antibody that specifically binds IGF-II may be used to detect the production of IGF-II in cells in cell culture. In another embodiment, the antibody can be used to detect the amount of IGF-II in a biological sample. Increased expression of IGF-II is associated with several types of cancer, including a sarcoma, leukemia, prostate cancer, lung cancer, breast cancer, colon cancer, stomach cancer, uterine cancer, cervical cancer, esophageal cancer, liver cancer, pancreatic cancer, kidney cancer, thyroid cancer, brain cancer, or an ovarian cancer. Thus, the level of IGF-II can be used to diagnose, or determine the prognosis of, a sarcoma, leukemia, prostate cancer, lung cancer, breast cancer, colon cancer, stomach cancer, uterine cancer, cervical cancer, esophageal cancer, liver cancer, pancreatic cancer, kidney cancer, thyroid cancer, brain cancer, or an ovarian cancer, in a subject.

In one embodiment, a kit is provided for detecting IGF-II in a biological sample, such as a blood sample. Kits for detecting a polypeptide will typically comprise a human antibody that specifically binds IGF-II, such as any of the antibodies disclosed herein. In some embodiments, an antibody fragment, such as an Fv fragment is included in the kit. For in vivo uses, the antibody can be a scFv fragment. In a further embodiment, the antibody is labeled (for example, with a fluorescent, radioactive, or an enzymatic label).

In one embodiment, a kit includes instructional materials disclosing means of use of an antibody that specifically binds IGF-II. The instructional materials may be written, in an electronic form (such as a computer diskette or compact disk) or may be visual (such as video files). The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

In one embodiment, the diagnostic kit comprises an immunoassay. Although the details of the immunoassays may vary with the particular format employed, the method of detecting IGF-II in a biological sample generally includes the steps of contacting the biological sample with an antibody which specifically reacts, under immunologically reactive conditions, to an IGF-II polypeptide. The antibody is allowed to specifically bind under immunologically reactive conditions to form an immune complex, and the presence of the immune complex (bound antibody) is detected directly or indirectly.

Methods of determining the presence or absence of a cell surface marker are well known in the art. For example, the antibodies can be conjugated to other compounds including, but not limited to, enzymes, magnetic beads, colloidal magnetic beads, haptens, fluorochromes, metal compounds, radioactive compounds or drugs. The antibodies can also be utilized in immunoassays such as but not limited to radioimmunoassays (RIAs), enzyme linked immunosorbant assays (ELISA), or immunohistochemical assays. The antibodies can also be used for fluorescence activated cell sorting (FACS). A FACS employs a plurality of color channels, low angle and obtuse light-scattering detection channels, and impedance channels, among other more sophisticated levels of detection, to separate or sort cells (see U.S. Pat. No. 5,061,620). Any of the human antibodies that specifically bind IGF-II, as disclosed herein, can be used in these assays. Thus, the antibodies can be used in a conventional immunoassay, including, without limitation, an ELISA, an RIA, FACS, tissue immunohistochemistry, Western blot or immunoprecipitation.

EXAMPLES

Example 1

Identification and Characterization of Novel IGF-II Fab Antibodies

A DNA sequence encoding long IGF-II was cloned from plasmid pRc/CMV-Ligf2 into the *E. coli* expression vector pREST to generate pRSET-Ligf. BL21Lys cells transformed with pRSET-Ligf were grown in LB broth at 37° C. until reaching an $OD_{600}$ of 0.6, at which point they were induced with 1 mM IPTG for 3 hours. His-tagged long IGF-II (long $His_6$-IGF-II) was solubilized in PBS/0.5 M NaCl and purified using a HiTrap nickel-chelating column (Amersham Bio-sciences Corp.). Purified long His$_6$-IGF-II was dialyzed with PBS, and purity was assessed by SDS-PAGE.

Purified long His$_6$-IGF-II was used to screen a naïve human Fab phage library containing 5×10$^9$ unique clones. Long His$_6$-IGF-II was coated onto 96-well MaxiSorb plates (Nalge Nunc) at 2 μg/well, and non-specific binding sites were blocked with 3% filtered milk/PBS. Purified phage (1×10$^{12}$ pfu) was allowed to bind to the plates for 2 hours at room temperature, after which the wells were washed 10 times with PBS containing 0.05% Tween 20. Bound phage was eluted with freshly made 100 mM triethylamine, neutralized with 1 M Tris, pH 8.0, and used to infect exponentially growing TG-1 *E. coli* cells. Phage particles were rescued with M13 strain KO7 helper phage. This screening process was carried out four times, and phage output was measured after each round. The phage outputs for the four rounds were 1.7×10$^6$, 3.4×10$^6$, 2.0×10$^6$, and 1.6×10$^7$ pfu. Following each round, phage clones were pooled, and the binding affinity of each pool for IGF-II was measured by ELISA. Mature IGF-II was coated on narrow 96-well plates at 50 ng/well at 4° C. overnight, and then incubated with approximately 1×10$^6$ phage from each pool. Bound phage was detected with HRP-conjugated anti-M13 pAb (Pharmacia). The level of phage binding increased dramatically between the second and third rounds, then increased only slightly between the third and fourth rounds. The same results were observed using long His$_6$-IGF-II as the antigen.

Two hundred colonies from the third round and 200 colonies from the fourth round were picked and inoculated into 2YT medium in 96-well plates for soluble Fab expression. After 4-5 hours of growth, IPTG was added to induce Fab expression. After expression overnight, Fabs from each colony were subjected to ELISA using long IGF-II as antigen. IGF-II was coated on narrow 96-well plates at 50 ng/well at 4° C. overnight, and then incubated with 50 μl of expression supernatant.

Figure 3A:
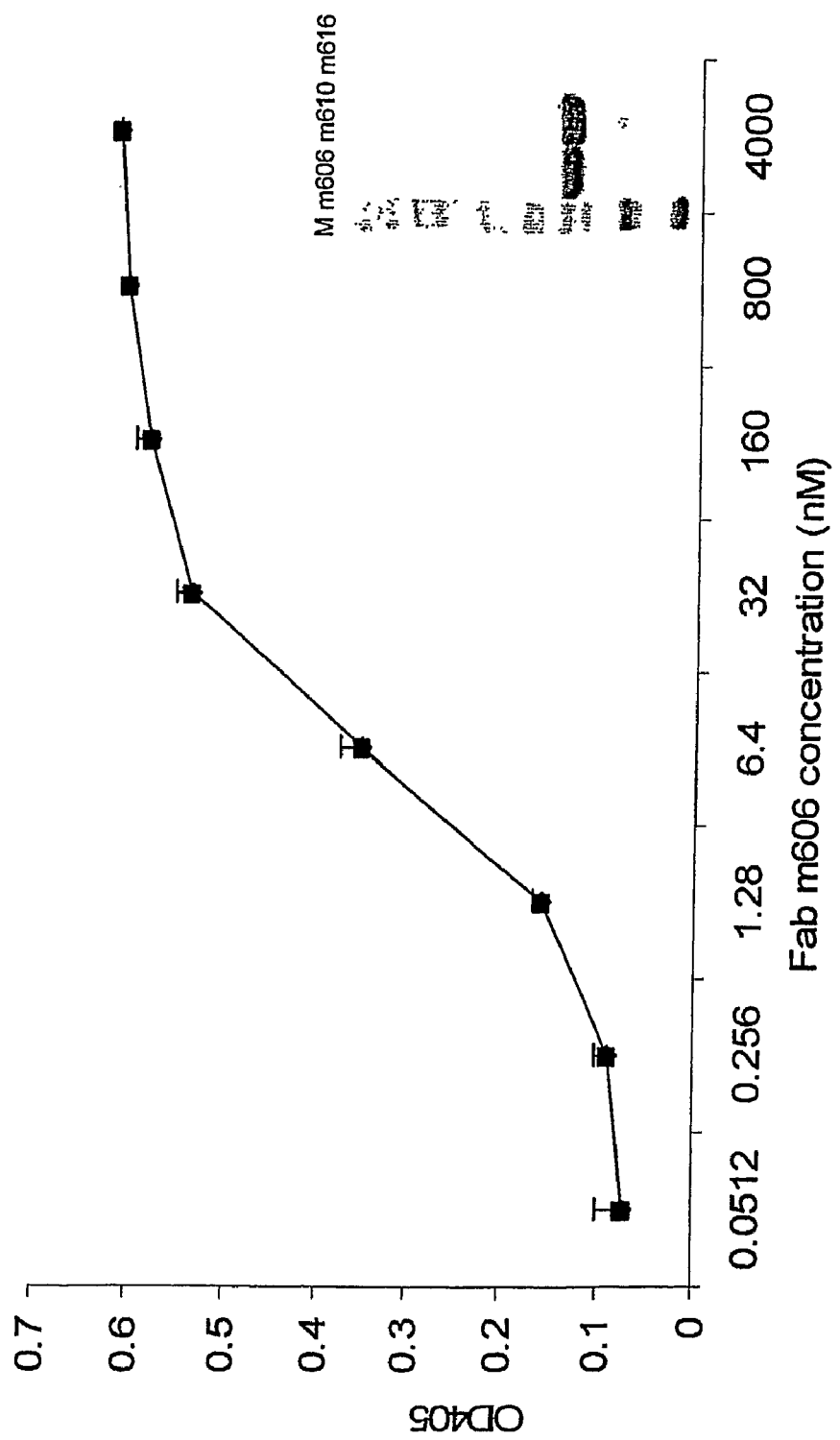
FIGS. 3A-3C is a set of graphs showing the binding affinity, specificity and binding kinetics of anti-IGF-II Fabs.

Ten Fabs that exhibited IGF-II binding were cloned into pComIII and individually transformed into HB2151 cells. Cells were shaken at 250 rpm in 2YT medium with 100 μg/ml ampicillin and 0.2% glucose at 37° C. until reaching an OD$_{600}$ of 0.5, at which point 1 mM IPTG was added to induce soluble Fab expression. After overnight growth at 30° C., cultures were harvested. Bacteria were centrifuged at 5,000 g for 15 minutes, and the pellet was resuspended in PBS with polymycin B (10,000 units/ml). Soluble Fab was released from the periplasm by incubation at room temperature for 45 minutes, and the extract was clarified at 15,000 g for 30 minutes. The clear supernatant was recovered for purification on a protein G column, and Fab expression levels were measured by SDS-PAGE. Experimental results for the m606, m610, and m616 clones are shown in FIG. 3A, inset. Expression levels were categorized as ++++, +++, ++, or −, with ++++ indicating a yield of >1 mg/L of culture, +++ indicating a yield of 1 mg/L to 0.1 mg/L, ++ indicating a yield of <0.1 mg/L but still high enough for Fab purification, + indicating a faintly detectable level of expression insufficient for Fab purification, and − indicating no expression. Five of the clones (m606, m610, m616, m641, and m627) were expressed at significant levels, with m606 and m610 showing the most expression (Table 1).

Fab from the five clones that showed significant expression levels were subjected to ELISA using long IGF-II as antigen. Antigen were coated on narrow 96-well plates at 50 ng/well at 4° C. overnight, and then incubated with Fab at concentrations ranging from 4 μM to 1.28 μM. Bound Fab was detected with HRP-conjugated anti-FLAG mAb (1:1000) (Sigma), and the reaction was read at OD$_{405}$. Experimental results for the m606 clone are shown in FIG. 3A. The binding affinity of each clone for long IGF-II was categorized as ++++, +++, ++, or −, with ++++ indicating a binding affinity of 1 nM or lower, +++ indicating a binding affinity between 1 nM and 10 nM, ++ indicating a binding affinity of 10 nM or higher, and − indicating no binding affinity. Three of the clones (m606, m610, and m616) bound long IGF-II, with m606 and m610 displaying a higher affinity than m616 (Table 1).

TABLE 1

| Clone # | Binding | Expression |
|---------|---------|------------|
| m606 | ++++ | ++++ |
| m610 | ++++ | ++++ |
| m616 | +++ | ++ |
| m618 | | − |
| m622 | | |
| m624 | | − |
| m626 | | |
| m627 | − | + |
| m635 | | − |
| m641 | − | ++ |

Figure 3B:
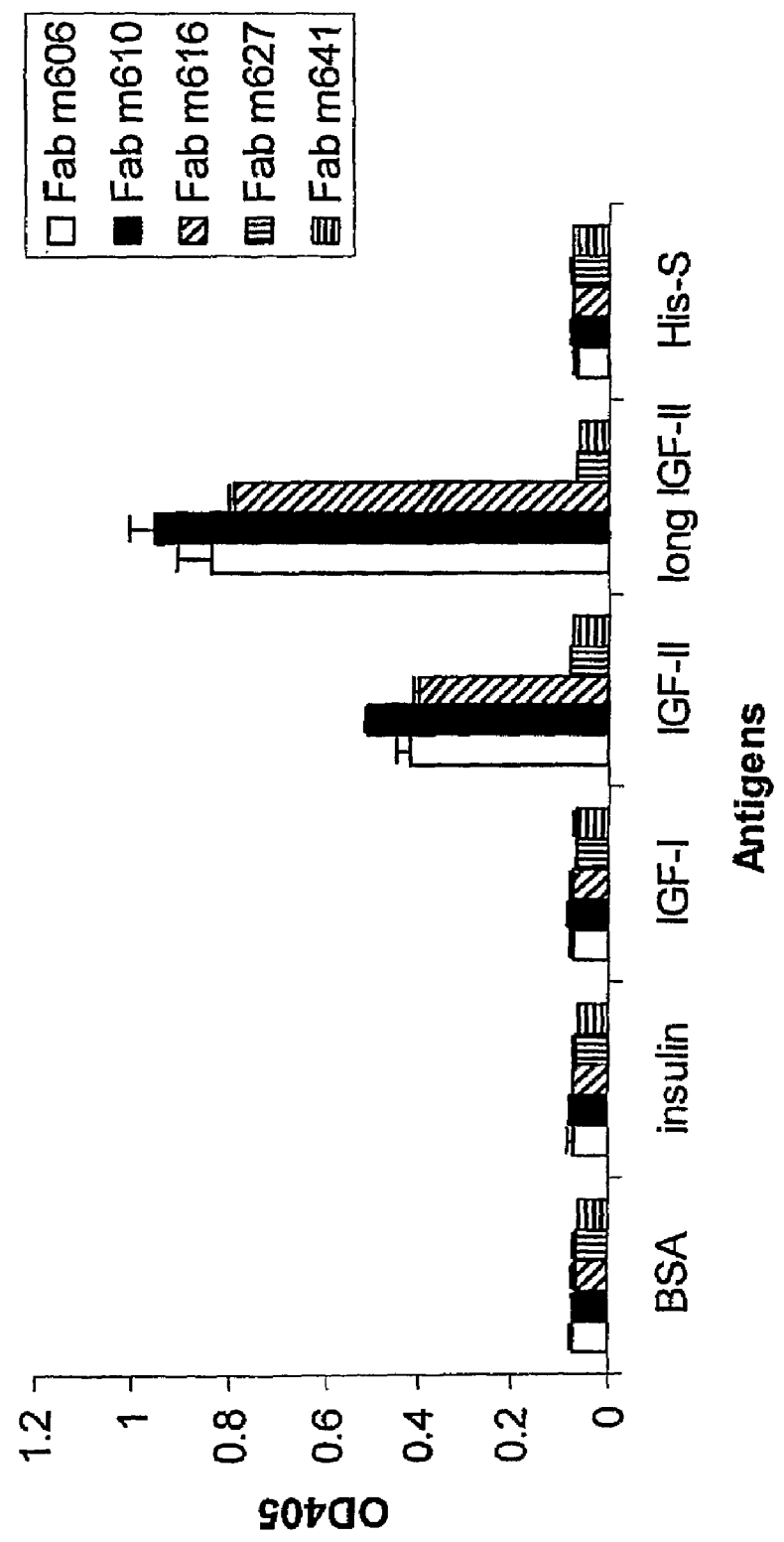
Figure 3C:
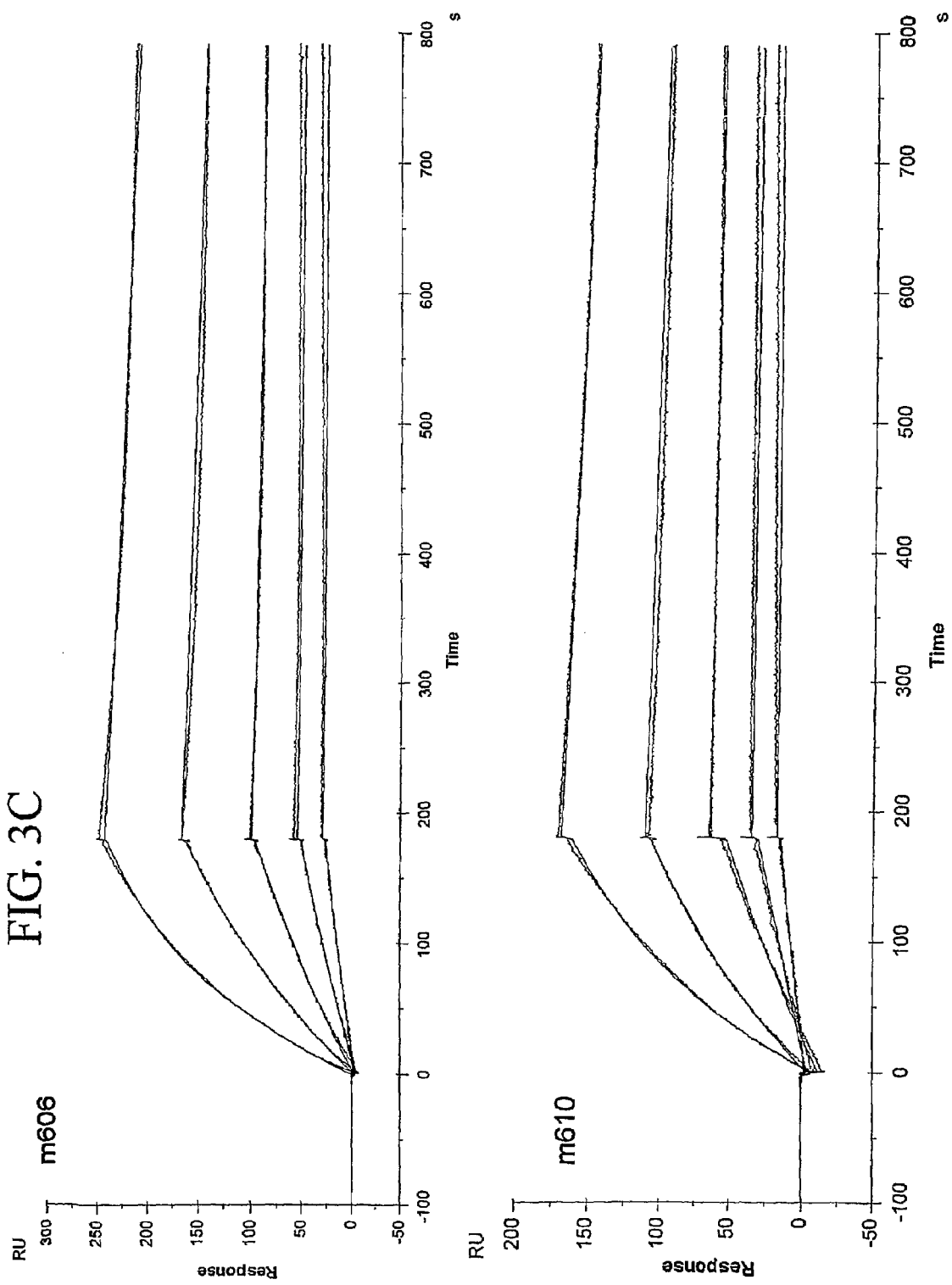

The ELISA was repeated for each of the five expressed clones using mature IGF-II, IGF-I, and insulin as antigens. Control ELISAs utilized BSA and His-S as antigens. None of the five clones displayed binding affinity for insulin or IGF-I. m606, m610, and m616 all bound mature IGF-II, but with lower affinity than long IGF-II. The results of these binding assays are summarized in FIG. 3B. The amino acid sequences of the light chains of m606, m610, and m616 are set forth in SEQ. ID. NOs: 7, 9, and 11, respectively, and the sequences of the heavy chains are set forth in SEQ. ID. NOs: 8, 10, and 12, respectively.

m606 and m610 were selected for further study based on their high binding affinity for long IGF-II. Biacore analysis was used to examine their binding affinities in more detail. The results of this analysis are shown in FIG. 3C. The $k_a$ and $k_d$ for m606 binding to long IGF-II was 3.51×10$^5$ M$^{-1}$s$^{-1}$ and 2.5×10$^{-4}$ s$^{-1}$, respectively, and the K$_A$ and K$_D$ were 1.41×10$^9$ M$^{-1}$ and 7.11×10$^{-10}$ M, respectively. The $k_a$ and $k_d$ for m610 binding to long IGF-II was 2.86×10$^5$ M$^{-1}$s$^{-1}$ and 2.62×10$^{-4}$ s$^{-1}$, respectively, and the K$_A$ and K$_D$ were 1.09×10$^9$ M$^{-1}$ and 9.18×10$^{-10}$ M, respectively.

Example 2

Effect of m606 and m610 Fabs on IGF-IR Phosphorylation In Vitro

Figure 5A:
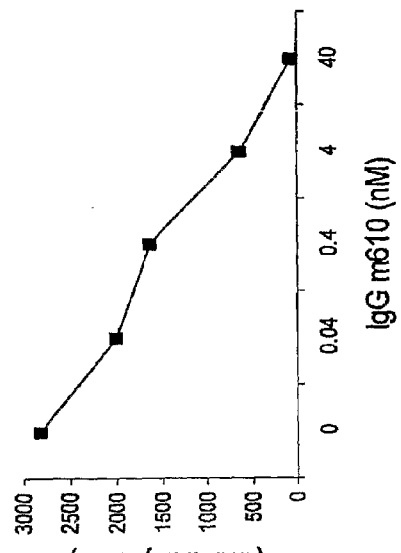
FIGS. 5A-5C are digital images and a graph illustrating that IGF-II antibodies inhibited IGF-II-induced phosphorylation of IGF-IR and insulin receptor in the breast cancer MCF-7 cells.
Figure 5B:
Figure 5C:
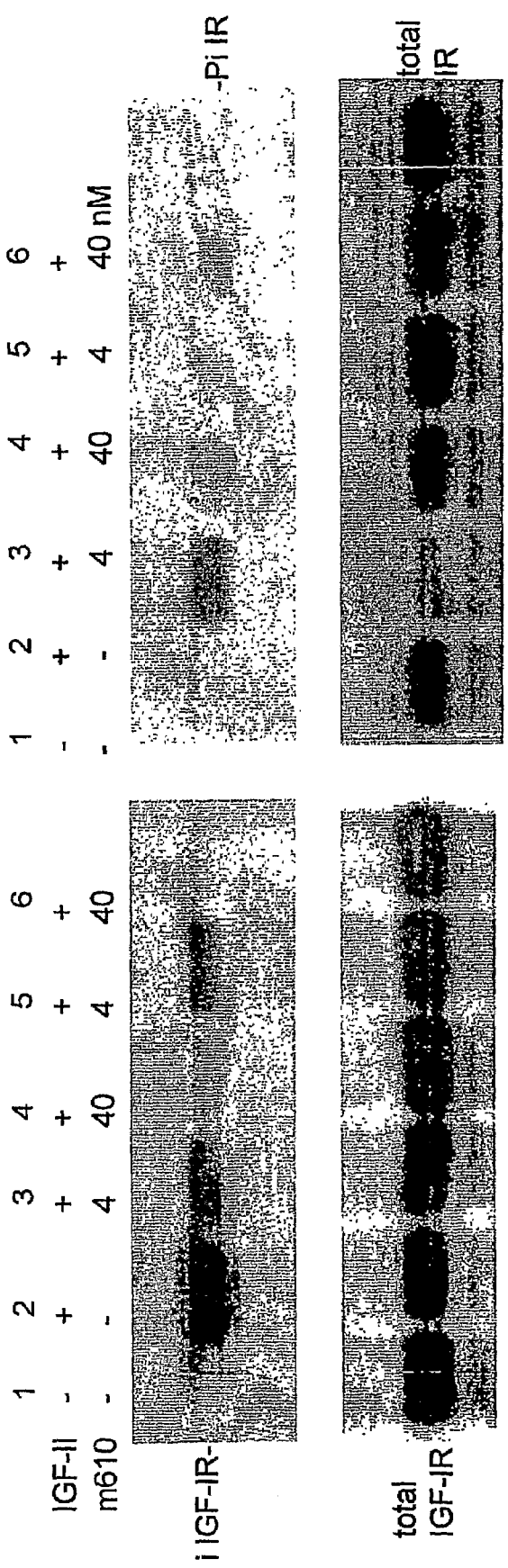
Figure 6:
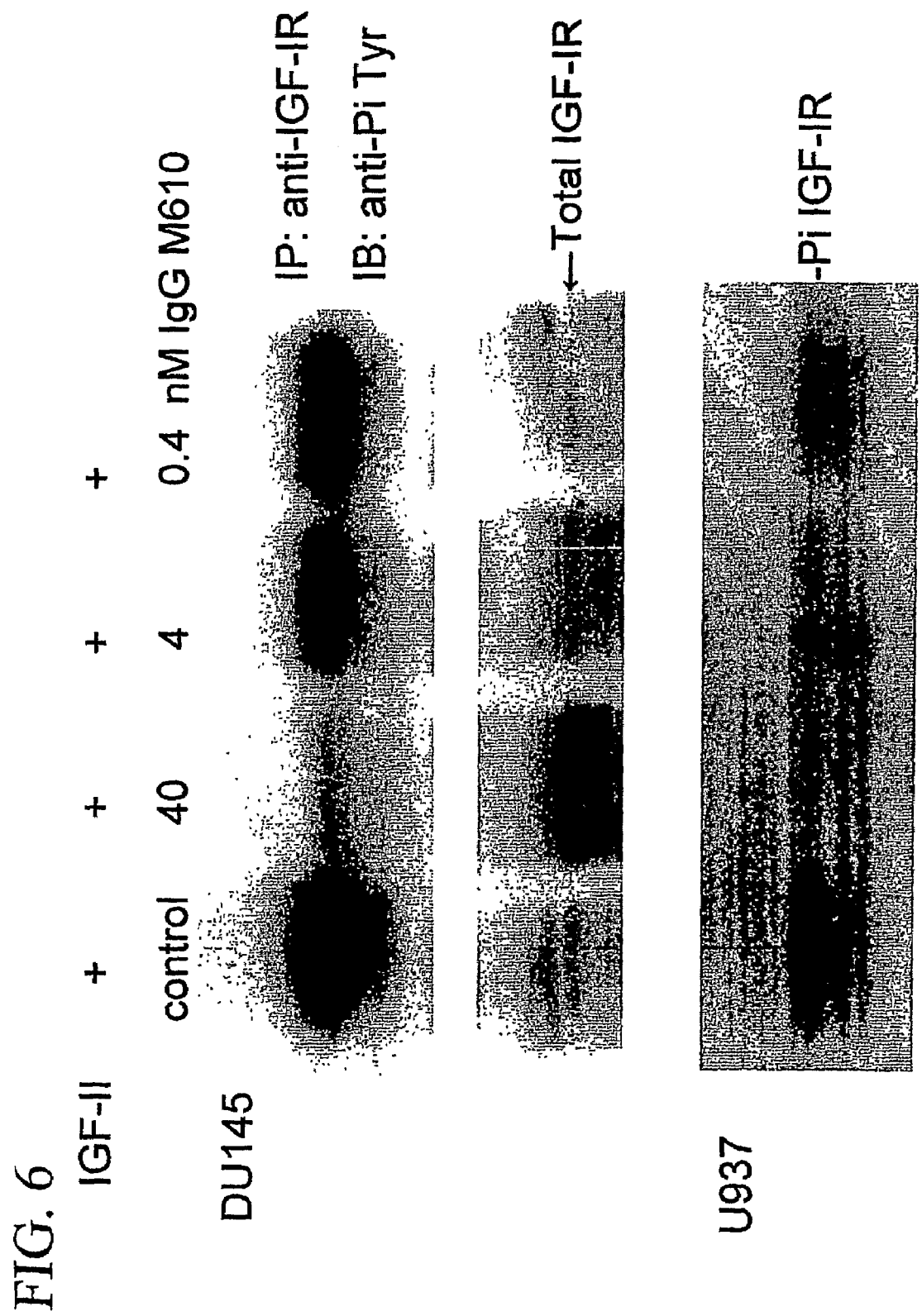
FIG. 6 is a digital image showing that IGF-II antibodies (IgG M610) also inhibited phosphorylation of IGF-IR in prostate cancer cell line DU145 and leukemia U937 cells. The experimental procedure was the same as in FIG. 5A.

MCF-7 breast cancer cells were seeded in 6-well plates (1×10$^6$ cells/well) in complete growth medium. After overnight culture, cell were rinsed with serum-free DMEM and cultured in serum-free DMEM for 6 hours. Cells were then incubated with 40 nM m606, m610, or C-Fab or 4 nM IgG6 for 30 minutes. 10 nM IGF-II was added to the wells to stimulate cells. After 20 minutes, cells were chilled on ice, rinsed in cold PBS, and lysed in 1 ml of lysis buffer (50 mM Hepes, ph 7.4, 150 mM NaCl, 10% glycerol, 1% Triton X100, 1.5 mM MgCl$_2$, 2 mM sodium vandate, and protease inhibitors). Lysates were left on ice for 30 minutes, then centrifuged at 17,000 g for 30 minutes. Following centrifugation, the supernatant was immunoprecipitated with 20 μl of protein G sepharose 4B and 2 μg of rabbit anti-IGF-IR beta (C-20, Santa Cruz). Immunoprecipitant was subjected to SDS-PAGE, and the gel was analyzed by Western blotting using an anti-Pi tyrosine antibody. m606 and m610 both reduced the level of IGF-II-mediated IGF-IR phosphorylation (FIG. 6). The experiments were repeated with m610 using concentrations ranging from 0 to 40 nM. It was found that m610 inhibited IGF-IR phosphorylation in a dose-dependent manner, with almost complete inhibition at a concentration of 40 nM (FIGS. 5A-5C).

Example 3

Creation and Characterization of IgG m606 and IgG m610 m606 and m610 Fabs in pComIII were cloned into pDR12, which allows simultaneous expression of heavy and light chain sequences. The heavy chain sequence of each Fab was cloned into pDR12 via XbaI and SacI sites, and the light chain sequence was cloned into pDR12 via HindIII and EcoRI sites. CellFectin (Invitrogen) was used to transfect the plasmids into 293 Free Style cells (Invitrogen). Four days after transfection, the culture supernatant was harvested, and IgGs were purified on protein G columns.

Figure 4:
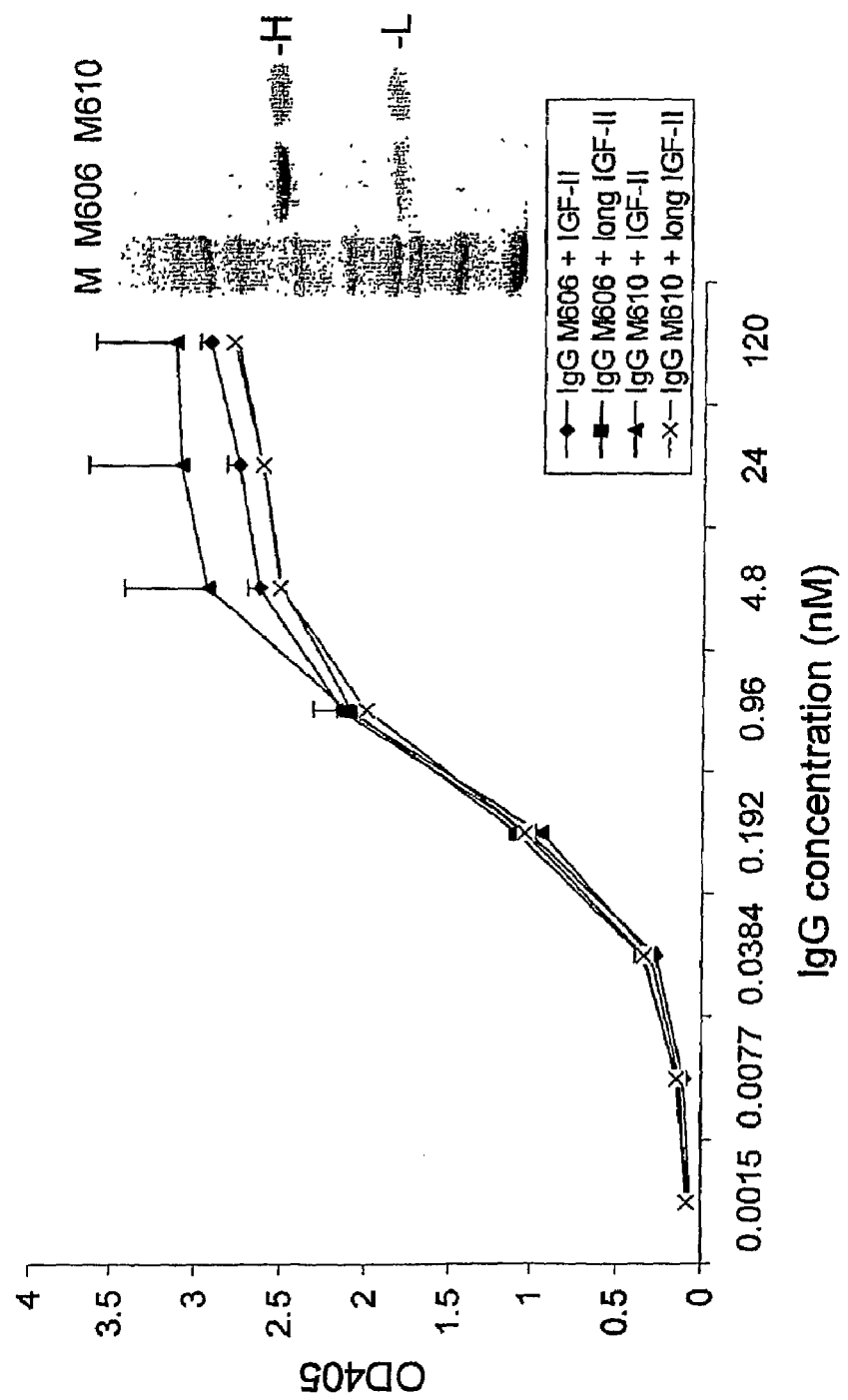
FIG. 4 is a graph and a digital image showing in vitro binding of IgG1 m606 and m610 to mature and precursor forms of IGF-II immobilized on ELISA plate. Binding of the antibodies was measured by ELISA with 50 ng of either mature or precursor IGF-II immobilized on plates.
Figure 9:
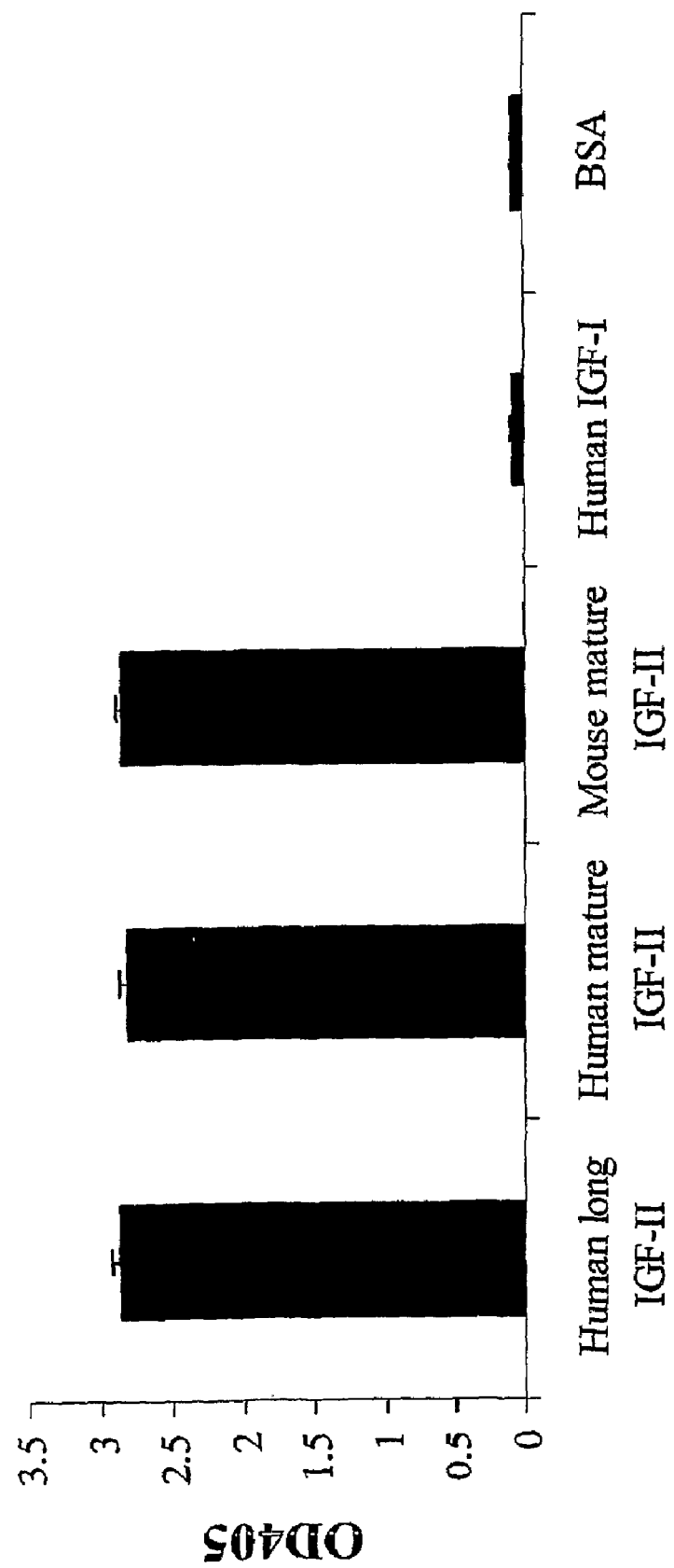
FIG. 9 is a bar graph showing that m610 specifically binds mouse IGF-II and human IGF-II. Human or mouse IGF-II, IGF-I and BSA were coated on ELISA plate. M610 IgG was used at 2 nM, well above its IC50. Binding of m610 to antigens was detected with anti-human IgG-HRP antibody.

The binding affinity of m606 and m610 IgGs for both long IGF-II and mature IGF-II was measured by ELISA. Both IgGs bound long and mature IGF-II at concentrations as low as approximately 0.12 nM, with a substantial increase in binding affinity at around 0.5 Nm (FIG. 4). The binding of m606 for human and mouse IGF-II was also investigated. It was determined that m606 specifically bound mouse IGF-II in addition to human IGF-II (FIG. 9).

Example 4

Effect of IgG m606 and IgG m610 on IGF-IR Phosphorylation In Vitro

MCF-7 breast cancer cells were cultured in the presence of varying concentrations of IgG m606 or IgG m610, ranging from 0 to 40 nM, using a protocol similar to that set forth in Example 2. Both IgG m606 and IgG m610 reduced the level of IGF-IR phosphorylation in a dose dependent manner, with each exhibiting an IC50 of around 1 mM. The level of inhibition was higher than that observed in Example 2 using m606 and m610 Fabs. Results for IgG m610 are shown in FIG. 5C. Similar results were observed when the experiment was repeated using DU145 prostate cancer cells (FIG. 6) and U937 leukemia cells. The IC50 for IgG m610 in these cells lines ranged from about 1 to about 10 nM.

These experiments will be repeated using a panel of approximately 60 cancer cell types. Based on the results obtained for MCF-7, DU145, and U937 cells, m606 and m610 inhibit IGF-IR phosphorylation in a wide variety of cancer cells.

Example 5

Effect of IgG m610 on Cancer Cell Growth, Proliferation and Motility

Figure 8A:
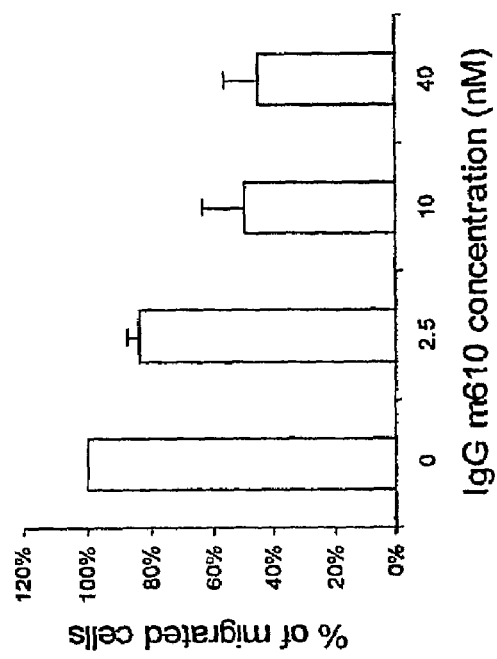
FIGS. 8A-8B are bar graphs showing IgG M610 inhibited DU145 cell growth, and reduced motility of MCF-7 cells in media containing 5% FBS. For the results shown in FIG. 8A, DU145 cells were starved in serum free medium for 6 hr followed by incubation with IGF-II at 10 nM final concentration and IgG m610 at the indicated final concentrations. Two days later, MTS was added to quantify viable cells. The reaction was monitored by measuring the optical density at 490 µm (OD490). The cells in the control sample (C) were incubated with the same volumes of serum free medium but in the absence of IGF-II and antibody. For the results shown in FIG. 8B, MCF-7 cells were cultured in serum free medium in trans-wells with 8 µm pores. The bottom wells contained 5% FBS and IgG m610 at the indicated concentrations. Cells migrated through the pores after 4 h were stained and counted. Shown is the percentage of the number of migrated cells (100% in the absence of antibody).

MCF-7 cells were grown on soft agar in the presence of IGF-II and varying concentrations of IgG m610. IgG M610 was found to reduce cell growth and proliferation (see FIG. 8A).

Cell motility was tested using Transwell culture plates (Cole-Parmer) with 8 µM pore size polycarbonate membrane. The bottom wells contained 2.6 ml DMEM, 10 nM IGF-II, and various concentrations of IgG m610. Control wells contained either complete growth medium (positive controls) or serum-free DMEM (negative controls). The top inserts contained 1.5 ml of 0.5 million MCF-7 single cell suspension in serum-free DMEM. Cells were incubated at 37° C. for 4 hours, after which cells attached to the upper side of the membrane were cleaned off with cotton-tipped applicators. Cells on the lower side of the membrane were stained using a Hema3 kit (Fisher), removed from the Transwell, mounted on microscopic slides, and counted under a microscope.

Figure 8B:
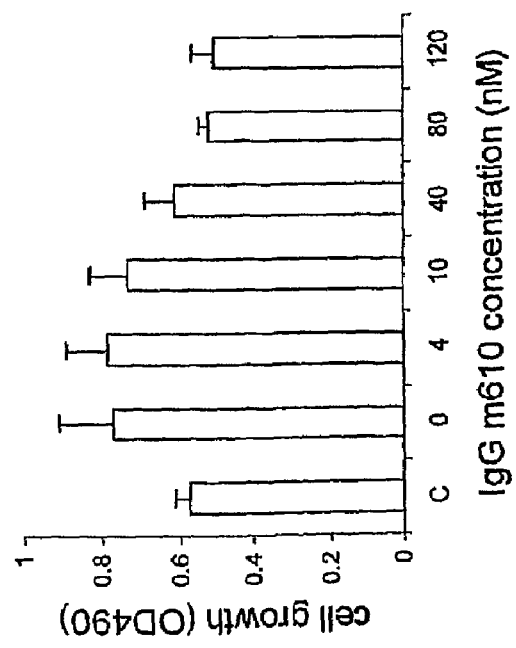

These experiments revealed that IgG m610 inhibited MCF-7 cell motility in a dose-dependent manner (FIG. 8).

Example 6

Animal Model Studies

The effect of both Fab and IgG forms of m606 and m610 on cancer cell motility, growth, and proliferation in vivo is examined using one or more mouse models.

A first set of mouse experiments utilizes the hollow fiber assay (Hollingshead 1995). Cells from one or more cancer cell lines are harvested, resuspended, and flushed into appropriate hollow fibers. Each fiber is sealed, incubated in culture medium for an appropriate period of time, and then implanted into a mouse intraperitoneally or subcutaneously. A single mouse is implanted with multiple fibers. Cells are quantified at the time of implantation. At an appropriate time period following implantation, sets of implanted mice are administered m606 and/or m610 at varying doses and time schedules. Administration can be carried out by any appropriate route. Sets of implant control mice receive no injections, or are injected with a control substance. Following the end of the dosage schedule, the hollow fibers are removed. The cancer cells are requantitated, and cell growth, proliferation, and motility is assessed. Fibers from implanted mice that are administered m606 and/or m610 display a decrease in one or more of these parameters.

A second set of animal experiments utilize SCID mice that have been injected with a number of cells from a human cancer cell line sufficient to cause tumor development. Sets of experimental mice are administered m606 and/or m610 at various doses and time schedules. Sets of control mice include untreated mice and mice administered a non-therapeutic agent such as saline or a buffering agent at doses and time schedules mirroring antibody administration. In addition, control experiments are performed in which m606 and m610 is administered to mice that have not been injected with cancer cells. These control experiments can be used to identify potential deleterious effects of antibody administration in healthy mice.

In experiments designed to measure the effect of m606 and m610 on early-stage tumor development, antibody administration begins within 0-3 days after cancer cell injection. In experiments designed to measure the effect of m606 and m610 on late-stage progression of tumor development, antibody administration begins after mice have begun to show one or more cancer symptoms.

The therapeutic efficacy of m606 and m610 is determined by comparing various physiological parameters of experimental and control mice at various time points following antibody administration. Physiological parameters that can be measured include tumor cell growth, proliferation, and motility, as well as other parameters such as survival rates.

Based on the in vitro studies discussed in the preceding Examples, it is expected that administration of m606 or m610 results in a decrease in tumor cell growth, proliferation, and motility in the mouse model. This will result in a decrease in cancer development, leading to increased survival rates.

Following these mouse model experiments, similar experiments can be carried out in various other mammalian animals such as canines or primates. These experiments are designed to test the efficacy and safety of m606 or m610 administration, and to optimize dosage levels and administration schedules.

It will be apparent that the precise details of the methods or compositions described may be varied or modified without departing from the spirit of the described invention. In view of the many possible embodiments to which the principles of our invention may be applied, it should be recognized that the illustrated embodiments are only examples of the invention and should not be taken as a limitation on the scope of the invention. Rather, the scope of the invention is defined by the following claims. We therefore claim as our invention all that comes within the scope and spirit of these claims.

We claim:

1. An isolated monoclonal antibody or an antigen binding fragment thereof, comprising a variable region of a heavy chain and a variable region of a light chain, and wherein the variable region of the light chain comprises amino acids 37-47 of the amino acid sequence set forth in SEQ ID NO: 8, amino acids 60-68 of the amino acid sequence set forth in SEQ ID NO: 8 and amino acids 99-109 of the amino acid sequence set forth in SEQ ID NO: 8, and wherein the variable region of the heavy chain comprises amino acids 34-41 of the amino acid sequence set forth in SEQ ID NO: 11, amino acids 59-65 of the amino acid sequence set forth in SEQ ID NO: 11 and amino acids 105-109 of the amino acid sequence set forth in SEQ ID NO: 11, and wherein the monoclonal antibody or the antigen binding fragment thereof specifically binds insulin-like growth factor II (IGF-II) with an equilibrium dissociation constant ($K_d$) of 1 nM or less and binds IGF-I with an equilibrium dissociation constant ($K_d$) of 1 mM or greater.

2. The isolated monoclonal antibody or antigen binding fragment of claim 1, wherein the variable region of the light chain comprises the amino acid sequence set forth as SEQ ID NO: 8.

3. The isolated monoclonal antibody or antigen binding fragment of claim 1, wherein the-variable region of the light chain of the monoclonal antibody comprises the amino acid sequence set forth in-SEQ ID NO: 8 and wherein the variable region of the heavy chain of the antibody comprises the amino acid sequence set forth in SEQ ID NO: 11.

4. The isolated monoclonal antibody or antigen binding fragment of claim 1, wherein the variable region of the heavy chain comprises the amino acid sequence set forth as SEQ ID NO: 11.

5. The antigen binding fragment of isolated monoclonal claim 1, wherein the antigen binding fragment is a Fab' fragment, a F(ab)'$_2$ fragment, or a disulfide stabilized Fv protein ("dsFv").

6. The isolated monoclonal human antibody of claim 1, wherein the antibody is an IgG or IgM.

7. The isolated monoclonal human antibody of claim 6, wherein the antibody is an $IgG_4$.

8. The isolated monoclonal antibody or antigen binding fragment of claim 1, wherein the antibody or the antigen binding fragment is labeled.

9. The isolated monoclonal antibody or antigen binding fragment of claim 8, wherein the label is a fluorescence, enzymatic, or radioactive label.

10. A composition comprising the monoclonal antibody or antigen binding fragment of claim 1 in a pharmaceutically acceptable carrier.

11. A method of treating a subject with prostate cancer, comprising administering to the subject a therapeutically effective amount of the composition of claim 10, wherein cells of the prostate cancer express an insulin-like growth factor (IGF)-I receptor thereby treating the prostate cancer in the subject.

12. The method of claim 11, wherein administering the therapeutically effective amount of the composition reduces metastasis.

13. The method of claim 11, wherein administering the therapeutically effective amount of the composition reduces the tumor burden.

14. The method of claim 11, wherein administering the therapeutically effective amount of the composition of claim 10 inhibits the phosphorylation of the IGF-I receptor.

15. A method of detecting insulin-like growth factor II (IGF-II), comprising
contacting a sample from the subject with the isolated monoclonal antibody or antigen binding fragment of claim 1; and
detecting binding of the isolated monoclonal antibody or the antigen binding fragment to the sample,
wherein an increase in the binding of the monoclonal antibody or the antigen binding fragment to the sample as compared to a control indicates the presence of IGF-II in the sample.

16. The method of claim 15, wherein the isolated monoclonal antibody is directly labeled.

17. The method of claim 15, further comprising
contacting a second antibody that specifically binds the isolated monoclonal antibody with the sample, and
detecting the binding of the second antibody,
wherein an increase in the binding of the second antibody as compared to a control indicates the presence of IGF-II in the sample.

18. The method of claim 15, wherein the sample is a blood, urine, biopsy, serum, sputum, plasma, or cerebral spinal fluid sample.

19. A method of inhibiting phosphorylation of an insulin-like growth factor-I receptor, comprising
contacting a cell that expresses the insulin like growth factor-I receptor with an effective amount of the isolated monoclonal antibody or antigen binding fragment of claim 1, thereby inhibiting the phosphorylation of the insulin-like growth factor-I receptor.

20. The method of claim 19, wherein the cell is in vitro.

21. The method of claim 19, wherein the cell is in vivo.

22. The method of claim 19, wherein the cell is a cancer cell.

23. An isolated nucleic acid encoding the monoclonal antibody or antigen binding fragment of claim 1.

24. The isolated nucleic acid of claim 23, operably linked to a heterologous promoter.

25. An expression vector comprising the isolated nucleic acid of claim 23.

26. An isolated host cell transformed with the nucleic acid of claim 23.

27. The isolated antibody of claim 1, wherein the antibody inhibits the phosphorylation of an insulin receptor.

28. The isolated monoclonal antibody or antigen binding fragment of claim 1, wherein the monoclonal antibody or the antigen binding fragment inhibits the motility of breast cancer cells in vitro.

29. The isolated monoclonal antibody or antigen binding fragment of claim 1, further comprising a human framework region.

30. The isolated monoclonal antibody of claim 1, wherein the antibody is an scFV.

31. The isolated monoclonal antibody or antigen binding fragment of claim 1, wherein the monoclonal antibody or the antigen binding fragment inhibits the phosphorylation of an insulin-like growth factor (IGF)-I receptor.

* * * * *